United States Patent
Yamamoto

(10) Patent No.: US 10,742,958 B2
(45) Date of Patent: Aug. 11, 2020

(54) ENDOSCOPE APPARATUS

(71) Applicant: OLYMPUS CORPORATION, Tokyo (JP)

(72) Inventor: Naoki Yamamoto, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 372 days.

(21) Appl. No.: 15/831,652

(22) Filed: Dec. 5, 2017

(65) Prior Publication Data

US 2018/0103246 A1 Apr. 12, 2018

Related U.S. Application Data

(63) Continuation of application No. PCT/JP2016/068636, filed on Jun. 23, 2016.

(30) Foreign Application Priority Data

Jun. 25, 2015 (JP) .................................. 2015-127415

(51) Int. Cl.
  *A61B 1/00* (2006.01)
  *H04N 13/239* (2018.01)
  (Continued)

(52) U.S. Cl.
  CPC ............ *H04N 13/239* (2018.05); *A61B 1/00* (2013.01); *A61B 1/04* (2013.01); *G02B 23/24* (2013.01);
  (Continued)

(58) Field of Classification Search
  None
  See application file for complete search history.

(56) References Cited

U.S. PATENT DOCUMENTS

2002/0137986 A1 9/2002 Ogawa
2008/0027277 A1 1/2008 Nakano
(Continued)

FOREIGN PATENT DOCUMENTS

CA  2 898 554 A1  7/2014
EP  2 241 922 A1  10/2010
(Continued)

OTHER PUBLICATIONS

Extended Supplementary European Search Report dated Feb. 5, 2019 in European Patent Application No. 16 81 4433.5.
(Continued)

*Primary Examiner* — Timothy J Neal
(74) *Attorney, Agent, or Firm* — Scully, Scott, Murphy & Presser, P.C.

(57) ABSTRACT

In this endoscope apparatus, an imaging optical system is disposed in a distal end of an endoscope insertion unit. An measurement processing unit performs a measurement process by the principle of triangulation on the basis of an image corresponding to an optical image obtained via an imaging optical system and camera parameters of a first position and a second position. A reliability determination unit determines the reliability of the measurement process. The measurement process is based on a measurement point set in the image corresponding to the optical image obtained via the imaging optical system at the first position. A notification control unit sends a notification to prompt a user to perform an operation of moving the distal end in a direction from the second position toward the first position when the reliability determination unit determines that the reliability is low.

26 Claims, 38 Drawing Sheets

(51) Int. Cl.
  *G02B 23/24* (2006.01)
  *A61B 1/04* (2006.01)
  *G06T 7/593* (2017.01)
  *H04N 13/246* (2018.01)
  *H04N 5/225* (2006.01)
(52) U.S. Cl.
  CPC .......... *G02B 23/2415* (2013.01); *G06T 7/593* (2017.01); *H04N 5/2256* (2013.01); *H04N 13/246* (2018.05); *G06T 2207/10068* (2013.01); *G06T 2207/30004* (2013.01); *H04N 2005/2255* (2013.01)

(56) References Cited

U.S. PATENT DOCUMENTS

| | | |
|---|---|---|
| 2009/0167847 A1 | 7/2009 | Doi |
| 2012/0256901 A1* | 10/2012 | Bendall ................ G06T 7/0004 345/419 |

FOREIGN PATENT DOCUMENTS

| | | |
|---|---|---|
| EP | 2700347 A1 | 2/2014 |
| EP | 2700348 A1 | 2/2014 |
| JP | 2001075019 A | 3/2001 |
| JP | 2004049638 A | 2/2004 |
| JP | 2008229219 A | 10/2008 |
| JP | 2012016573 A | 1/2012 |
| JP | 5001286 B2 | 8/2012 |
| JP | 2012239834 A | 12/2012 |
| JP | 2014147572 A | 8/2014 |
| WO | 2012161246 A1 | 11/2012 |

OTHER PUBLICATIONS

International Search Report dated Sep. 27, 2016 issued in PCT/JP2016/068636.

* cited by examiner

ENDOSCOPE APPARATUS

Priority is claimed on Japanese Patent Application No. 2015-127415, filed Jun. 25, 2015, and this application is a continuing application based on International Patent Application No. PCT/JP2016/068636, filed Jun. 23, 2016, the contents of the Japanese Application and the PCT Application are incorporated herein by reference.

BACKGROUND OF THE INVENTION

Field of the Invention

The present invention relates to an endoscope apparatus.

Description of Related Art

In recent years, endoscopes for industrial use have been widely used for observation of and inspection for cracks, corrosion, and the like inside boilers, turbines, engines, chemical plants, and the like. Recent endoscopes for industrial use have been configured such that a stereo optical adapter that images a subject from different viewpoints can be attached to a distal end of an endoscope. Due to this, it is possible to measure (stereoscopically measure) various spatial characteristics of a subject using the principle of triangulation (for example, see Japanese Unexamined Patent Application, First Publication No. 2008-229219).

SUMMARY OF THE INVENTION

According to a first aspect of the present invention, an endoscope apparatus includes an endoscope insertion unit, a first imaging optical system, a second imaging optical system, an imaging element, and a measurement processing unit. The first imaging optical system and the second imaging optical system are disposed at a distal end of the endoscope insertion unit so as to be separated from each other in a parallax direction. The imaging element generates a first image corresponding to a first optical image obtained via the first imaging optical system and a second image corresponding to a second optical image obtained via the second imaging optical system. The measurement processing unit includes a measurement point setting unit, a correspondence point searching unit, and a 3-dimensional coordinate calculation unit. The measurement point setting unit sets a measurement point in the first image. The correspondence point searching unit searches the second image for a correspondence point corresponding to the measurement point set by the measurement point setting unit. The 3-dimensional coordinate calculation unit calculates 3-dimensional coordinates of the measurement point by the principle of triangulation using the measurement point and the correspondence point searched for by the correspondence point searching unit. The endoscope apparatus further includes a reliability determination unit and a notification control unit. The reliability determination unit determines the reliability of a measurement process. The measurement process is performed on the basis of the measurement point. The notification control unit sends a notification to prompt a user to perform an operation of moving the distal end toward the first imaging optical system in the parallax direction when the reliability determination unit determines that the reliability is low.

According to a second aspect of the present invention, in the first aspect, the reliability determination unit may include a correlation value calculation unit and a comparison and determination unit. The correlation value calculation unit calculates a correlation value or a degree of difference between a position of the measurement point in the first image and a position of the correspondence point in the second image. The comparison and determination unit compares the correlation value or the degree of difference with a first predetermined value and determines the reliability on the basis of the comparison result.

According to a third aspect of the present invention, in the first aspect, the reliability determination unit may include an occlusion occurrence determination unit that determines whether or not occlusion has occurred. The reliability determination unit may determine that the reliability is low when the occlusion occurrence determination unit determines that occlusion has occurred.

According to a fourth aspect of the present invention, in the first aspect, the reliability determination unit may include a correlation value calculation unit, an occlusion occurrence determination unit, and a comparison and determination unit. The correlation value calculation unit calculates a correlation value or a degree of difference between a position of the measurement point in the first image and a position of the correspondence point in the second image. The occlusion occurrence determination unit determines whether or not occlusion has occurred. The comparison and determination unit determines the reliability on the basis of a comparison result obtained by comparing the correlation value or the degree of difference with a first predetermined value and a determination result obtained by the occlusion occurrence determination unit.

According to a fifth aspect of the present invention, in the third or fourth aspect, the occlusion occurrence determination unit may include an auxiliary measurement point setting unit, an object distance calculation unit, a difference calculation unit, and a difference determination unit. The auxiliary measurement point setting unit processes at least a video signal corresponding to the first image, thereby setting a first auxiliary measurement point on an epipolar line on the left side of the measurement point in the first image and setting a second auxiliary measurement point on the epipolar line on the right side of the measurement point in the first image. The object distance calculation unit calculates a first object distance at the first auxiliary measurement point and a second object distance at the second auxiliary measurement point. The difference calculation unit calculates a difference between the first object distance and the second object distance. The difference determination unit compares the difference with a second predetermined value and determines that occlusion has occurred when the difference is larger than the second predetermined value.

According to a sixth aspect of the present invention, an endoscope apparatus includes an endoscope insertion unit, a first imaging optical system, a second imaging optical system, an imaging element, a measurement processing unit, and a bending unit. The first imaging optical system and the second imaging optical system are disposed at a distal end of the endoscope insertion unit so as to be separated from each other in a parallax direction. The imaging element generates a first image corresponding to a first optical image obtained via the first imaging optical system and a second image corresponding to a second optical image obtained via the second imaging optical system. The bending unit is disposed in the distal end and bends the distal end. The measurement processing unit includes a measurement point setting unit, a correspondence point searching unit, and a 3-dimensional coordinate calculation unit. The measurement point setting unit sets a measurement point in the first image.

The correspondence point searching unit searches the second image for a correspondence point corresponding to the measurement point set by the measurement point setting unit. The 3-dimensional coordinate calculation unit calculates 3-dimensional coordinates of the measurement point by the principle of triangulation using the measurement point and the correspondence point searched for by the correspondence point searching unit. The endoscope apparatus further includes a reliability determination unit and a bending control unit. The reliability determination unit determines the reliability of a measurement process. The measurement process is performed on the basis of the measurement point. The bending control unit controls the bending unit so that the distal end is moved toward the first imaging optical system in the parallax direction when the reliability determination unit determines that the reliability is low.

According to a seventh aspect of the present invention, in the sixth aspect, the reliability determination unit may include a correlation value calculation unit and a comparison and determination unit. The correlation value calculation unit calculates a correlation value or a degree of difference between a position of the measurement point in the first image and a position of the correspondence point in the second image. The comparison and determination unit compares the correlation value or the degree of difference with a first predetermined value and determines the reliability on the basis of the comparison result.

According to an eighth aspect of the present invention, in the sixth aspect, the reliability determination unit may include an occlusion occurrence determination unit that determines whether or not occlusion has occurred. The reliability determination unit may determine that the reliability is low when the occlusion occurrence determination unit determines that occlusion has occurred.

According to a ninth aspect of the present invention, in the sixth aspect, the reliability determination unit may include a correlation value calculation unit, an occlusion occurrence determination unit, and a comparison and determination unit. The correlation value calculation unit calculates a correlation value or a degree of difference between a position of the measurement point in the first image and a position of the correspondence point in the second image. The occlusion occurrence determination unit determines whether or not occlusion has occurred. The comparison and determination unit determines the reliability on the basis of a comparison result obtained by comparing the correlation value or the degree of difference with a first predetermined value and a determination result obtained by the occlusion occurrence determination unit.

According to a tenth aspect of the present invention, in the eighth or ninth aspect, the occlusion occurrence determination unit may include an auxiliary measurement point setting unit, an object distance calculation unit, a difference calculation unit, and a difference determination unit. The auxiliary measurement point setting unit processes at least a video signal corresponding to the first image, thereby setting a first auxiliary measurement point on an epipolar line on the left side of the measurement point in the first image and setting a second auxiliary measurement point on the epipolar line on the right side of the measurement point in the first image. The object distance calculation unit calculates a first object distance at the first auxiliary measurement point and a second object distance at the second auxiliary measurement point. The difference calculation unit calculates the difference between the first object distance and the second object distance. The difference determination unit compares the difference with a second predetermined value and determines that occlusion has occurred when the difference is larger than the second predetermined value.

According to an eleventh aspect of the present invention, in the sixth aspect, the endoscope apparatus may further include a measurement point checking unit and a notification control unit. The bending control unit may include a measurement point estimation unit and a bending amount calculation unit. The measurement point estimation unit estimates 3-dimensional coordinates of the measurement point by processing at least a video signal corresponding to the first image and a video signal corresponding to the second image. The bending amount calculation unit calculates a bending amount for causing a point on a subject to be included in a field of view of the second imaging optical system. The point on the subject is at estimated 3-dimensional coordinates of the measurement point. Before the bending control unit performs bending control based on the bending amount, the measurement point checking unit may determine whether or not the point on the subject would be included in a field of view of the first imaging optical system if the distal end were virtually bent by the bending amount. The notification control unit may send a notification to prompt a user to perform an operation of moving the distal end away from the subject when it is determined that the point on the subject would not be included in the field of view of the first imaging optical system if the distal end were virtually bent by the bending amount.

According to a twelfth aspect of the present invention, in the sixth aspect, the parallax direction may be a direction from a first optical center of the first imaging optical system toward a second optical center of the second imaging optical system. The bending control unit may include a measurement point estimation unit, an edge detection unit, an edge position calculation unit, a virtual line calculation unit, and a bending amount calculation unit. The measurement point estimation unit estimates 3-dimensional coordinates of the measurement point by processing at least a video signal corresponding to the first image and a video signal corresponding to the second image. The edge detection unit detects an edge at which a change in image density of the first image is relatively large by processing at least the video signal corresponding to the first image. The edge is on the parallax direction side of the measurement point in the first image. The edge position calculation unit calculates 3-dimensional coordinates of an edge point at the edge by the principle of triangulation by processing at least the video signal corresponding to the first image and the video signal corresponding to the second image. The virtual line calculation unit calculates a virtual line that passes through estimated 3-dimensional coordinates of the measurement point and 3-dimensional coordinates of the edge point. The bending amount calculation unit calculates a bending amount necessary for moving the second optical center to a position on the virtual line or a position on an opposite side of the virtual line in the parallax direction.

According to a thirteenth aspect of the present invention, in the sixth aspect, the parallax direction may be a direction from a first optical center of the first imaging optical system toward a second optical center of the second imaging optical system. The endoscope apparatus may include a light receiving surface disposed at the distal end and disposed at an image forming position of the first imaging optical system and the second imaging optical system. The bending control unit may include a virtual line calculation unit and a bending amount calculation unit. The virtual line calculation unit calculates a virtual line that passes through a position of a measurement point on the light receiving surface and the first optical center. The bending amount calculation unit calculates a bending amount necessary for moving the second optical center to a position on the virtual line or a position on an opposite side of the virtual line in the parallax direction.

According to a fourteenth aspect of the present invention, in the sixth aspect, the bending control unit may control the bending unit so that the distal end is bent by a predetermined bending amount. The measurement processing unit may include a measurement point searching unit. The measurement point searching unit processes at least a video signal corresponding to the first image after control of the bending unit based on the predetermined bending amount is performed, thereby searching for the same position as the position of the measurement point designated before the control of the bending unit based on the predetermined bending amount is performed and setting the measurement point at the position searched for. The reliability determination unit may determine the reliability again on the basis of the correspondence point corresponding to the measurement point searched for by the measurement point searching unit.

According to a fifteenth aspect of the present invention, an endoscope apparatus includes an endoscope insertion unit, a projection optical system, a pattern control unit, an imaging optical system, an imaging element, and a measurement processing unit. The projection optical system is disposed at a distal end of the endoscope insertion unit and sequentially projects a plurality of periodic patterns having different spatial phases on a subject. The pattern control unit shifts the spatial phase of the pattern. The imaging optical system is disposed at a position at the distal end different from a position at which the projection optical system is disposed and sequentially forms a plurality of optical images of the subject on which the plurality of patterns are projected. The imaging element generates a plurality of images corresponding to the plurality of optical images obtained via the imaging optical system. The measurement processing unit sets a measurement point in at least one of the plurality of images and calculates 3-dimensional coordinates of the measurement point by a phase shift method using the plurality of images. The endoscope apparatus further includes a reliability determination unit and a notification control unit. The reliability determination unit determines the reliability of a measurement process. The measurement process is performed on the basis of the measurement point. The notification control unit sends a notification to prompt a user to perform an operation of moving the distal end in a direction from the projection optical system toward the imaging optical system when the reliability determination unit determines that the reliability is low.

According to a sixteenth aspect of the present invention, an endoscope apparatus includes an endoscope insertion unit, a projection optical system, a pattern control unit, an imaging optical system, an imaging element, a measurement processing unit, and a bending unit. The projection optical system is disposed at a distal end of the endoscope insertion unit and sequentially projects a plurality of periodic patterns having different spatial phases on a subject. The pattern control unit shifts the spatial phase of the pattern. The imaging optical system is disposed at a position at the distal end different from a position at which the projection optical system is disposed and sequentially forms a plurality of optical images of the subject on which the plurality of patterns are projected. The imaging element generates a plurality of images corresponding to the plurality of optical images obtained via the imaging optical system. The measurement processing unit sets a measurement point in at least one of the plurality of images and calculates 3-dimensional coordinates of the measurement point by a phase shift method using the plurality of images. The bending unit is disposed in the distal end and bends the distal end. The endoscope apparatus further includes a reliability determination unit and a bending control unit. The reliability determination unit determines the reliability of a measurement process. The measurement process is performed on the basis of the measurement point. The bending control unit controls the bending unit so that the distal end is moved in a direction from the projection optical system toward the imaging optical system when the reliability determination unit determines that the reliability is low.

According to a seventeenth aspect of the present invention, an endoscope apparatus includes an endoscope insertion unit, a projection optical system, an imaging optical system, an imaging element, and a measurement processing unit. The projection optical system is disposed at a distal end of the endoscope insertion unit and projects a random pattern on a subject. The imaging optical system is disposed at a position at the distal end different from a position at which the projection optical system is disposed and forms an optical image of the subject on which the random pattern is projected. The imaging element generates a first image corresponding to an optical image obtained via the imaging optical system. The measurement processing unit includes a measurement point setting unit, a correspondence point searching unit, and a 3-dimensional coordinate calculation unit. The measurement point setting unit sets a measurement point in the first image. The correspondence point searching unit searches a second image of the random pattern for a correspondence point corresponding to the measurement point set by the measurement point setting unit. The 3-dimensional coordinate calculation unit calculates 3-dimensional coordinates of the measurement point by the principle of triangulation using the measurement point and the correspondence point searched for by the correspondence point searching unit. The endoscope apparatus may further include a reliability determination unit and a notification control unit. The reliability determination unit determines the reliability of a measurement process. The measurement process is performed on the basis of the measurement point. The notification control unit sends a notification to prompt a user to perform an operation of moving the distal end in a direction from the projection optical system toward the imaging optical system when the reliability determination unit determines that the reliability is low.

According to an eighteenth aspect of the present invention, an endoscope apparatus includes an endoscope insertion unit, a projection optical system, an imaging optical system, an imaging element, a measurement processing unit, and a bending unit. The projection optical system is disposed at a distal end of the endoscope insertion unit and projects a random pattern on a subject. The imaging optical system is disposed at a position at the distal end different from a position at which the projection optical system is disposed and forms an optical image of the subject on which the random pattern is projected. The imaging element generates a first image corresponding to the optical image obtained via the imaging optical system. The bending unit is disposed in the distal end and bends the distal end. The measurement processing unit includes a measurement point setting unit, a correspondence point searching unit, and a 3-dimensional coordinate calculation unit. The measurement point setting unit sets a measurement point in the first image. The correspondence point searching unit searches a second image of the random pattern for a correspondence point corresponding to the measurement point set by the measurement point setting unit. The 3-dimensional coordinate calculation unit calculates 3-dimensional coordinates of the measurement point by the principle of triangulation using the measurement point and the correspondence point searched for by the correspondence point searching unit. The endoscope apparatus further includes a reliability determination unit and a bending control unit. The reliability determination unit determines the reliability of a measurement process. The measurement process is performed on the basis of the measurement point. The bending control unit controls the bending unit so that the distal end is moved in a direction from the projection optical system toward the imaging optical system when the reliability determination unit determines that the reliability is low.

According to a nineteenth aspect of the present invention, an endoscope apparatus includes an endoscope insertion unit, an imaging optical system, an imaging element, and a measurement processing unit. The imaging optical system is disposed at a distal end of the endoscope insertion unit and forms an optical image of a subject at a first position and a second position different from the first position. The imaging element generates a first image corresponding to a first optical image obtained via the imaging optical system at the first position and a second image corresponding to a second optical image obtained via the imaging optical system at the second position. The measurement processing unit includes a measurement point setting unit, a correspondence point searching unit, and a 3-dimensional coordinate calculation unit. The measurement point setting unit sets a measurement point in the first image. The correspondence point searching unit searches the second image for a correspondence point corresponding to the measurement point set by the measurement point setting unit. The 3-dimensional coordinate calculation unit calculates 3-dimensional coordinates of the measurement point by the principle of triangulation using the measurement point and the correspondence point searched for by the correspondence point searching unit. The endoscope apparatus further includes a reliability determination unit and a notification control unit. The reliability determination unit determines the reliability of a measurement process. The measurement process is performed on the basis of the measurement point. The notification control unit sends a notification to prompt a user to perform an operation of moving the distal end in a direction from the second position toward the first position when the reliability determination unit determines that the reliability is low.

According to a twentieth aspect of the present invention, an endoscope apparatus includes an endoscope insertion unit, an imaging optical system, an imaging element, a measurement processing unit, and a bending unit. The imaging optical system is disposed at a distal end of the endoscope insertion unit and forms an optical image of a subject at a first position and a second position different from the first position. The imaging element generates a first image corresponding to a first optical image obtained via the imaging optical system at the first position and a second image corresponding to a second optical image obtained via the imaging optical system at the second position. The bending unit is disposed in the distal end and bends the distal end. The measurement processing unit includes a measurement point setting unit, a correspondence point searching unit, and a 3-dimensional coordinate calculation unit. The measurement point setting unit sets a measurement point in the first image. The correspondence point searching unit searches the second image for a correspondence point corresponding to the measurement point set by the measurement point setting unit. The 3-dimensional coordinate calculation unit calculates 3-dimensional coordinates of the measurement point by the principle of triangulation using the measurement point and the correspondence point searched for by the correspondence point searching unit. The endoscope apparatus further includes a reliability determination unit and a bending control unit. The reliability determination unit determines the reliability of a measurement process. The measurement process is performed on the basis of the measurement point. The bending control unit controls the bending unit so that the distal end is moved in a direction from the second position toward the first position when the reliability determination unit determines that the reliability is low.

According to a twenty-first aspect of the present invention, an endoscope apparatus includes an endoscope insertion unit, at least one imaging optical system, an imaging element, and a measurement processing unit. The at least one imaging optical system is disposed at a distal end of the endoscope insertion unit. The imaging element generates an image corresponding to an optical image obtained via the imaging optical system. The measurement processing unit performs a measurement process by the principle of triangulation on the basis of the image and camera parameters of a first position and a second position different from the first position. The endoscope apparatus further includes a reliability determination unit and a notification control unit. The reliability determination unit determines the reliability of the measurement process. The measurement process is performed on the basis of the measurement point set in the image corresponding to the optical image obtained via the imaging optical system at the first position. The notification control unit sends a notification to prompt a user to perform an operation of moving the distal end in a direction from the second position toward the first position when the reliability determination unit determines that the reliability is low.

According to a twenty-second aspect of the present invention, in the twenty-first aspect, the imaging optical system may include a first imaging optical system and a second imaging optical system. The first imaging optical system may be disposed at the first position. The second imaging optical system may be disposed at the second position and the second imaging optical system may have parallax with respect to the first imaging optical system. The image may include a first image corresponding to a first optical image obtained via the first imaging optical system and a second image corresponding to a second optical image obtained via the second imaging optical system. The measurement processing unit may perform the measurement process on the basis of the first image and the second image.

According to a twenty-third aspect of the present invention, in the twenty-first aspect, the imaging optical system may be disposed at the first position. The endoscope apparatus may include a projection optical system. The projection optical system may be disposed at the second position and projects a predetermined pattern on a subject.

According to a twenty-fourth aspect of the present invention, in the twenty-first aspect, the image may include a first image corresponding to a first optical image obtained via the imaging optical system at the first position and a second image corresponding to a second optical image obtained via the imaging optical system at the second position. The measurement processing unit may perform the measurement process on the basis of the first image and the second image.

According to a twenty-fifth aspect of the present invention, in the twenty-first aspect, the reliability determination unit may include an occlusion occurrence determination unit that determines whether or not occlusion has occurred. The reliability determination unit may determine that the reliability is low when the occlusion occurrence determination unit determines that occlusion has occurred.

According to a twenty-sixth aspect of the present invention, an endoscope apparatus includes an endoscope insertion unit, at least one imaging optical system, an imaging element, a measurement processing unit, and a bending unit. The at least one imaging optical system is disposed at a distal end of the endoscope insertion unit. The imaging element generates an image corresponding to an optical image obtained via the imaging optical system. The measurement processing unit performs a measurement process by the principle of triangulation on the basis of the image and camera parameters of a first position and a second position different from the first position. The bending unit is disposed in the distal end and bends the distal end. The endoscope apparatus further include a reliability determination unit and a bending control unit. The reliability determination unit determines the reliability of the measurement process. The measurement process is performed on the basis of the measurement point set in the image corresponding to the optical image obtained via the imaging optical system at the first position. The bending control unit controls the bending unit so that the distal end is moved in a direction from the second position toward the first position when the reliability determination unit determines that the reliability is low.

DETAILED DESCRIPTION OF THE INVENTION

Hereinafter, embodiments of the present invention will be described with reference to the drawings.

First Embodiment

Figure 1:
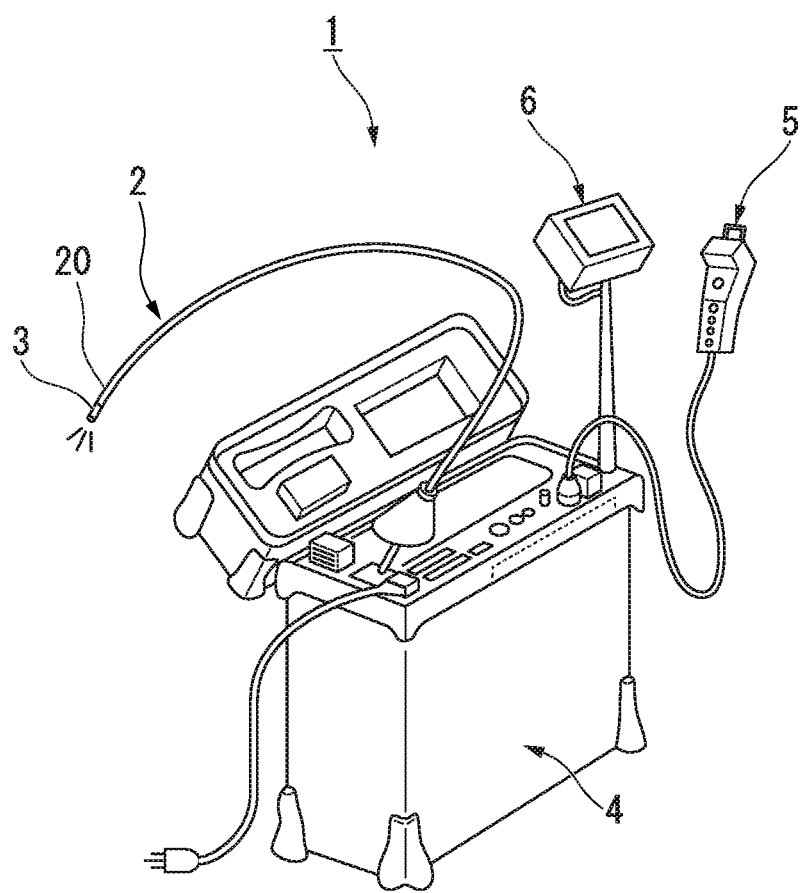
FIG. 1 is a perspective view of a measurement endoscope apparatus according to a first embodiment of the present invention.

FIG. 1 shows an external view of a measurement endoscope apparatus 1 according to a first embodiment of the present invention. The measurement endoscope apparatus 1 images a subject and measures geometric characteristics of the subject from the image. An examiner can replace an optical adapter attached to a distal end of an endoscope insertion unit, select a built-in measurement processing program, and add a measurement processing program in order to observe and measure various subjects.

As shown in FIG. 1, the measurement endoscope apparatus 1 includes an endoscope insertion unit 2, a stereo optical adapter 3 (a stereo optical system), a controller 4, an operating unit 5, and a display unit 6.

The endoscope insertion unit 2 is inserted into a subject. The endoscope insertion unit 2 has a narrow and long tubular form such that a portion extending from a distal end 20 to a base end can be bent. The endoscope insertion unit 2 images a measurement portion and outputs an imaging signal 100 (see FIG. 4) to the controller 4. The stereo optical adapter 3 is attached to the distal end 20 of the endoscope insertion unit 2.

The controller 4 controls the measurement endoscope apparatus 1. Control by the controller 4 includes video processing on video and arithmetic processing for measurement.

The operating unit 5 is a user interface. For example, the user interface is at least one of a button, a switch, a key, a mouse, a joystick, a touchpad, a trackball, and a touch panel. The operating unit 5 receives a user's operation on the measurement endoscope apparatus 1. The operating unit 5 is connected to the controller 4. For example, an operation that the operating unit 5 receives is at least one of first to eighth operations. The first operation relates to turning on and off of a power supply. The second operation relates to calibration setting. The third operation relates to an imaging operation. The fourth operation relates to illumination. The fifth operation relates to bending of the endoscope insertion unit 2. The sixth operation relates to measurement. The seventh operation relates to recording of video on a storage medium or the like. The eighth operation relates to reading of video recorded on a storage medium or the like. The user performs these operations via the operating unit 5.

The display unit 6 is a monitor (a display). The display unit 6 displays a video of a subject and other items of information on the basis of a display video signal 103 (see FIG. 4) output from the controller 4. These items of video and information are displayed independently as necessary. Alternatively, these items of video and information are displayed in combination. When stereo measurement is performed, the display video signal 103 includes at least one of two images having parallax.

Figure 4:
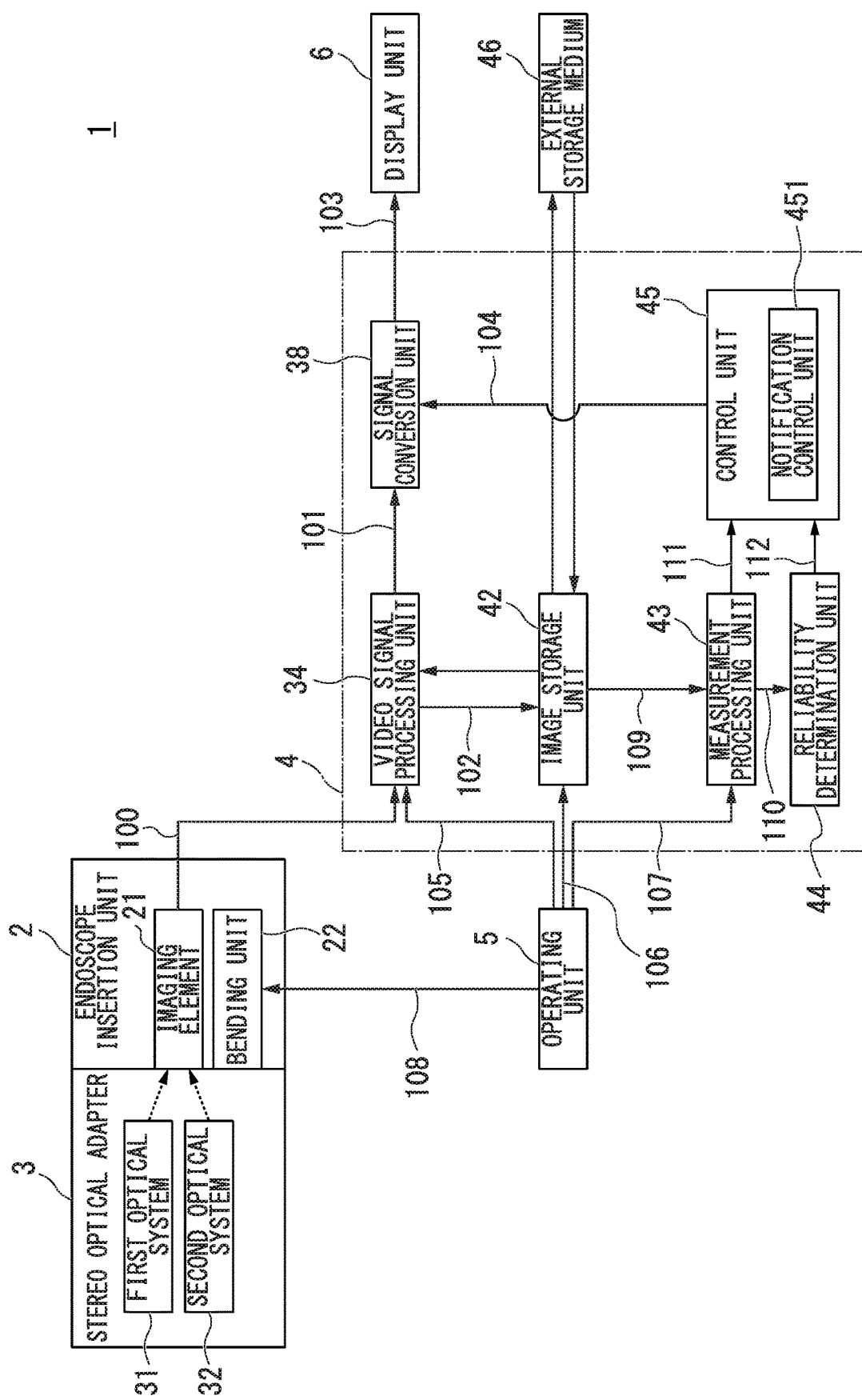
FIG. 4 is a block diagram showing a configuration of the measurement endoscope apparatus according to the first embodiment of the present invention.

For example, information other than video displayed by the display unit 5 is at least one of operation input information input from the operating unit 5, an operation menu, an operation graphical user interface (GUI), and measurement information 104 (see FIG. 4). The measurement information 104 is an alignment image used during measurement, a measurement result, and the like.

Figure 2:
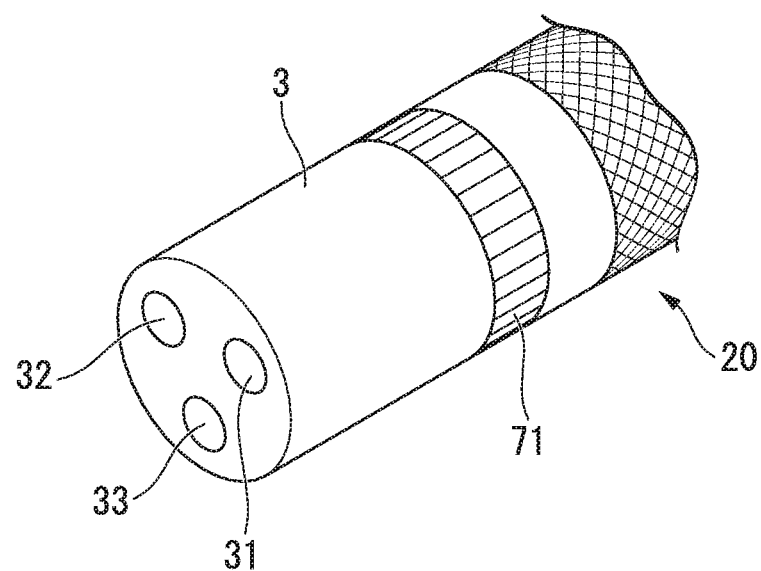
FIG. 2 is a perspective view showing a configuration of a distal end of an endoscope insertion unit and a stereo optical adapter of the measurement endoscope apparatus according to the first embodiment of the present invention.
Figure 3:
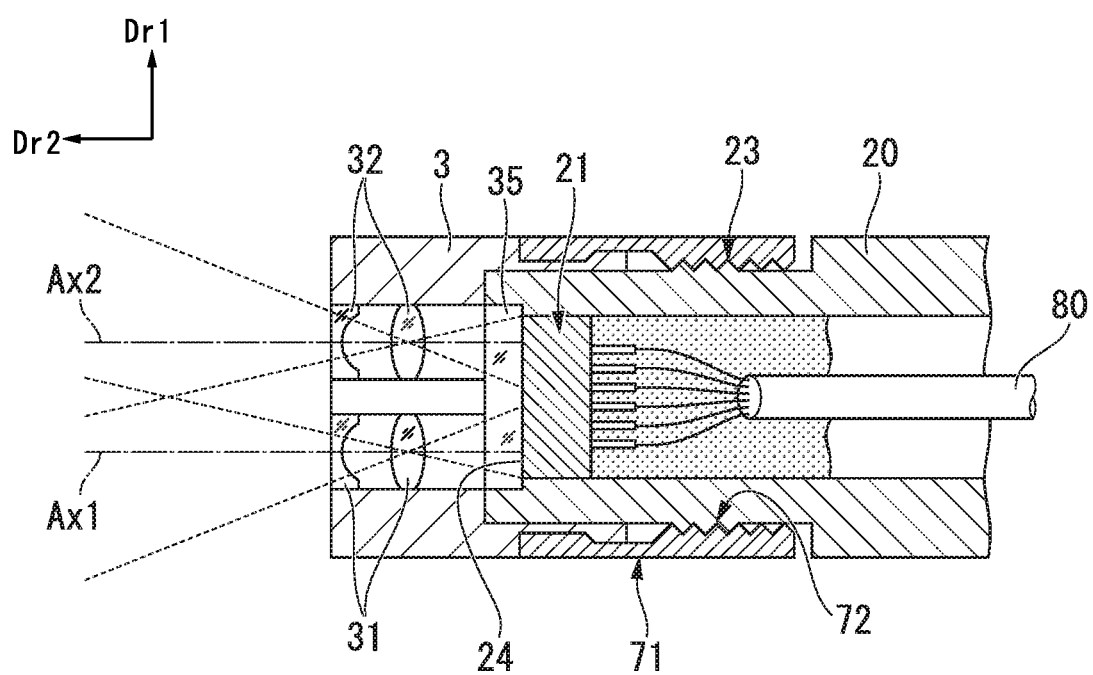
FIG. 3 is a cross-sectional view showing a configuration of the distal end of the endoscope insertion unit and the stereo optical adapter of the measurement endoscope apparatus according to the first embodiment of the present invention.

FIGS. 2 and 3 show a configuration of the stereo optical adapter 3 and the distal end 20 of the endoscope insertion unit 2. FIG. 2 shows an external view of the stereo optical adapter 3 and the distal end 20 of the endoscope insertion unit 2. FIG. 3 shows a cross-section of the stereo optical adapter 3 and the distal end 20 of the endoscope insertion unit 2. FIG. 3 shows a cross-section including a first optical system 31 and a second optical system 32.

The stereo optical adapter 3 is attached to the distal end 20 of the endoscope insertion unit 2. The stereo optical adapter 3 is screwed and fixed to a male screw 23 of the distal end 20 of the endoscope insertion unit 2 by a female screw 72 of a fixing ring 71. The first optical system 31, the second optical system 32, and an illumination window 33 are provided in the distal end of the stereo optical adapter 3. The first optical system 31 and the second optical system 32 include an objective lens. The first optical system 31 and the second optical system 32 are separated from each other in a parallax direction Dr1. The first optical system 31 is disposed on the left side when facing the subject and the second optical system 32 is disposed on the right side. An optical axis Ax1 of the first optical system 31 and an optical axis Ax2 of the second optical system 32 are disposed in a direction Dr2 crossing the parallax direction Dr1. That is, the optical axis Ax1 of the first optical system 31 and the optical axis Ax2 of the second optical system 32 are disposed to face the direction Dr2. The parallax direction Dr1 is the direction of a straight line that passes through the first optical center (a principal point) of the first optical system 31 and the second optical center (a principal point) of the second optical system 32. The direction Dr2 is orthogonal to the parallax direction Dr1. The first optical system 31 and the second optical system 32 form two images of the subject on an imaging element 21 provided in the distal end 20 of the endoscope insertion unit 2. The first optical system 31 forms a first optical image and the second optical system 32 forms a second optical image.

The first optical image and the second optical image have parallax. A measurement point is designated in a first image corresponding to the first optical image. The first optical system 31 may be disposed on the right side when facing the subject and the second optical system 32 may be disposed on the left side.

The imaging element 21 is an image sensor. The imaging element 21 is disposed in the distal end 20 of the endoscope insertion unit 2. The imaging element 21 has a light receiving surface 24 disposed at the image forming positions of the first optical system 31 and the second optical system 32. The imaging element 21 generates an imaging signal 100 from at least one of the first optical image formed on the light receiving surface 24 via the first optical system 31 and the second optical image formed on the light receiving surface 24 via the second optical system 32. That is, the imaging element 21 generates the first image corresponding to the first optical image obtained via the first optical system 31 and the second image corresponding to the second optical image obtained via the second optical system 32.

The imaging element 21 is connected to a signal line 80 and the imaging signal 100 is output from the imaging element 21 to the signal line 80. A cover glass 35 for protecting the imaging element 21 is disposed on an end surface of the distal end 20 of the endoscope insertion unit 2.

FIG. 4 shows a configuration of the measurement endoscope apparatus 1. As shown in FIG. 4, the stereo optical adapter 3 includes the first optical system 31 and the second optical system 32. The optical axes of the first optical system 31 and the second optical system 32 are disposed in a direction crossing the parallax direction. The stereo optical adapter 3 is disposed at the distal end 20 of the endoscope insertion unit 2. At the distal end 20 of the endoscope insertion unit 2, the first optical system 31 and the second optical system 32 are disposed to be separated from each other in the parallax direction. In the configuration shown in FIG. 4, the stereo optical adapter 3 is disposed near the distal end 20 of the endoscope insertion unit 2. The first optical system 31 and the second optical system 32 that constitute the stereo optical adapter 3 may be disposed inside the distal end 20 of the endoscope insertion unit 2.

The endoscope insertion unit 2 has the imaging element 21 and a bending unit 22. The imaging element 21 outputs the imaging signal 100 based on the first optical image and the second optical image. Alternatively, the imaging element 21 outputs the imaging signal 100 based on the first optical image only and the imaging signal 100 based on the second optical image only. The bending unit 22 is a bending mechanism. The bending unit 22 is disposed in the distal end 20 of the endoscope insertion unit 2. The bending unit 22 bends the distal end 20 of the endoscope insertion unit 2.

The operating unit 5 receives an operation instruction related to stereo measurement with respect to an image (the first image) displayed on the display unit 6 and a bending instruction for bending the distal end 20 of the endoscope insertion unit 2 from the user. The operation instruction related to stereo measurement includes an instruction to start and end measurement, an instruction to record an image, and a measurement point instruction. When the operating unit 5 receives an instruction to start measurement from the user, the operating unit 5 outputs a measurement start signal 105. When the operating unit 5 receives an instruction to record an image, the operating unit 5 outputs an image record instruction signal 106. When the operating unit 5 receives a measurement point instruction, the operating unit 5 outputs measurement input information 107. When the operating unit 5 receives a bending instruction, the operating unit 5 outputs a bending instruction signal 108.

The controller 4 includes a video signal processing unit 34, a signal conversion unit 38, an image storage unit 42, a measurement processing unit 43, a reliability determination unit 44, and a control unit 45.

The video signal processing unit 34 and the signal conversion unit 38 are signal processing circuits. After the measurement start signal 105 is input, the video signal processing unit 34 performs video processing on the imaging signal 100. In this way, the video signal processing unit 34 generates an output video signal 101 and an output video signal 102 corresponding to at least one of the first image based on the first optical image and the second image based on the second optical image from the imaging signal 100. When the imaging signal 100 based on the first and second optical images is output from the imaging element 21, the video signal processing unit 34 generates the output video signals 101 and 102 corresponding to the first and second images. When the imaging signal 100 based on the first or second optical image only is output from the imaging element 21, the video signal processing unit 34 combines the imaging signal 100 based on the first image only and the imaging signal 100 based on the second image only. In this way, the video signal processing unit 34 generates the output video signals 101 and 102 corresponding to the first and second images. The video signal processing unit 34 may generate the output video signals 101 and 102 corresponding to the first image only. The output video signal 101 is output to the signal conversion unit 38. The output video signal 102 is output to the image storage unit 42. The output video signals 101 and 102 need not be limited to being different signals. The output video signals 101 and 102 may be the same signal on which the same video processing is performed.

The signal conversion unit 38 outputs the output video signal 101 output from the video signal processing unit 34 to the display unit 6 as a display video signal 103. The signal conversion unit 38 converts the output video signal 101 to the display video signal 103 by combining other image data such as an operation screen image with the output video signal 101 as necessary. Moreover, when the measurement information 104 is output from the control unit 45, the signal conversion unit 38 generates the display video signal 103 by combining the measurement information 104 with the output video signal 101.

The user designates a measurement point or the like by operating an alignment on the screen of the display unit 6 via the operating unit 5. Information on the measurement point or the like is output to the measurement processing unit 43 as the measurement input information 107. The measurement result of the stereo measurement is output to the signal conversion unit 38 as the measurement information 104 together with a measurement GUI image including a mark of the measurement point or the like. The measurement information 104 is combined with the output video signal 101 by the signal conversion unit 38.

The display unit 6 displays at least the first image on the basis of at least the display video signal 103 corresponding to the first image. Since the display video signal 103 corresponds to the first and second images, the display unit 6 displays the first and second images. When the display video signal 103 corresponds to the first image only, the display unit 6 displays the first image.

The image storage unit 42 is a volatile or nonvolatile memory. For example, the memory is at least one of a random access memory (RAM), a dynamic random access memory (DRAM), a static random access memory (SRAM), a read only memory (ROM), an erasable programmable read only memory (EPROM), an electrically erasable programmable read-only memory (EEPROM), and a flash memory. The image storage unit 42 stores the output video signal 102 output from the video signal processing unit 34. The output video signal 102 stored in the image storage unit 42 is one frame of still-image data or a plurality of frames of live image data (moving image data). When the image record instruction signal 106 is input from the operating unit 5, the image data is read from the image storage unit 42 according to the control by the control unit 45. The read image data is output to an external storage medium 46 and is stored in the external storage medium 46. Moreover, the image data stored in the image storage unit 42 is output to the measurement processing unit 43 as image data 109.

The measurement processing unit 43, the reliability determination unit 44, and the control unit 45 are configured as one or a plurality of processors. For example, the processor is at least one of a central processing unit (CPU), a digital signal processor (DSP), and a graphics processing unit (GPU). The measurement processing unit 43, the reliability determination unit 44, and the control unit 45 may be configured as an application specific integrated circuit (ASIC) or a field-programmable gate array (FPGA).

The measurement processing unit 43 performs a measurement process using the image data 109 output from the image storage unit 42. Moreover, the measurement processing unit 43 generates a measurement GUI image necessary for the user's measurement operation. The measurement processing unit 43 performs stereo measurement according to a known algorithm.

Figure 5:
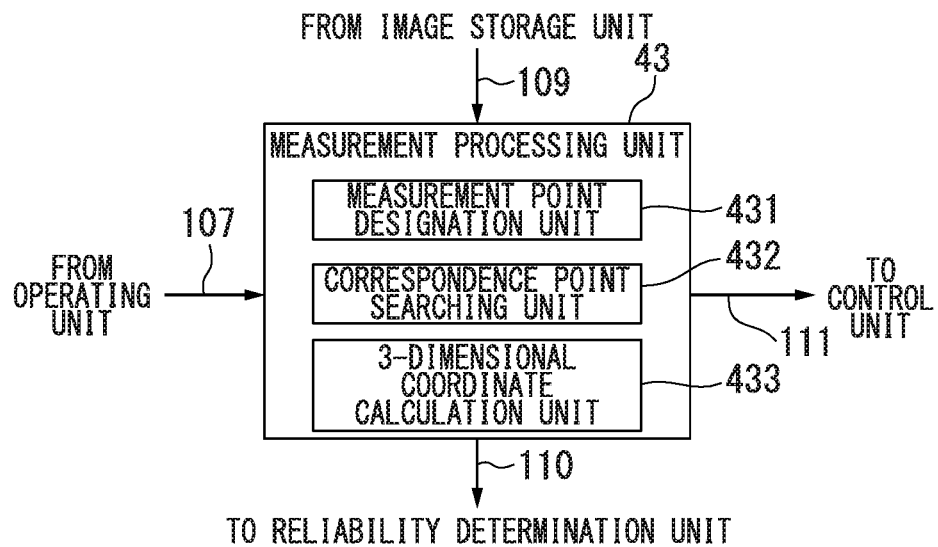
FIG. 5 is a block diagram showing a configuration of a measurement processing unit of the measurement endoscope apparatus according to the first embodiment of the present invention.

FIG. 5 shows a configuration of the measurement processing unit 43. As shown in FIG. 5, the measurement processing unit 43 includes a measurement point designation unit 431 (a measurement point setting unit), a correspondence point searching unit 432, and a 3-dimensional coordinate calculation unit 433.

The measurement point designation unit 431 designates a measurement point of the first image on the basis of the operation instruction received by the operating unit 5. That is, the measurement point designation unit 431 designates a measurement point on the basis of the measurement input information 107 from the operating unit 5. In other words, the measurement point designation unit 431 sets a measurement point of the first image corresponding to the first optical image obtained via the first optical system 31. The correspondence point searching unit 432 searches for a correspondence point of the second image corresponding to the measurement point by processing at least a video signal (the image data 109) corresponding to the first image and a video signal (the image data 109) corresponding to the second image. That is, the correspondence point searching unit 432 searches for the correspondence point by performing pattern matching between the first and second images. In other words, the correspondence point searching unit 432 searches the second image corresponding to the second optical image obtained via the second optical system 32 for a correspondence point corresponding to the measurement point set by the measurement point designation unit 431. The 3-dimensional coordinate calculation unit 433 calculates 3-dimensional coordinates of the measurement point by the principle of triangulation using the measurement point and the correspondence point searched for (specified) by the correspondence point searching unit 432.

The processing of at least the video signal corresponding to the first image and the video signal corresponding to the second image includes processing of a video signal of a portion corresponding to the first image and processing of a video signal of a portion corresponding to the second image, of the video signals corresponding to the first and second images. Alternatively, the processing of at least the video signal corresponding to the first image and the video signal corresponding to the second image includes processing of a video signal corresponding to the first image only and processing of a video signal corresponding to the second image only.

The measurement point is a point on the first image. The 3-dimensional coordinates of the measurement point are 3-dimensional coordinates of a spatial point on the subject corresponding to the measurement point. Similarly, the 3-dimensional coordinates of a point on the first image are 3-dimensional coordinates of a spatial point on the subject corresponding to the point.

The measurement processing unit 43 calculates a distance, an area, and the like regarding the dimensions of the subject on the basis of the 3-dimensional coordinates calculated by the 3-dimensional coordinate calculation unit 433. The measurement processing unit 43 outputs measurement information 110 such as correspondence point information to the reliability determination unit 44. Moreover, the measurement processing unit 43 outputs measurement result information 111 indicating the measurement result to the control unit 45.

The reliability determination unit 44 determines the reliability of the correspondence point searched for (specified) by the correspondence point searching unit 432. In other words, the reliability determination unit 44 determines the reliability of the measurement process. The measurement process is performed on the basis of the measurement point. The reliability determination unit 44 outputs determination result information 112 indicating the reliability determination result to the control unit 45.

The control unit 45 controls the respective units of the measurement endoscope apparatus 1. The control unit 45 has a notification control unit 451. The notification control unit 451 sends a notification to prompt a user to perform a bending operation of bending the distal end 20 of the endoscope insertion unit 2 so that the distal end 20 of the endoscope insertion unit 2 moves toward the first optical system 31 in the parallax direction when the reliability determination unit 44 determines that the reliability is low. In other words, the notification control unit 451 sends a notification to prompt a user to move the distal end 20 of the endoscope insertion unit 2 toward the first optical system 31 in the parallax direction when the reliability determination unit 44 determines that the reliability is low. That is, the notification control unit 451 outputs measurement information 104 including a message that prompts the user to perform a bending operation.

A measurement point is designated in the first image based on the first optical image formed via the first optical system 31. In this case, the measurement point is a point on the subject that can be observed in the first image. When occlusion occurs, a correspondence point of the second image corresponding to the measurement point may be included in a blind area. In this case, when the viewpoint is moved toward the first optical system (that is, toward the left side), it is expected that the user will be able to observe the correspondence point. Due to this, it is possible to suppress a decrease in measurement accuracy due to the occurrence of occlusion.

When occlusion occurs, a bending operation is performed to move the viewpoint. The direction in which the distal end 20 of the endoscope insertion unit 2 is bent can be predicted from a geometric relation. When the measurement point is designated in the first image, the direction of moving the viewpoint to avoid occlusion is the direction from the second optical system 32 to the first optical system 31. That is, the direction of moving the viewpoint is the leftward direction. When the first optical system 31 is disposed on the right side of the second optical system 32, the direction of moving the viewpoint is the rightward direction.

Figure 6:
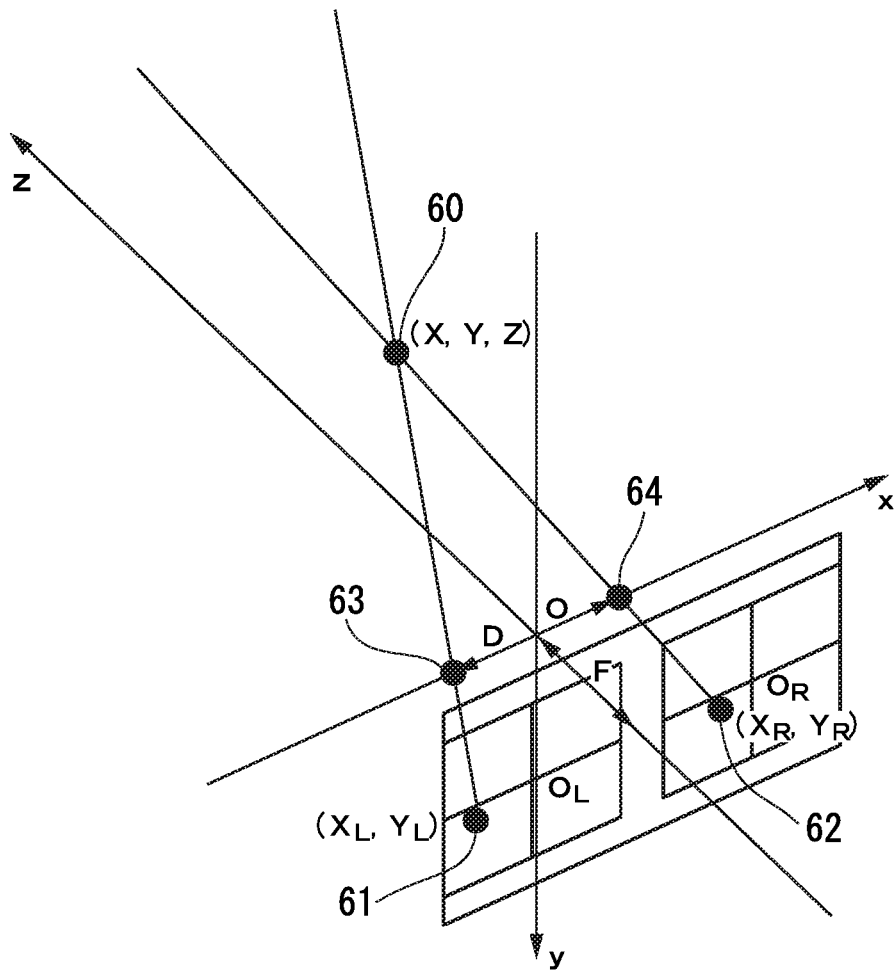
FIG. 6 is a reference diagram showing a method of calculating 3-dimensional coordinates of a measurement point by stereo measurement according to the first embodiment of the present invention.

The principle of stereo measurement will be described with reference to FIG. 6. In stereo measurement, a subject image can be measured by calculating the 3-dimensional coordinates of a subject by the principle of triangulation on the basis of the coordinates of two optical distance measurement points when the subject image is observed by two optical systems. Hereinafter, a method of calculating the 3-dimensional coordinates of a measurement point using stereo measurement will be described. A midpoint of a line segment connecting the left optical center (a first optical center 63) and the right optical center (a second optical center 64) is defined as the origin O. Moreover, an x-axis of which the positive direction is the rightward direction and a y-axis of which the positive direction is the downward direction are defined. The x-axis is a straight line that passes through the left optical center (the first optical center 63) and the right optical center (the second optical center 64). Moreover, a z-axis of which the positive direction is the direction away from the optical system parallel to the optical axis is defined.

The 3-dimensional coordinates (X,Y,Z) of a measurement point 60 are calculated according to the following equations (1) to (3) according to a method of triangulation with respect to an image including a subject image obtained via the left optical system (the first optical system 31) and the right optical system (the second optical system 32). The 2-dimensional coordinates of a measurement point 61 of a left image surface on which distortion correction is performed and a correspondence point 62 of a right image surface on which distortion correction is performed are (XL,YL) and (XR, YR), respectively. The origins for these two 2-dimensional coordinates are intersection points OL and OR between the image surface and the optical axes of the left and right optical systems. The distance between the first optical center 63 and the second optical center 64 is D. A focal length is F. t satisfies t=D/(XR−XL).

$$X = t \times XR + D/2 \tag{1}$$

$$Y = -t \times YR \tag{2}$$

$$Z = t \times F \tag{3}$$

When the coordinates of the measurement point 61 and the correspondence point 62 on the image surface are determined in the above-described manner, the 3-dimensional coordinates of the measurement point 60 are calculated using the parameters D and F. By calculating the 3-dimensional coordinates of several points, various measurements such as the distance between two points, the distance between one point and a line connecting two points, an area, a depth, and a surface shape can be obtained. Moreover, it is also possible to calculate the distance (an object distance) from the first optical center 63 or the second optical center 64 to the subject. In order to perform the stereo measurement, optical data indicating the characteristics of an optical system including the distal end 20 of the endoscope insertion unit 2 and the stereo optical adapter 3 is necessary. For example, since the details of a matching process and the optical data are disclosed in Japanese Unexamined Patent Application, First Publication No. 2004-49638, a description thereof will be omitted.

The optical data is general camera parameters. The camera parameters include the parameter D of a first position and a second position different from the first position. The first position is the first optical center 63 and the second position is the second optical center 64. The coordinates of the first position are (x,y,z)=(−D/2,0,0) and the coordinates of the second position are (x,y,z)=(D/2,0,0). The measurement processing unit 43 performs a measurement process by the principle of triangulation on the basis of an image generated by the imaging element 21 and the camera parameters of the first position and the second position different from the first position. Here, the camera parameters include the parameter D, and the parameter D is the distance D between the first and second positions. The notification control unit 451 sends a notification to prompt the user to move the distal end 20 of the endoscope insertion unit 2 in a direction from the second position toward the first position when the reliability determination unit 44 determines that the reliability is low.

Figure 7:
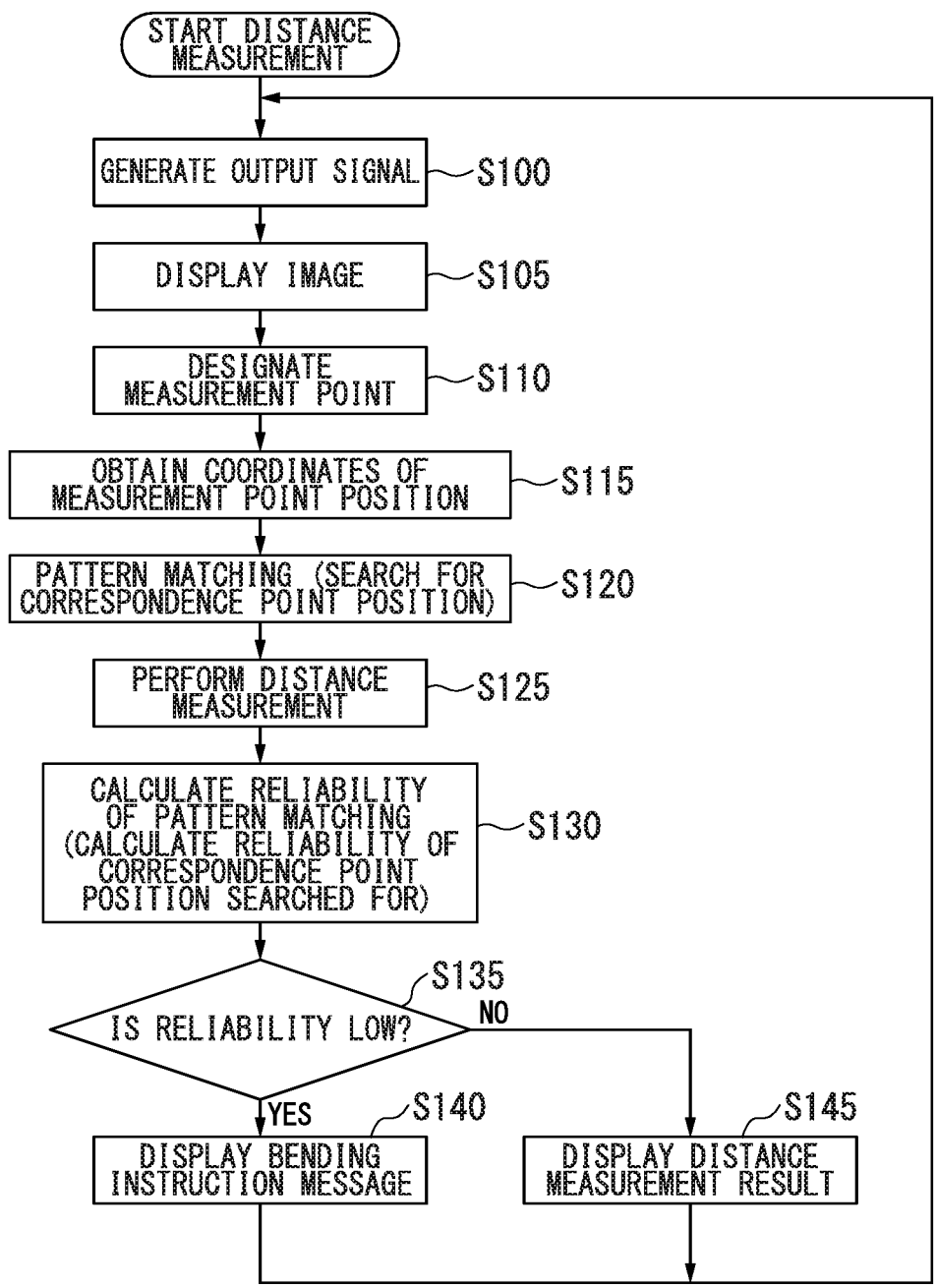
FIG. 7 is a flowchart showing the procedure of an operation of the measurement endoscope apparatus according to the first embodiment of the present invention.

The operation of the measurement endoscope apparatus 1 will be described. FIG. 7 shows the procedure of an operation of the measurement endoscope apparatus 1 during distance measurement. Distance measurement is performed in a state in which a live image of a subject is displayed. In the distance measurement, the object distance to a subject is measured. The imaging element 21 generates the imaging signal 100 continuously. That is, the imaging element 21 generates the imaging signals 100 of the respective frames of the live image.

After distance measurement starts, the video signal processing unit 34 generates the output video signal 101 and the output video signal 102 from the imaging signal 100. The signal conversion unit 38 outputs the display video signal 103 based on the output video signal 101 to the display unit 6 (step S100). After step S100 is performed, the display unit 6 displays an image on the basis of the display video signal 103 (step S105).

Figure 8:
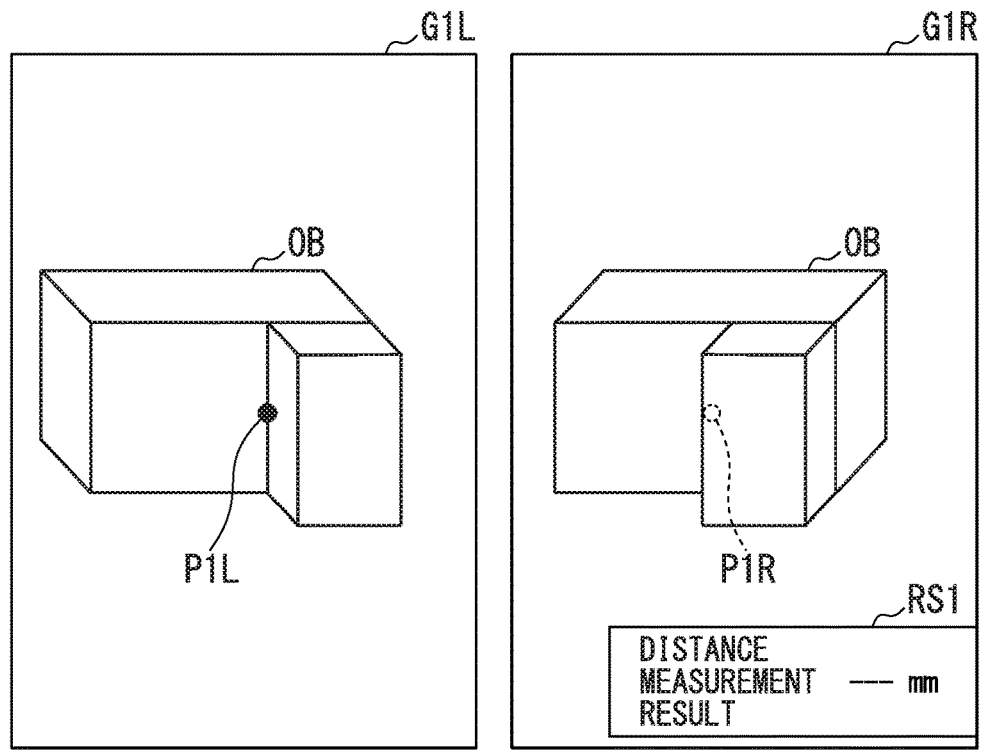
FIG. 8 is a reference diagram showing an image displayed by a display unit of the measurement endoscope apparatus according to the first embodiment of the present invention.

FIG. 8 shows an example of an image displayed by the display unit 6. The display unit 6 displays a first image G1L and a second image G1R. The first image G1L is based on the first optical image formed via the first optical system 31. The second image G1R is based on the second optical image formed via the second optical system 32. A subject OB appears in the first and second images G1L and G1R. A distance measurement result RS1 which is a measurement result for the object distance is superimposed on the second image G1R. An alignment mark is superimposed on the first image G1L. The alignment mark is omitted in FIG. 8.

After step S105 is performed, the user designates a measurement point via the operating unit 5. The operating unit 5 outputs the measurement input information 107 (step S110). The measurement input information 107 includes position information of an alignment mark designated by the user. After step S110 is performed, the measurement point designation unit 431 designates a measurement point of the first image on the basis of the measurement input information 107 from the operating unit 5. In this way, the measurement point designation unit 431 sets the measurement point of the first image. That is, the measurement point designation unit 431 obtains the 2-dimensional coordinates of the position of the measurement point (step S115). For example, the position of the alignment mark and the position of the measurement point are identical.

After step S115 is performed, the correspondence point searching unit 432 performs pattern matching between template image data and the image data 109 corresponding to the second image and searches for a correspondence point of the second image corresponding to the measurement point (step S120). The template image data is a predetermined size of data including the position of the measurement point, of the image data 109 corresponding to the first image. The correspondence point searching unit 432 performs pattern matching by shifting the position of a region of the second image to be compared with the template image data. After the correspondence point is searched for, the correspondence point searching unit 432 outputs the measurement information 110 including the position information of the measurement point and the correspondence point to the reliability determination unit 44.

After step S120 is performed, the third 3-dimensional coordinate calculation unit 433 performs a distance measurement process (step S125). In step S125, the 3-dimensional coordinate calculation unit 433 calculates the 3-dimensional coordinates of the measurement point by the principle of triangulation using the measurement point and the correspondence point searched for by the correspondence point searching unit 432. The value of a Z-coordinate of the measurement point 60 shown in FIG. 6 is an object distance. That is, the 3-dimensional coordinate calculation unit 433 calculates an object distance by calculating the 3-dimensional coordinates of the measurement point. The 3-dimensional coordinate calculation unit 433 outputs the measurement result information 111 including the calculated object distance to the control unit 45.

FIG. 8 shows an image in a state in which occlusion occurs. A measurement point P1L is designated in the region of the subject OB in the first image G1L. The distance from the distal end 20 of the endoscope insertion unit 2 to the subject OB is different depending on the region of the subject OB. That is, the subject OB has a step. The measurement point P1L is designated on a region having a step. In the second image G1R, a correspondence point P1R corresponding to the measurement point P1L is included in a blind area generated due to a step on the surface of the subject OB. Due to this, in the second image G1R, it is not possible to observe the correspondence point P1R corresponding to the measurement point P1L. When the measurement point P1L is designated, the correspondence point searching unit 432 searches for a correspondence point. Since the correspondence point P1R corresponding to the measurement point P1L cannot be observed in the second image G1R, the correspondence point searching unit 432 may search for a wrong correspondence point. However, when the viewpoint is moved to the left side, it is expected that the correspondence point P1R can be observed in the second image G1R.

After step S125 is performed, the reliability determination unit 44 calculates the reliability of pattern matching on the basis of the measurement information 110 (step S130). After step S130 is performed, the reliability determination unit 44 determines whether or not the reliability calculated in step S130 is low (step S135). Through steps S130 and S135, the reliability determination unit 44 determines the reliability. The reliability determination unit 44 outputs the determination result information 112 to the control unit 45.

When it is determined in step S135 that the reliability is low, the notification control unit 451 outputs the measurement information 104 including a message that prompts the user to perform a bending operation of bending the distal end 20 of the endoscope insertion unit 2 so that the distal end 20 of the endoscope insertion unit 2 is moved toward the first optical system 31 in the parallax direction. In this way, the notification control unit 451 outputs a notification to prompt the user to perform the bending operation. The signal conversion unit 38 generates the display video signal 103 by combining the measurement information 104 with the output video signal 101. The display unit 6 displays an image including the message on the basis of the display video signal 103 (step S140). After step S140 is performed, the process of step S100 is performed.

Figure 9:
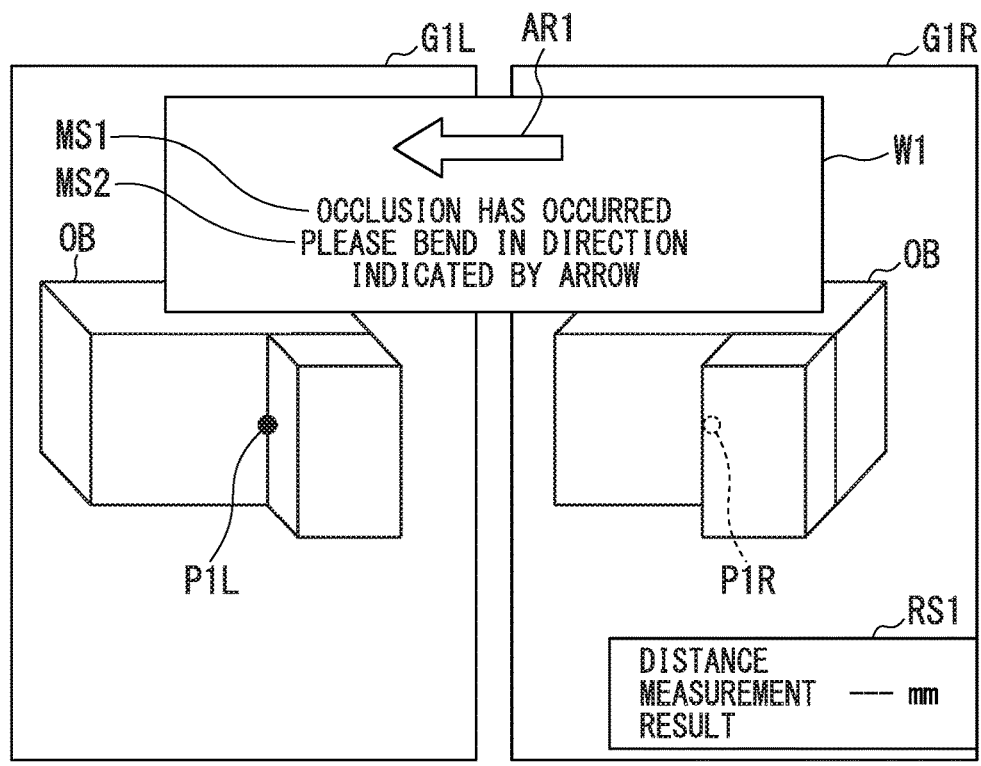
FIG. 9 is a reference diagram showing an image displayed by the display unit of the measurement endoscope apparatus according to the first embodiment of the present invention.

FIG. 9 shows an example of an image displayed by the display unit 6 in step S140. The difference between FIGS. 8 and 9 will be described. The display unit 6 displays a message window W1. The message window W1 includes a message MS1 indicating the occurrence of occlusion and a message MS2 for prompting the user to perform a bending operation. Moreover, the message window W1 includes an arrow AR1 indicating the direction of the bending operation. The arrow AR1 indicates the leftward direction. The direction indicated by the arrow AR1 is the direction from the second optical system 32 toward the first optical system 31. Since the message MS2 and the arrow AR1 are displayed, the user can understand that the distal end 20 of the endoscope insertion unit 2 should be bent toward the left side in order to avoid the occlusion. The user can bend the distal end 20 of the endoscope insertion unit 2 by operating the operating unit 5 according to the displayed message. As a result, the user can designate the measurement point at a position where occlusion does not occur. Aspects other than the above-described aspect of the image shown in FIG. 9 are the same as those of the image shown in FIG. 8.

When it is determined in step S135 that the reliability is high, the notification control unit 451 outputs the measurement information 104 including the distance measurement result. In this way, the notification control unit 451 notifies the user of the distance measurement result. The signal conversion unit 38 generates the display video signal 103 by combining the measurement information 104 with the output video signal 101. The display unit 6 displays an image including the distance measurement result on the basis of the display video signal 103 (step S145). When an image including a distance measurement result for an image of the previous frame is displayed immediately before the process of step S145 is performed, an image including the updated distance measurement result is displayed in step S145. Since the distance measurement result is displayed, the user can understand a highly accurate measurement result. After step S145 is performed, the process of step S100 is performed.

In step S140, a message indicating the direction of bending the distal end 20 of the endoscope insertion unit 2 only may be displayed. Alternatively, a mark (an arrow or the like) indicating the direction of bending the distal end 20 of the endoscope insertion unit 2 only may be displayed. The notification to the user may be performed by means other than the display unit 6. For example, when the measurement endoscope apparatus 1 has an audio output function, the measurement endoscope apparatus 1 may send a notification to the user by outputting an audio.

Distance measurement may be performed only when the reliability is high. For example, after the process of step S120 is performed, the process of step S130 may be performed. When it is determined in step S135 that the reliability is high, the process of step S125 may be performed.

As described above, the measurement endoscope apparatus 1 notifies the user of the occurrence of occlusion and a method of avoiding occlusion when occlusion occurs. In this way, the user can understand that measurement cannot be performed correctly due to the occurrence of occlusion. Moreover, the user can understand which bending operation is necessary to avoid occlusion.

When the measurement point is designated in the first image, the moving direction of the distal end 20 of the endoscope insertion unit 2 is the direction from the second optical center 64 of the second optical system 32 toward the first optical center 63 of the first optical system 31. The moving direction of the distal end 20 of the endoscope insertion unit 2 may not be perfectly identical to this direction. The moving direction of the distal end 20 of the endoscope insertion unit 2 has only to be such a direction that the second optical system 32 approaches the position of the first optical system 31 before the distal end 20 of the endoscope insertion unit 2 moves.

Figure 10:
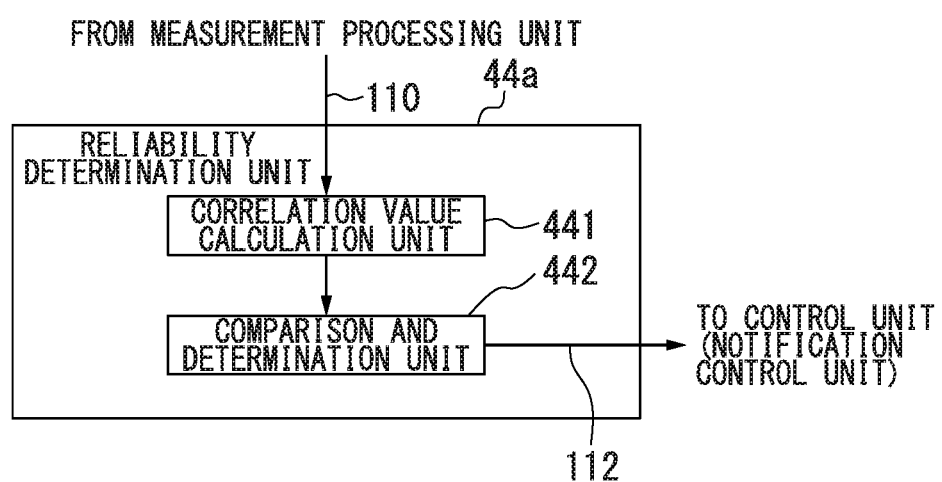
FIG. 10 is a block diagram showing a configuration of a reliability determination unit of the measurement endoscope apparatus according to the first embodiment of the present invention.

A detailed configuration of the reliability determination unit 44 will be described. FIG. 10 shows a configuration of a reliability determination unit 44a which is a first example of the reliability determination unit 44. As shown in FIG. 10, the reliability determination unit 44a includes a correlation value calculation unit 441 and a comparison and determination unit 442.

The correlation value calculation unit 441 calculates a correlation value or a degree of difference between the position of the measurement point in the first image and the position of the correspondence point in the second image. The comparison and determination unit 442 compares the correlation value or the degree of difference with a first predetermined value and determines the reliability on the basis of the comparison result. For example, the comparison and determination unit 442 compares the correlation value with the first predetermined value and determines that the reliability is low when the correlation value is smaller than the first predetermined value. Alternatively, the comparison and determination unit 442 compares the degree of difference with the first predetermined value and determines that the reliability is low when the degree of difference is larger than the first predetermined value.

Figure 11:
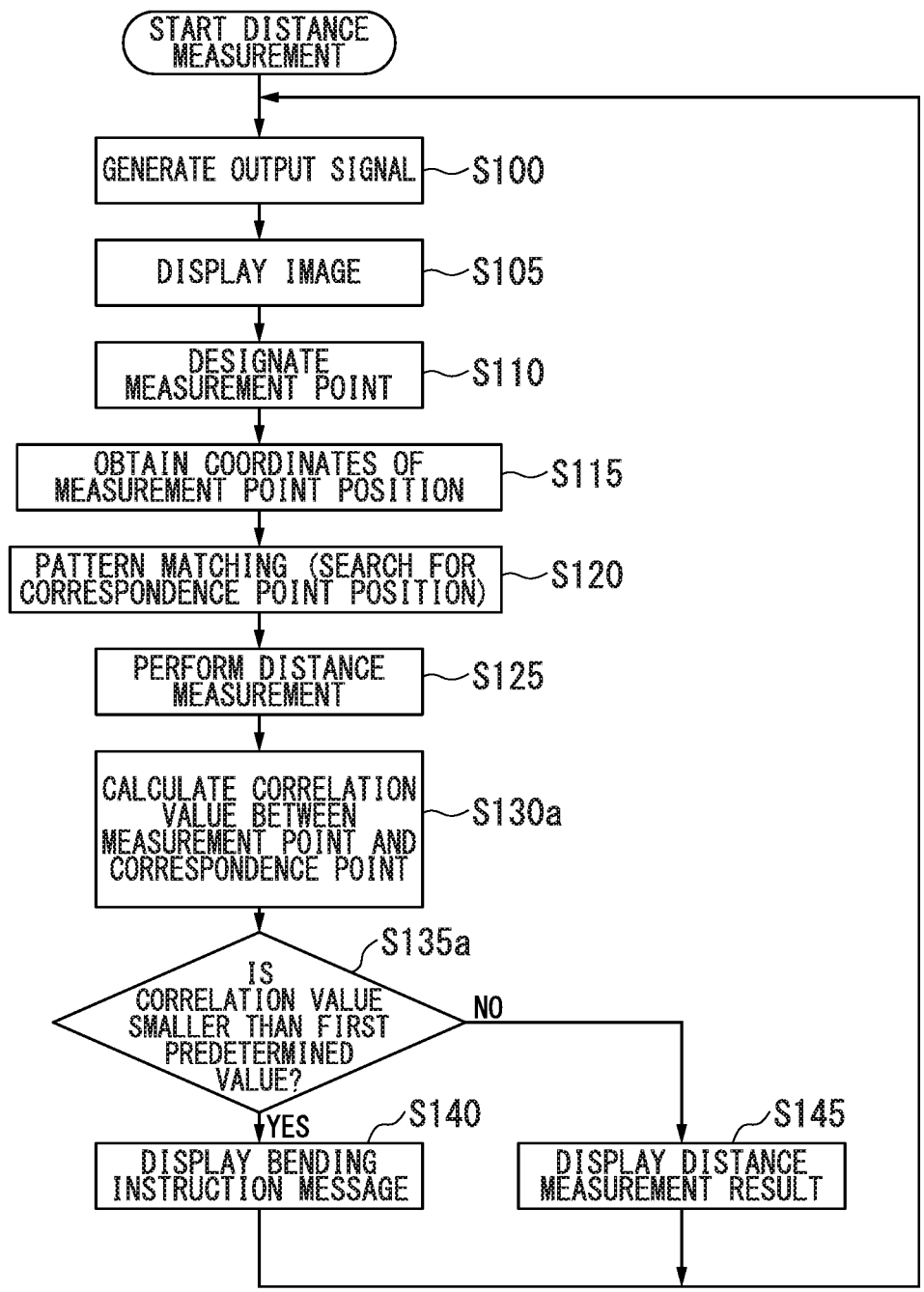
FIG. 11 is a flowchart showing the procedure of an operation of the measurement endoscope apparatus according to the first embodiment of the present invention.

FIG. 11 shows the procedure of an operation of the measurement endoscope apparatus 1 during distance measurement. When the measurement endoscope apparatus 1 has the reliability determination unit 44a, the measurement endoscope apparatus 1 performs a process shown in FIG. 11. The difference between FIGS. 7 and 11 will be described.

After step S125 is performed, the correlation value calculation unit 441 calculates a correlation value between the position of the measurement point in the first image and the position of the correspondence point in the second image on the basis of the measurement information 110 from the measurement processing unit 43 (step S130a). Step S130a corresponds to step S130 in FIG. 7. The measurement information 110 includes position information of the measurement point and the correspondence point. Moreover, the measurement information 110 includes image data of a region including the position of the measurement point in the first image and image data of a region including the position of the correspondence point in the second image. The correlation value is a value such as a normalized cross correlation (NCC) and a zero-mean normalized cross correlation (ZNCC). The correlation value may be a value indicating similarity. Moreover, although the correlation value is used in the first embodiment, a degree of difference such as a sum of squared difference (SSD) and a sum of absolute difference (SAD) may be used. When the degree of difference is used, it is determined in step S135a to be described later whether or not the degree of difference is larger than the first predetermined value. The degree of difference may be a value indicating non-similarity.

After step S130a is performed, the comparison and determination unit 442 compares the correlation value calculated in step S130a with the first predetermined value and determines whether or not the correlation value is smaller than the first predetermined value (step S135a). Step S135a corresponds to step S135 in FIG. 7. In this way, the comparison and determination unit 442 determines the reliability. The comparison and determination unit 442 outputs the determination result information 112 indicating the determination result to the control unit 45.

When it is determined in step S135a that the correlation value is smaller than the first predetermined value, the process of step S140 is performed. When it is determined in step S135a that the correlation value is larger than the first predetermined value, the process of step S145 is performed.

Aspects other than the above-described aspect of the process shown in FIG. 11 are the same as those of the process shown in FIG. 7.

Figure 12:
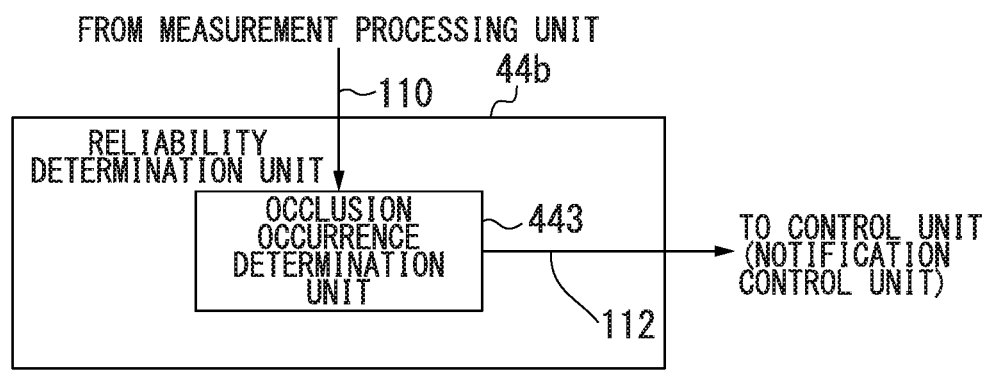
FIG. 12 is a block diagram showing a configuration of the reliability determination unit of the measurement endoscope apparatus according to the first embodiment of the present invention.

FIG. 12 shows a configuration of a reliability determination unit 44b which is a second example of the reliability determination unit 44. As shown in FIG. 12, the reliability determination unit 44b has an occlusion occurrence determination unit 443. The occlusion occurrence determination unit 443 determines whether or not occlusion has occurred. When the occlusion occurrence determination unit 443 determines that occlusion has occurred, the reliability determination unit 44b determines that the reliability is low.

Figure 13:
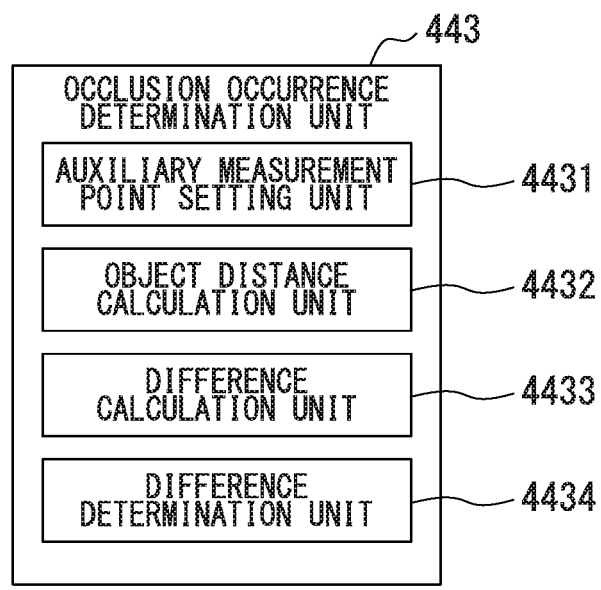
FIG. 13 is a block diagram showing a configuration of an occlusion occurrence determination unit of the measurement endoscope apparatus according to the first embodiment of the present invention.

FIG. 13 shows a configuration of the occlusion occurrence determination unit 443. As shown in FIG. 13, the occlusion occurrence determination unit 443 includes an auxiliary measurement point setting unit 4431, an object distance calculation unit 4432, a difference calculation unit 4433, and a difference determination unit 4434.

The auxiliary measurement point setting unit 4431 processes at least the video signal (the image data 109) corresponding to the first image, thereby setting a first auxiliary measurement point on the left side of the measurement point in the first image and setting a second auxiliary measurement point on the right side of the measurement point in the first image. The object distance calculation unit 4432 calculates a first object distance at the first auxiliary measurement point and a second object distance at the second auxiliary measurement point. The difference calculation unit 4433 calculates a difference between the first and second object distances. The difference determination unit 4434 compares the difference with a second predetermined value and determines that occlusion has occurred when the difference is larger than the second predetermined value.

Whether or not occlusion has occurred is determined depending on whether or not an obstacle is present on an epipolar plane. Due to this, the first and second auxiliary measurement points are set on both sides of the measurement point on an epipolar line on the first image (the left screen). However, when collimation (rectification) is performed, since the epipolar line is parallel to a horizontal direction of the screen, the first and second auxiliary measurement points have only to be set to the left and right sides of the measurement point. In the first embodiment, the latter case where the collimation is performed will be described.

Figure 14:
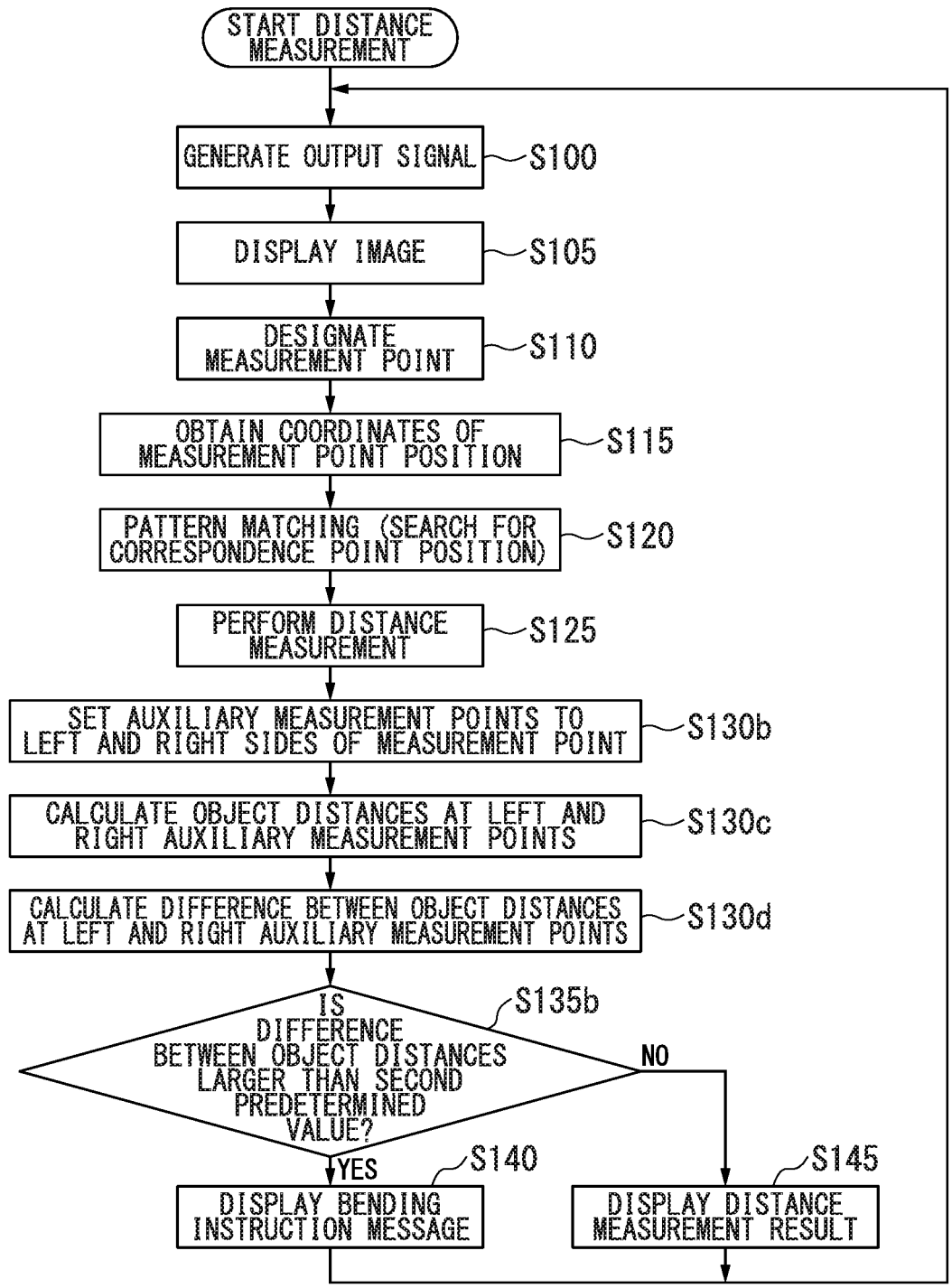
FIG. 14 is a flowchart showing the procedure of an operation of the measurement endoscope apparatus according to the first embodiment of the present invention.

FIG. 14 shows the procedure of an operation of the measurement endoscope apparatus 1 during distance measurement. When the measurement endoscope apparatus 1 has the reliability determination unit 44b, the measurement endoscope apparatus 1 performs the process shown in FIG. 14. The difference between FIGS. 7 and 14 will be described.

After step S125 is performed, the auxiliary measurement point setting unit 4431 sets the first auxiliary measurement point to the left side of the measurement point in the first image and sets the second auxiliary measurement point to the right side of the measurement point in the first image on the basis of the measurement information 110 from the measurement processing unit 43 (step S130b). The measurement information 110 includes position information of the measurement point and the correspondence point. Moreover, the measurement information 110 includes image data of a region including the position of the measurement point in the first image and image data of a region including the position of the correspondence point in the second image.

Figure 15:
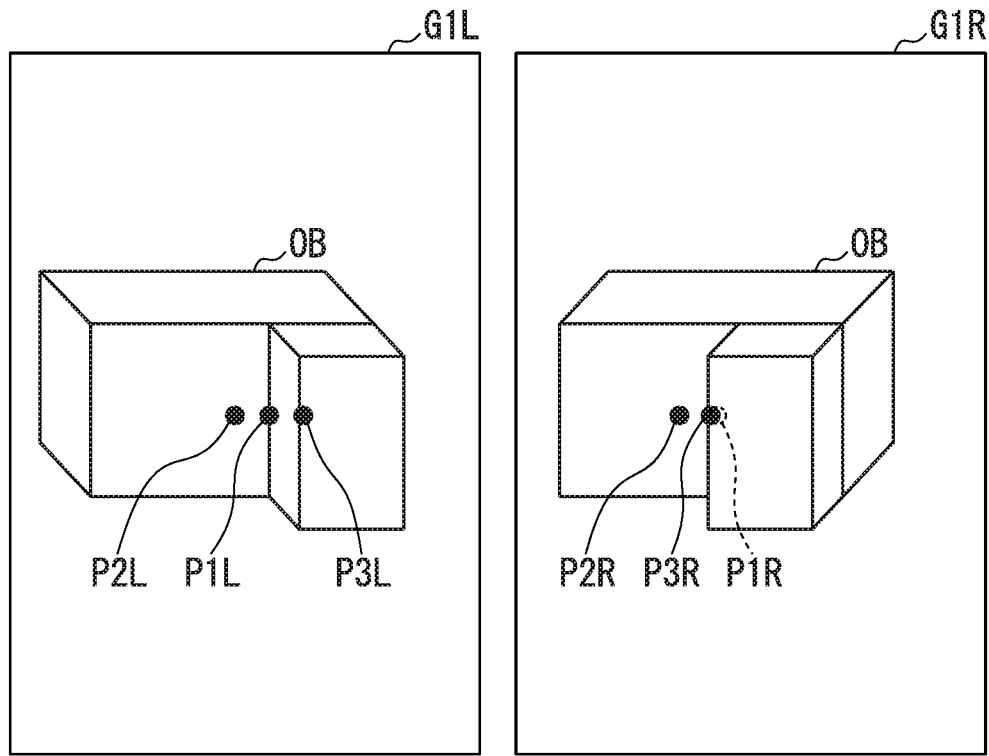
FIG. 15 is a reference diagram showing an image processed by the reliability determination unit of the measurement endoscope apparatus according to the first embodiment of the present invention.

FIG. 15 shows an example of an image processed by the reliability determination unit 44b. A first image G1L and a second image G1R are the images of the subject OB. A measurement point P1L is designated in the region of the subject OB in the first image G1L. The measurement point P1L is designated on a region having a step. In the second image G1R, a correspondence point P1R corresponding to the measurement point P1L is included in a blind area generated due to a step on the surface of the subject OB. Due to this, in the second image G1R, it is not possible to observe the correspondence point P1R corresponding to the measurement point P1L.

In step S130b, the auxiliary measurement point setting unit 4431 sets a first auxiliary measurement point P2L to the left side of the measurement point P1L and sets a second auxiliary measurement point P3L to the right side of the measurement point P1L. That is, the auxiliary measurement point setting unit 4431 sets the first and second auxiliary measurement points P2L and P3L so as to sandwich the measurement point P1L. The first and second auxiliary measurement points P2L and P3L are points near the measurement point P1L. The first auxiliary measurement point P2L is a point on the left side of a vertical line that passes through the measurement point P1L. The second auxiliary measurement point P3L is a point on the right side of a vertical line that passes through the measurement point P1L. For example, the first and second auxiliary measurement points P2L and P3L are points on a horizontal line that passes through the measurement point P1L in the first image G1L. For example, in the first image G1L, the distance between the measurement point P1L and the first auxiliary measurement point P2L and the distance between the measurement point P1L and the second auxiliary measurement point P3L are predetermined distances. A point at the second auxiliary measurement point P3L in the subject OB is on a step. Due to this, the object distance to the first auxiliary measurement point P2L is larger than the object distance to the second auxiliary measurement point P3L.

After step S130b is performed, the object distance calculation unit 4432 calculates a first object distance at the first auxiliary measurement point and a second object distance at the second auxiliary measurement point on the basis of the measurement information 110 from the measurement processing unit 43 (step S130c). In step S130c, the object distance calculation unit 4432 calculates a first auxiliary correspondence point of the second image corresponding to the first auxiliary measurement point and a second auxiliary correspondence point of the second image corresponding to the second auxiliary measurement point by a process similar to the process of step S120. Furthermore, the object distance calculation unit 4432 calculates 3-dimensional coordinates of the first auxiliary measurement point and 3-dimensional coordinates of the second auxiliary measurement point by a process similar to the process of step S125. A Z-coordinate value of the first auxiliary measurement point is the first object distance at the first auxiliary measurement point, and a Z-coordinate value of the second auxiliary measurement point is the second object distance at the second auxiliary measurement point.

In FIG. 15, a first auxiliary correspondence point P2R corresponds to the first auxiliary measurement point P2L and a second auxiliary correspondence point P3R corresponds to the second auxiliary measurement point P3L. The first and second auxiliary correspondence points P2R and P3R can be observed in the second image G1R.

After step S130c is performed, the difference calculation unit 4433 calculates the difference between the first and second object distances calculated in step S130b (step S130d). The difference calculated in step S130d is an absolute value of a value obtained by subtracting the second object distance from the first object distance. Steps S130b, S130c, and S130d correspond to step S130 in FIG. 7.

After step S130d is performed, the difference determination unit 4434 compares the difference calculated in step S130d with a second predetermined value and determines whether or not the difference is larger than the second predetermined value (step S135b). Step S135b corresponds to step S135 in FIG. 7. In this way, the difference determination unit 4434 determines the reliability. The difference determination unit 4434 outputs determination result information 112 indicating the determination result to the control unit 45.

The difference determination unit 4434 can determine whether or not occlusion has occurred on the basis of the difference in object distance. When the difference in object distance at two auxiliary measurement points set to both sides of the measurement point is large, it is highly possible that a large step at which the heights in a depth direction near the measurement point are different is present. That is, it is highly possible that occlusion has occurred.

When it is determined in step S135b that the difference is larger than the second predetermined value, the process of step S140 is performed. When it is determined in step S135b that the difference is smaller than the second predetermined value, the process of step S145 is performed.

Aspects other than the above-described aspect of the process shown in FIG. 14 are the same as those of the process shown in FIG. 7.

The auxiliary measurement point setting unit 4431 may set a plurality of first auxiliary measurement points and a plurality of second auxiliary measurement points. That is, the auxiliary measurement point setting unit 4431 may set a plurality of first auxiliary measurement points to the left side of the measurement point and set a plurality of second auxiliary measurement points to the right side of the measurement point. The plurality of first auxiliary measurement points are points on the left side of a vertical line that passes through the measurement point. The plurality of second auxiliary measurement points are points on the right side of a vertical line that passes through the measurement point. For example, the plurality of first auxiliary measurement points and the plurality of second auxiliary measurement points are points on a horizontal line that passes through the measurement point in the first image. For example, the interval of the plurality of first auxiliary measurement points in the first image is equal to the interval of the plurality of second auxiliary measurement points in the first image.

When a plurality of first auxiliary measurement points and a plurality of second auxiliary measurement points are set, the object distance calculation unit 4432 calculates a first object distance at each of the plurality of first auxiliary measurement points and a second object distance at each of the plurality of second auxiliary measurement points. The object distance calculation unit 4432 calculates the average value of the first object distances at the plurality of first auxiliary measurement points. Moreover, the object distance calculation unit 4432 calculates the average value of the second object distances at the plurality of second auxiliary measurement points.

When the plurality of first auxiliary measurement points and the plurality of second auxiliary measurement points are set, the difference calculation unit 4433 calculates a difference between the average value of the first object distances and the average value of the second object distances. The difference determination unit 4434 determines whether or not this difference is larger than a second predetermined value.

Figure 16:
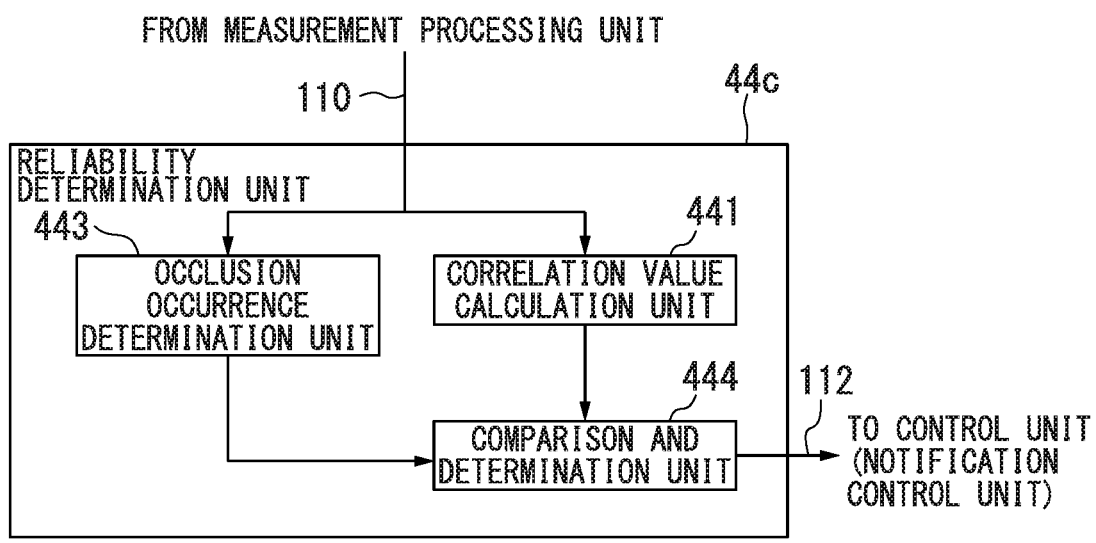
FIG. 16 is a block diagram showing a configuration of the reliability determination unit of the measurement endoscope apparatus according to the first embodiment of the present invention.

FIG. 16 shows a configuration of a reliability determination unit 44c which is a third example of the reliability determination unit 44. As shown in FIG. 16, the reliability determination unit 44c includes a correlation value calculation unit 441, an occlusion occurrence determination unit 443, and a comparison and determination unit 444.

The correlation value calculation unit 441 in FIG. 16 is the same as the correlation value calculation unit 441 in FIG. 10. That is, the correlation value calculation unit 441 calculates a correlation value between the position of the measurement point in the first image and the position of the correspondence point in the second image. The occlusion occurrence determination unit 443 in FIG. 16 is the same as the occlusion occurrence determination unit 443 in FIG. 13. That is, the occlusion occurrence determination unit 443 determines whether or not occlusion has occurred. The comparison and determination unit 444 determines the reliability on the basis of a comparison result obtained by comparing a correlation value or a degree of difference with the first predetermined value and the determination result of the occlusion occurrence determination unit 443. For example, the comparison and determination unit 444 compares the correlation value with the first predetermined value. The comparison and determination unit 444 determines that the reliability is low when the correlation value is smaller than the first predetermined value and the occlusion occurrence determination unit 443 determines that occlusion has occurred. Alternatively, the comparison and determination unit 444 compares the degree of difference with the first predetermined value. The comparison and determination unit 444 determines that the reliability is low when the degree of difference is larger than the first predetermined value and the occlusion occurrence determination unit 443 determines that occlusion has occurred.

Figure 17:
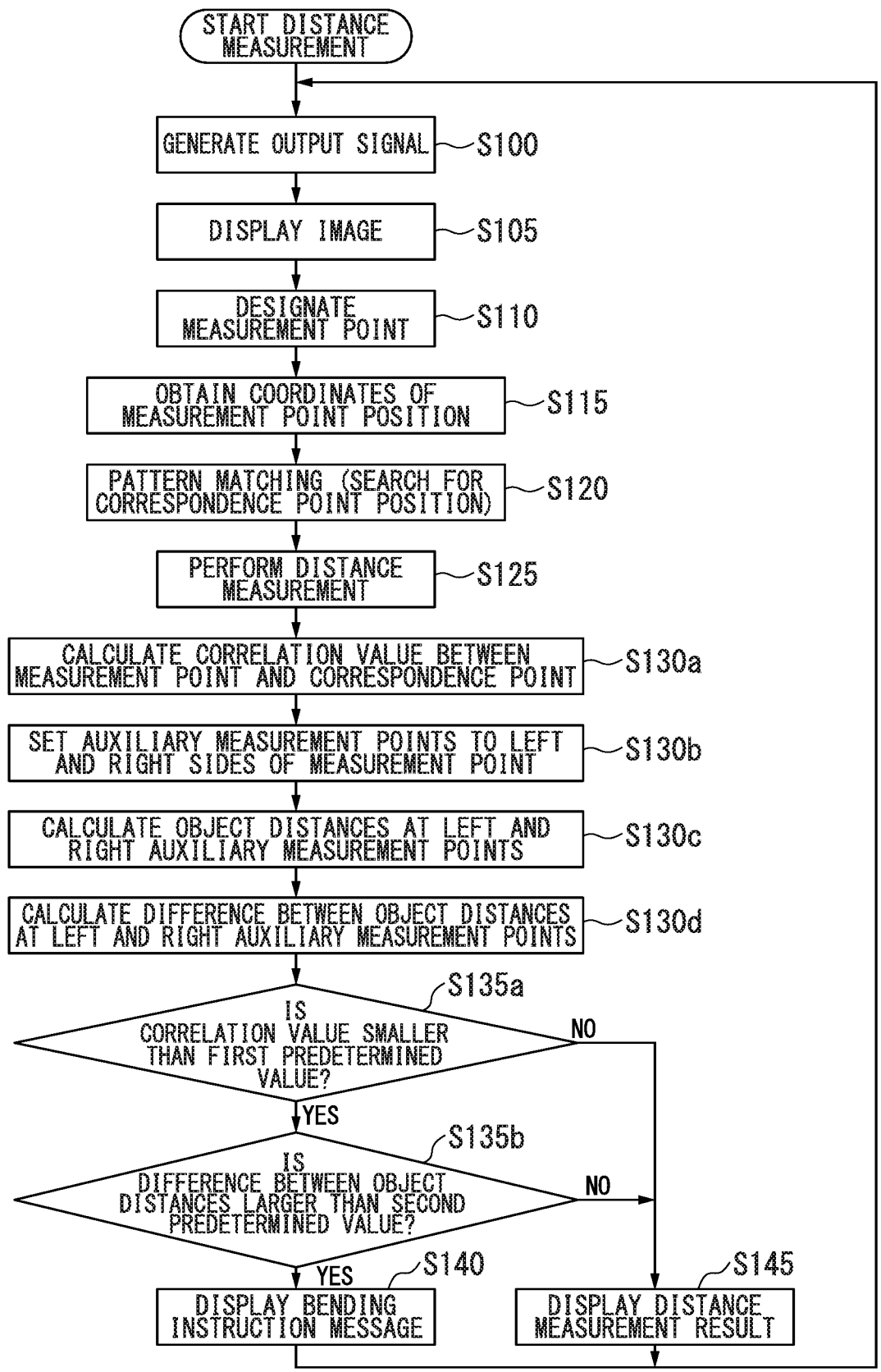
FIG. 17 is a flowchart showing the procedure of an operation of the measurement endoscope apparatus according to the first embodiment of the present invention.

FIG. 17 shows the procedure of an operation of the measurement endoscope apparatus 1 during distance measurement. When the measurement endoscope apparatus 1 has the reliability determination unit 44c, the measurement endoscope apparatus 1 performs a process shown in FIG. 17. The difference between FIGS. 11, 14, and 17 will be described.

After step S125 is performed, the process of step S130a is performed. After step S130a is performed, the processes of steps S130b, S140c, and S130d are performed sequentially. After step S130d is performed, the process of step S135a is performed.

When it is determined in step S135a that the correlation value is smaller than the first predetermined value, the process of step S135b is performed. When it is determined in step S135a that the correlation value is larger than the first predetermined value, the process of step S145 is performed.

When it is determined in step S135b that the difference is larger than the second predetermined value, the process of step S140 is performed. When it is determined in step S135b that the difference is smaller than the second predetermined value, the process of step S145 is performed.

Aspects other than the above-described aspect of the process shown in FIG. 17 are the same as those of the process shown in FIGS. 11 and 14.

In FIG. 17, the processes of steps S130a and S135a shown in FIG. 11 and the processes of steps S130b, S130c, S130d, and S135b shown in FIG. 14 are combined. Due to this, the reliability determination unit 44c can determine whether or not occlusion has occurred with higher accuracy.

According to the first embodiment, the measurement endoscope apparatus 1 includes the endoscope insertion unit 2, the first optical system 31 (a first imaging optical system), the second optical system 32 (a second imaging optical system), an imaging element 21, a measurement processing unit 43, a reliability determination unit 44, and a notification control unit 451.

An endoscope apparatus of the respective aspects of the present invention may not have components corresponding to the operating unit 5, the display unit 6, the video signal processing unit 34, the signal conversion unit 38, the image storage unit 42, and the external storage medium 46.

In the first embodiment, when the reliability determination unit 44 determines that the reliability is low, the notification control unit 451 sends a notification to prompt the user to perform a bending operation of bending the distal end 20 of the endoscope insertion unit 2 so that the distal end 20 of the endoscope insertion unit 2 is moved toward the first optical system 31 in the parallax direction. In this way, it is possible to suppress a decrease in measurement accuracy due to the occurrence of occlusion.

Second Embodiment

Figure 18:
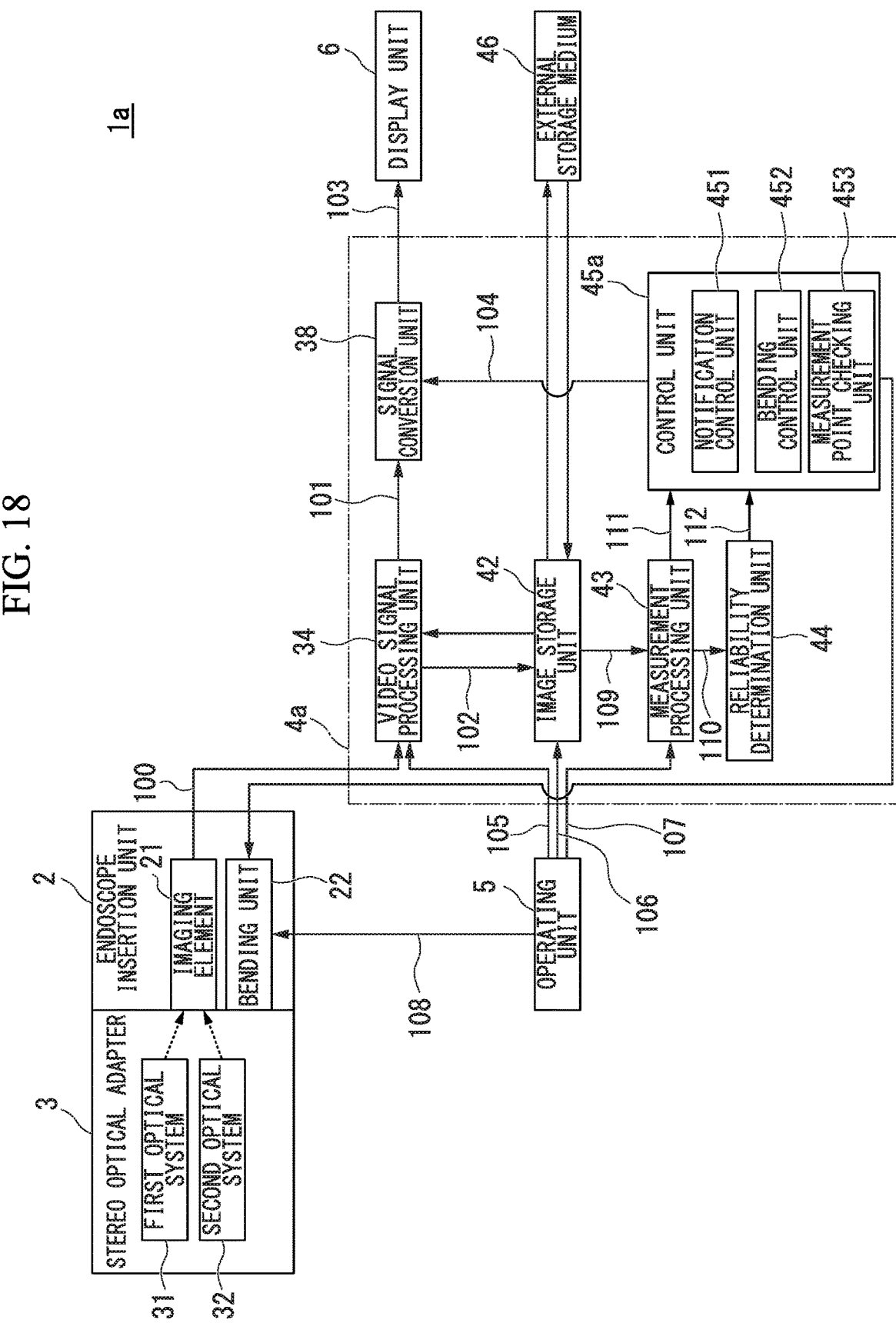
FIG. 18 is a block diagram showing a configuration of a measurement endoscope apparatus according to a second embodiment of the present invention.

In a second embodiment of the present invention, the measurement endoscope apparatus 1 of the first embodiment is changed to a measurement endoscope apparatus 1a shown in FIG. 18. An external view of the measurement endoscope apparatus 1a is similar to the external view of the measurement endoscope apparatus 1 shown in FIG. 1. The distal end 20 of the endoscope insertion unit 2 and the stereo optical adapter 3 have the same configuration as that shown in FIGS. 2 and 3.

FIG. 18 shows a configuration of the measurement endoscope apparatus 1a of the second embodiment. The difference between FIGS. 4 and 18 will be described.

The controller 4 shown in FIG. 4 is changed to a controller 4a. In the controller 4a, the control unit 45 in FIG. 4 is changed to a control unit 45a. The control unit 45a includes a notification control unit 451, a bending control unit 452, and a measurement point checking unit 453. The bending control unit 452 controls the bending unit 22 so that the distal end 20 of the endoscope insertion unit 2 is moved toward the first optical system 31 in the parallax direction when the reliability determination unit 44 determines that the reliability is low. In other words, the bending control unit 452 controls the bending unit 22 so that the distal end 20 of the endoscope insertion unit 2 is moved in a direction from the position (the second position) of the second optical center 64 of the second optical system 32 toward the position (the first position) of the first optical center 63 of the first optical system 31 when the reliability determination unit 44 determines that the reliability is low. That is, in the second embodiment, when occlusion occurs, the measurement endoscope apparatus 1a bends the distal end 20 of the endoscope insertion unit 2 automatically in a direction of avoiding the occlusion.

The bending control unit 452 calculates the bending amount for causing a point on a subject to be included in a field of view of the second optical system 32. Before the bending control unit 452 controls bending based on the bending amount, the measurement point checking unit 453 determines whether or not the point on the subject is included in the field of view of the first optical system 31 when the distal end 20 of the endoscope insertion unit 2 is virtually bent by the bending amount. The notification control unit 451 sends a notification to prompt the user to perform an operation of moving the distal end 20 of the endoscope insertion unit 2 away from the subject when it is determined that the point on the subject is not included in the field of view of the first optical system 31 when the distal end 20 of the endoscope insertion unit 2 is virtually bent by the bending amount. The point on the subject is a spatial point on a subject at estimated 3-dimensional coordinates of the measurement point.

Aspects other than the above-described aspect of the configuration shown in FIG. 18 are the same as those of the configuration shown in FIG. 4.

Figure 19:
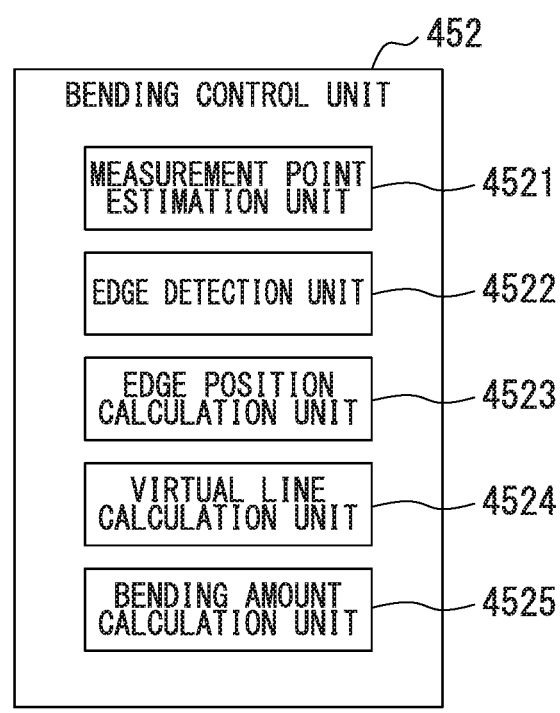
FIG. 19 is a block diagram showing a configuration of a bending control unit of the measurement endoscope apparatus according to the second embodiment of the present invention.

FIG. 19 shows a configuration of the bending control unit 452. As shown in FIG. 19, the bending control unit 452 includes a measurement point estimation unit 4521, an edge detection unit 4522, an edge position calculation unit 4523, a virtual line calculation unit 4524, and a bending amount calculation unit 4525.

The measurement point estimation unit 4521 estimates the 3-dimensional coordinates of the measurement point by processing at least a video signal (the image data 109) corresponding to the first image and a video signal (the image data 109) corresponding to the second image. The edge detection unit 4522 detects an edge at which a change in image density of the first image is relatively large by processing at least the video signal (the image data 109) corresponding to the first image. The edge is disposed on the parallax direction side of the measurement point of the first image. The parallax direction is a direction from the first optical center (the first optical center 63 in FIG. 6) of the first optical system 31 toward the second optical center (the second optical center 64 in FIG. 6) of the second optical system 32.

The edge position calculation unit 4523 calculates 3-dimensional coordinates of an edge point in the edge by the principle of triangulation by processing at least the video signal (the image data 109) corresponding to the first image and the video signal (the image data 109) corresponding to the second image. The virtual line calculation unit 4524 calculates a virtual line (a virtual straight line) that passes through the estimated 3-dimensional coordinates of the measurement point and the 3-dimensional coordinates of the edge point.

The bending amount calculation unit 4525 calculates a bending amount for causing the point on the subject in the estimated 3-dimensional coordinates of the measurement point to be included in the field of view of the second optical system 32. That is, the bending amount calculation unit 4525 calculates a bending amount necessary for moving the second optical center of the second optical system 32 to a position on the virtual line or a position on the opposite side of the virtual line in the parallax direction. In other words, the bending amount calculation unit 4525 calculates a bending amount necessary for moving a projection point of the second optical center of the second optical system 32 to a position on a virtual projection line or a position on the opposite side of the virtual projection line in the parallax direction. The projection point of the second optical center of the second optical system 32 is a point obtained by projecting the second optical center of the second optical system 32 onto an epipolar plane that extends in both the parallax direction and the optical axis directions of the first and second optical systems 31 and 32. The virtual projection line is a straight line obtained by projecting a virtual line onto the epipolar plane.

The virtual line calculation unit 4524 may calculate a virtual line that passes through the position of the measurement point on the light receiving surface 24 of the imaging element 21 and the first optical center of the first optical system 31. That is, the bending amount calculation unit 4525 may calculate a bending amount necessary for moving the second optical center of the second optical system 32 to a position on the virtual line or a position on the opposite side of the virtual line in the parallax direction. In other words, the bending amount calculation unit 4525 may calculate the bending amount necessary for moving the projection point of the second optical center of the second optical system 32 to a position on a virtual projection line or a position on the opposite side of the virtual projection line in the parallax direction.

The processing of at least a video signal corresponding to the first image and a video signal corresponding to the second image includes processing of a video signal of a portion corresponding to the first image and processing of a video signal of a portion corresponding to the second image, of the video signals corresponding to the first and second images. Alternatively, the processing of at least the video signal corresponding to the first image and the video signal corresponding to the second image includes processing of a video signal corresponding to the first image only and processing of a video signal corresponding to the second image only.

The measurement point estimation unit 4521 sets a plurality of auxiliary measurement points near the measurement point in the first image by processing at least the video signal (the image data 109) corresponding to the first image. The measurement point estimation unit 4521 searches for a plurality of auxiliary correspondence points of the second image corresponding to the plurality of auxiliary measurement points by processing at least the video signal (the image data 109) corresponding to the first image and the video signal (the image data 109) corresponding to the second image. The measurement point estimation unit 4521 calculates the 3-dimensional coordinates of the plurality of auxiliary measurement points by the principle of triangulation using the plurality of auxiliary correspondence points that are searched for (specified) and the plurality of auxiliary measurement points. The measurement point estimation unit 4521 estimates the 3-dimensional coordinates of the measurement point by calculating the 3-dimensional coordinates of an intersection point between a virtual line that passes through both of the position of the measurement point on the light receiving surface 24 of the imaging element 21 and the first optical center (the first optical center 63 in FIG. 6) of the first optical system 31 and a plane based on the 3-dimensional coordinates of the plurality of auxiliary measurement points.

Figure 20:
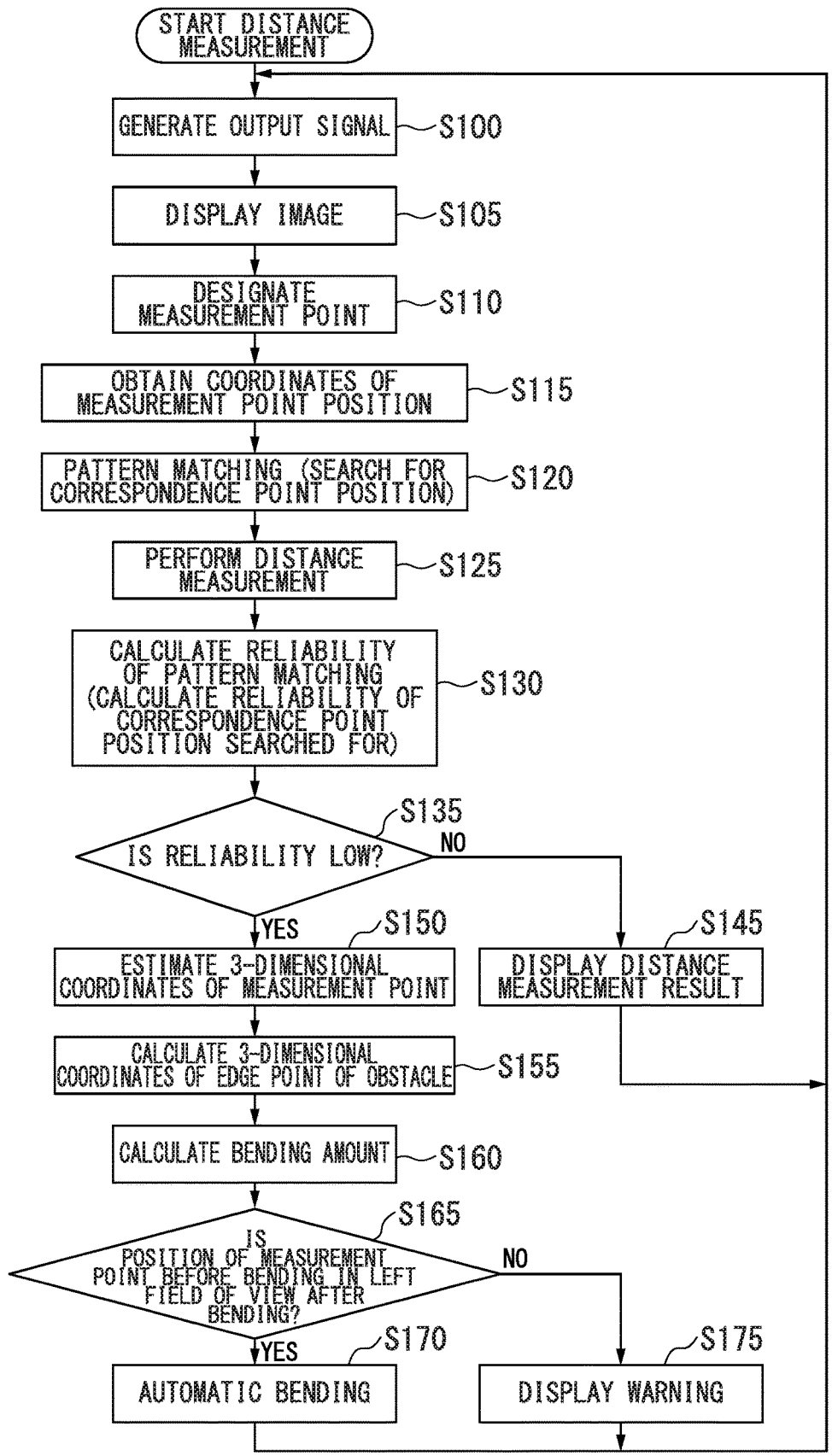
FIG. 20 is a flowchart showing the procedure of an operation of the measurement endoscope apparatus according to the second embodiment of the present invention.

FIG. 20 shows the procedure of an operation of the measurement endoscope apparatus 1a during distance measurement. The difference between FIGS. 7 and 20 will be described.

When it is determined in step S135 that the reliability is low, the measurement point estimation unit 4521 estimates the 3-dimensional coordinates of the measurement point (step S150). The details of the process of step S150 will be described.

Figure 21:
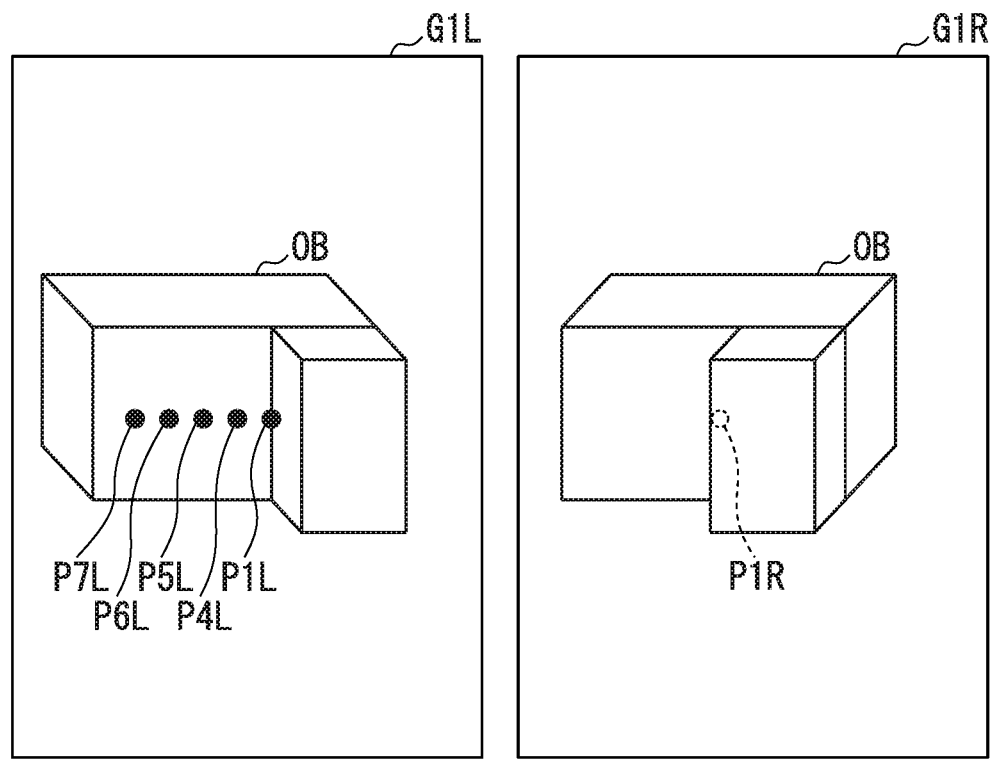
FIG. 21 is a reference diagram showing an image processed by the bending control unit of the measurement endoscope apparatus according to the second embodiment of the present invention.

FIG. 21 shows an example of an image processed by the bending control unit 452. A first image G1L and a second image G1R are the images of the subject OB. A measurement point P1L is designated in the region of the subject OB in the first image G1L. The measurement point P1L is designated on a region having a step. In the second image G1R, a correspondence point P1R corresponding to the measurement point P1L is included in a blind area generated due to a step on the surface of the subject OB. Due to this, in the second image G1R, it is not possible to observe the correspondence point P1R corresponding to the measurement point P1L.

In step S150, the measurement point estimation unit 4521 sets an auxiliary measurement point P4L, an auxiliary measurement point PSL, an auxiliary measurement point P6L, and an auxiliary measurement point P7L to the left side of the measurement point P1L. The auxiliary measurement points P4L, PSL, P6L, and P7L are points on the left side of a vertical line that passes through the measurement point P1L. For example, the auxiliary measurement points P4L, PSL, P6L, and P7L are points on a horizontal line (an epipolar line) that passes through the measurement point P1L in the first image G1L. For example, the intervals of the respective auxiliary measurement points in the first image G1L are equal.

The measurement point estimation unit 4521 calculates auxiliary correspondence points of the second image corresponding to the respective auxiliary measurement points by a process similar to the process of step S120. Furthermore, the measurement point estimation unit 4521 calculates the 3-dimensional coordinates of the respective auxiliary measurement points by a process similar to the process of step S125.

Figure 22:
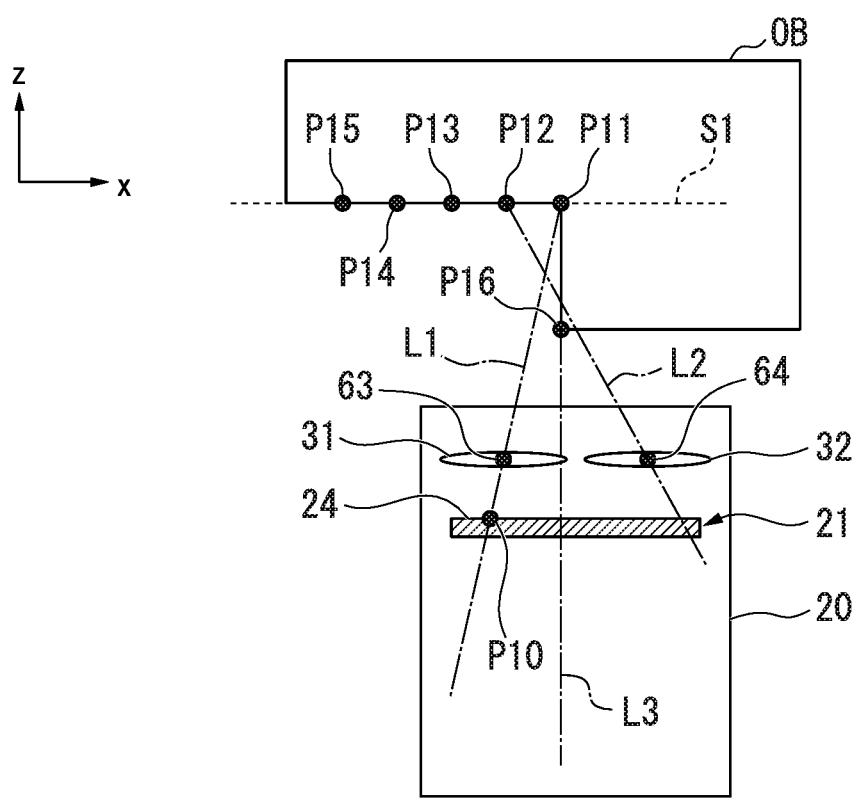
FIG. 22 is a reference diagram showing the positions of a subject and a distal end of an endoscope insertion unit of the measurement endoscope apparatus according to the second embodiment of the present invention.

FIG. 22 schematically shows the positions of the subject OB and the distal end 20 of the endoscope insertion unit 2. FIG. 22 shows a state in which the subject OB and the distal end 20 of the endoscope insertion unit 2 are projected on the xz-plane shown in FIG. 6. A point on the space in FIG. 22 is shown as a point projected on the xz-plane.

Light from a point on the surface of the subject OB passes through the first optical center 63 of the first optical system 31 and forms an optical image on the light receiving surface 24 of the imaging element 21. Similarly, light from a point on the surface of the subject OB passes through the second optical center 64 of the second optical system 32 and forms an optical imaged on the light receiving surface 24 of the imaging element 21. A point P11 at which a virtual line L1 that passes through a point P10 at the position of the measurement point on the light receiving surface 24 and the first optical center 63 intersects the surface of the subject OB is a point estimated as the spatial point on the subject corresponding to the measurement point. A point P12 is a spatial point on the subject corresponding to the auxiliary measurement point P4L. A point P13 is a spatial point on the subject corresponding to the auxiliary measurement point PSL. A point P14 is a spatial point on the subject corresponding to the auxiliary measurement point P6L. A point P15 is a spatial point on the subject corresponding to the auxiliary measurement point P7L. For example, the measurement point estimation unit 4521 calculates the 3-dimensional coordinates of the points P12, P13, P14, and P15.

The measurement point estimation unit 4521 uses the 3-dimensional coordinates of two or more points having higher reliability among the plurality of auxiliary measurement points. For example, in FIG. 22, a virtual line L2 that passes through the point P12 and the second optical center 64 is blocked by the edge of the subject OB. That is, the point P12 cannot be observed in the second image. Due to this, the correspondence point searching unit 432 cannot search the second image for the correspondence point corresponding to the point P12. On the other hand, the points P13, P14, and P15 can be observed in the second image. Due to this, the correspondence point searching unit 432 can search the second image for the correspondence points corresponding to the points P13, P14, and P15.

Therefore, the measurement point estimation unit 4521 uses the 3-dimensional coordinates of the auxiliary measurement points P5L, P6L, and P7L (that is, the 3-dimensional coordinates of the points P13, P14, and P15). In this way, the measurement point estimation unit 4521 can estimate the 3-dimensional coordinates of the measurement point with high accuracy. For example, the reliability of the auxiliary measurement point is obtained as the correlation value between the position of the auxiliary measurement point in the first image and the position of the correspondence point corresponding to the auxiliary measurement point in the second image. The measurement point estimation unit 4521 may use the 3-dimensional coordinates of two or more points having higher correlation values among the plurality of auxiliary measurement points.

The measurement point estimation unit 4521 calculates a surface shape of the subject OB when the subject OB is cut by the epipolar plane near the measurement point on the basis of the 3-dimensional coordinates of two or more auxiliary measurement points. For example, the measurement point estimation unit 4521 calculates an approximate straight line S1 that passes through the three points P13, P14, and P15 on the epipolar plane on the basis of the 3-dimensional coordinates of the points P13, P14, and P15 in FIG. 22. The measurement point estimation unit 4521 regards this approximate straight line S1 as the shape on the epipolar line of the outer surface of the subject OB.

The measurement point estimation unit 4521 calculates a virtual line that passes through the position of the measurement point on the light receiving surface 24 of the imaging element 21 and the first optical center of the first optical system 31. For example, the measurement point estimation unit 4521 calculates a virtual line L1 on the epipolar plane that passes through the first optical center 63 and the point P10 in FIG. 22. The position of the light receiving surface 24 in a coordinate system shown in FIG. 6 is known. Due to this, the 3-dimensional coordinates of the position on the light receiving surface 24 is obtained in advance. The relation between the position of the light receiving surface 24 and the position in the first image is known. When a measurement point is designated in the first image, the measurement point estimation unit 4521 can calculate the 3-dimensional coordinates of the point P10 at the position of the measurement point on the light receiving surface 24 of the imaging element 21. Moreover, the 3-dimensional coordinates of the first optical center 63 is calculated in advance.

The measurement point estimation unit 4521 calculates the 3-dimensional coordinates of a point at which the virtual line intersects the approximate straight line. In this way, the measurement point estimation unit 4521 estimates the 3-dimensional coordinates of the measurement point. For example, the measurement point estimation unit 4521 calculates the 3-dimensional coordinates of the point P11 at which the virtual line L1 on the epipolar plane in FIG. 22 intersects the approximate straight line S1 on the epipolar plane. The 3-dimensional coordinates of the point P11 is the estimated 3-dimensional coordinates of the measurement point.

After step S150 is performed, the edge detection unit 4522 detects an edge of an obstacle having a step in the first image. Furthermore, the edge position calculation unit 4523 calculates the 3-dimensional coordinates of an edge point of the edge (step S155). The details of the process of step S155 will be described.

The edge detection unit 4522 performs image processing on the first image. In this way, the edge detection unit 4522 extracts an edge portion at which an image density changes abruptly. For example, the edge detection unit 4522 detects a portion in which a difference between the signal values of adjacent pixels on the left and right sides is relatively large as an edge portion. A region in which an edge portion of the first image is extracted is a region on the parallax direction side of the measurement point. For example, in FIG. 22, the parallax direction is the x-direction (that is, the rightward direction). That is, the region in which the edge portion is extracted is a region on the right side of the measurement point.

The edge position calculation unit 4523 sets an edge point of the extracted edge portion. The edge position calculation unit 4523 calculates an edge correspondence point of the second image corresponding to the edge point by a process similar to the process of step S120. Furthermore, the edge position calculation unit 4523 calculates the 3-dimensional coordinates of the edge point by a process similar to the process of step S125. For example, the edge position calculation unit 4523 calculates the 3-dimensional coordinates of a point P16 in FIG. 22. The point P16 is at an apex portion of the step on the surface of the subject OB.

After step S155 is performed, the virtual line calculation unit 4524 calculates a virtual line that passes through the estimated 3-dimensional coordinates of the measurement point and the 3-dimensional coordinates of the edge point. The bending amount calculation unit 4525 calculates a necessary bending amount (step S160). The details of the process of step S160 will be described.

For example, the virtual line calculation unit 4524 calculates a virtual line L3 that passes through points P11 and P16 in FIG. 22. The point P11 is a point estimated as a spatial point on the subject corresponding to the measurement point. The point P16 is an edge point.

In order for the spatial point on the subject corresponding to the measurement point to be observed via the second optical system 32, it is necessary to move the projection point of the second optical center 64 of the second optical system 32 to a position on a virtual projection line to be described later or a position on the opposite side of the virtual projection line in the parallax direction. The projection point of the second optical center 64 of the second optical system 32 is a point obtained by projecting the second optical center 64 of the second optical system 32 onto an epipolar plane that extends in both the parallax direction and the optical axis directions of the first and second optical systems 31 and 32. The virtual projection line is a straight line obtained by projecting a virtual line onto the epipolar plane.

For example, in FIG. 22, the parallax direction is the x-direction, and the optical axis directions of the first and second optical systems 31 and 32 are the z-direction. That is, the epipolar plane is an xz-plane. In FIG. 22, the projection point of the second optical center 64 of the second optical system 32 is a point obtained by projecting the second optical center 64 of the second optical system 32 onto the xz-plane. In FIG. 22, the virtual projection line is a straight line obtained by projecting the virtual line L3 onto the xz-plane. In FIG. 22, a straight line on a space is shown in a state of being projected on the xz-plane. Due to this, in FIG. 22, the projection point of the second optical center 64 of the second optical system 32 is at the position of the second optical center 64 of the second optical system 32. In FIG. 22, the virtual projection line is at the position of the virtual line L3. In FIG. 22, the direction opposite to the parallax direction is the leftward direction. Therefore, it is necessary to move the projection point of the second optical center 64 of the second optical system 32 to a position on the virtual projection line or a position on the left side of the virtual projection line.

Figure 23:
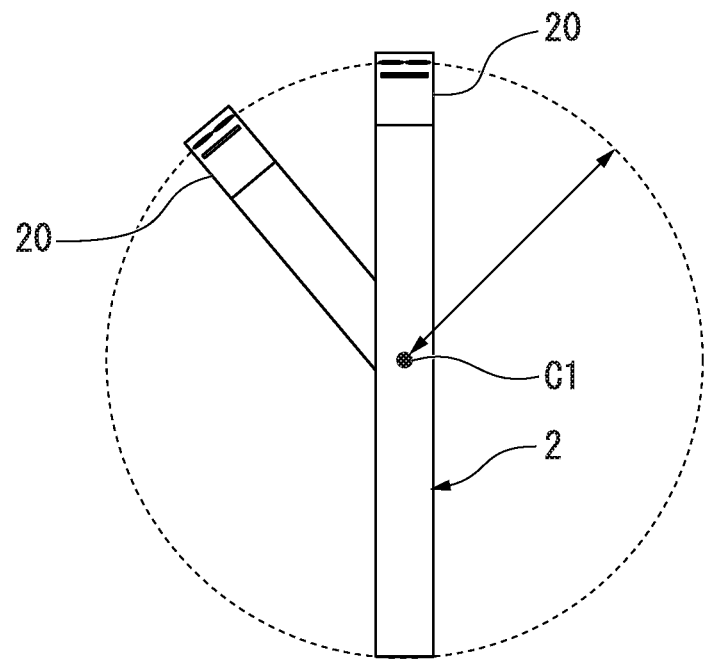
FIG. 23 is a reference diagram showing a state in which the distal end of the endoscope insertion unit of the measurement endoscope apparatus according to the second embodiment of the present invention is bent.

FIG. 23 shows a state in which the distal end 20 of the endoscope insertion unit 2 is bent. The trajectory of the distal end 20 of the endoscope insertion unit 2 when the distal end 20 of the endoscope insertion unit 2 is moved can be approximated as a circle around the center of bending C1. The center of bending C1 is a point fixed to the endoscope insertion unit 2. When it is assumed that the distal end 20 of the endoscope insertion unit 2 is moved to draw the circle, the bending amount calculation unit 4525 calculates the bending amount for moving the projection point of the second optical center 64 of the second optical system 32 to a position on the virtual projection line or a position on the left side of the virtual projection line.

In step S160, the bending amount may be calculated by the following process. The virtual line calculation unit 4524 calculates a virtual line (the virtual line L1 in FIG. 22) that passes through the position of the measurement point on the light receiving surface 24 of the imaging element 21 and the first optical center of the first optical system 31. As described above, the measurement point estimation unit 4521 can calculate the 3-dimensional coordinates of the position (the point P10 in FIG. 22) of the measurement point on the light receiving surface 24 of the imaging element 21. Moreover, the 3-dimensional coordinates of the first optical center of the first optical system 31 is calculated in advance. In calculation of the virtual line, the 3-dimensional coordinates of the measurement point estimated by the measurement point estimation unit 4521 is not essential.

When the projection point of the second optical center 64 of the second optical system 32 is moved to the position on a virtual projection line to be described later or a position on the opposite side of the virtual projection line in the parallax direction, the spatial point on the subject corresponding to the measurement point can be observed via the second optical system 32. The projection point of the second optical center 64 of the second optical system 32 is a point obtained by projecting the second optical center 64 of the second optical system 32 onto an epipolar plane that extends in both the parallax direction and the optical axis directions of the first and second optical systems 31 and 32. The virtual projection line is a straight line obtained by projecting a virtual line onto the epipolar plane.

For example, as described above, in FIG. 22, the epipolar plane is an xz-plane. In FIG. 22, the projection point of the second optical center 64 of the second optical system 32 is a point obtained by projecting the second optical center 64 of the second optical system 32 onto the xz-plane. In FIG. 22, the virtual projection line is a straight line obtained by projecting the virtual line L3 onto the xz-plane. In FIG. 22, a straight line on a space is shown in a state of being projected on the xz-plane. Due to this, in FIG. 22, the projection point of the second optical center 64 of the second optical system 32 is at the position of the second optical center 64 of the second optical system 32. In FIG. 22, the virtual projection line is at the position of the virtual line L1. In FIG. 22, the direction opposite to the parallax direction is the leftward direction. Therefore, the bending amount calculation unit 4525 calculates the bending amount for moving the projection point of the second optical center 64 of the second optical system 32 to a position on the virtual projection line or a position on the left side of the virtual projection line.

After step S160 is performed, the measurement point checking unit 453 determines whether or not the point on the subject on the estimated 3-dimensional coordinates of the measurement point is included in the field of view (the left field of view) of the first optical system 31 when the distal end 20 of the endoscope insertion unit 2 is virtually bent by the bending amount calculated in step S160 (step S165).

Figure 24:
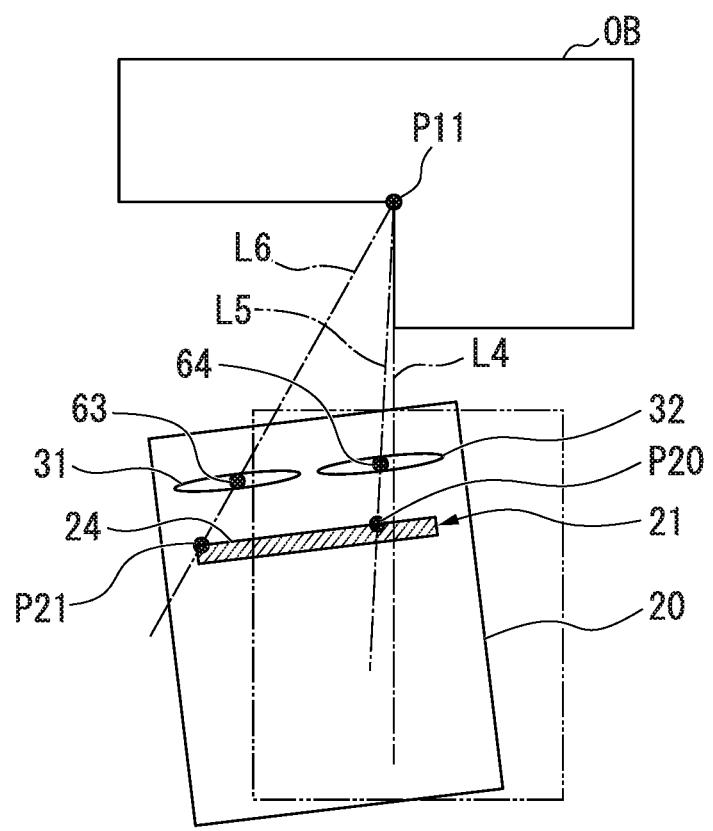
FIG. 24 is a reference diagram showing the positions of the subject and the distal end of the endoscope insertion unit of the measurement endoscope apparatus according to the second embodiment of the present invention.
Figure 25:
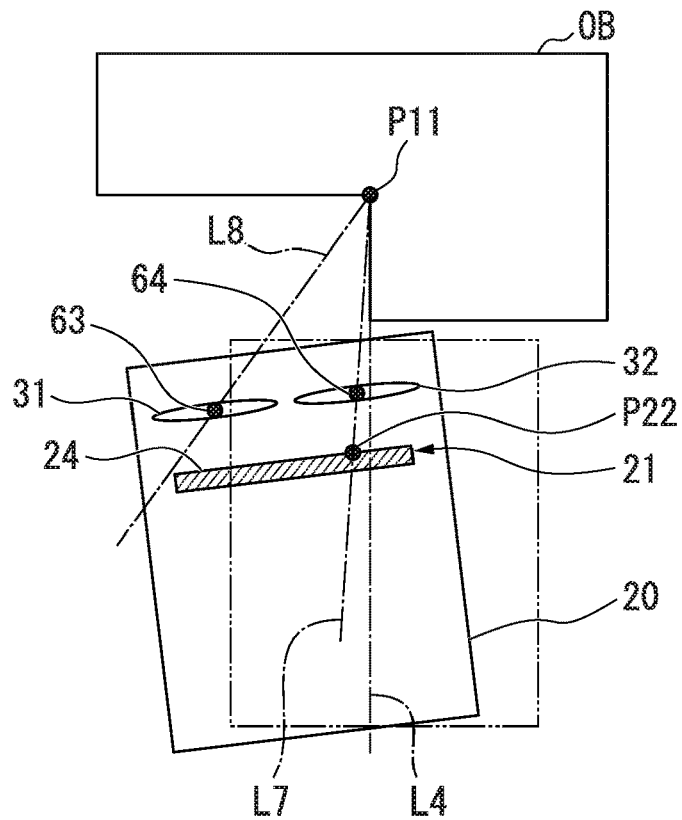
FIG. 25 is a reference diagram showing the positions of the subject and the distal end of the endoscope insertion unit of the measurement endoscope apparatus according to the second embodiment of the present invention.

FIGS. 24 and 25 schematically show the positions of the subject OB and the distal end 20 of the endoscope insertion unit 2. FIGS. 24 and 25 show a state in which the subject OB and the distal end 20 of the endoscope insertion unit 2 are projected on the xz-plane shown in FIG. 6. A point on the space in FIGS. 24 and 25 is shown as a point projected on the xz-plane. FIGS. 24 and 25 show a state in which the distal end 20 of the endoscope insertion unit 2 is bent.

As shown in FIG. 24, the projection point of the second optical center 64 of the second optical system 32 is on the left side of the virtual projection line L4. The virtual projection line L4 is a straight line obtained by projecting the virtual line L3 that passes through the estimated 3-dimensional coordinates of the measurement point and the 3-dimensional coordinates of the edge point onto the xz-plane. The point P11 is a point (that is, a subject point) estimated as a spatial point on the subject corresponding to the measurement point. A virtual line L5 that passes through the point P11 and the second optical center 64 intersects the light receiving surface 24 at a point P20. Due to this, light from the point P11 forms an optical image at the position of the point P20 on the light receiving surface 24 through the second optical system 32. That is, the point P11 is included in the field of view of the second optical system 32. Therefore, the point P11 can be observed in the second image.

On the other hand, as shown in FIG. 24, a virtual line L6 that passes through the point P11 and the first optical center 63 intersects the light receiving surface 24 at the point P21. Due to this, light from the point P11 forms an optical image at the position of the point P21 on the light receiving surface 24 through the first optical system 31. That is, the point P11 is included in the field of view of the first optical system 31. Therefore, the point P11 can be observed in the first image. As described above, in FIG. 24, the point P11 can be observed in the first image as the measurement point, and the point P11 can be observed in the second image as the correspondence point. Due to this, it is possible to obtain a highly accurate measurement result.

FIG. 25 shows a state in which the distal end 20 of the endoscope insertion unit 2 is close to the subject OB. As shown in FIG. 25, the projection point of the second optical center 64 of the second optical system 32 is on the left side of the virtual projection line L4. A virtual line L7 that passes through the point P11 which is a point on the subject and the second optical center 64 intersects the light receiving surface 24 at a point P22. Due to this, light from the point P11 forms an optical image at the position of the point P22 on the light receiving surface 24 through the second optical system 32.

That is, the point P11 is included in the field of view of the second optical system 32. Therefore, the point P11 can be observed in the second image.

On the other hand, as shown in FIG. 25, a virtual line L8 that passes through the point P11 and the first optical center 63 does not intersect the light receiving surface 24. Due to this, light from the point P11 does not form an optical image on the light receiving surface 24 through the first optical system 31. That is, the point P11 is not included in the field of view of the first optical system 31. Therefore, the point P11 cannot be observed in the first image. As a result, in FIG. 25, it is not possible to designate a point corresponding to the point P11 as the measurement point in the first image. That is, it is not possible to obtain a measurement result at the point P11. When the distal end 20 of the endoscope insertion unit 2 is close to the subject OB, the point P11 is hard to be included in the field of view of the first optical system 31.

In step S165, the measurement point checking unit 453 determines whether or not the subject OB and the distal end 20 of the endoscope insertion unit 2 after bending are in the state shown in FIG. 24. The details of the process of step S165 will be described.

The measurement point checking unit 453 calculates the 3-dimensional coordinates of the first optical center of the first optical system 31 after bending. The 3-dimensional coordinates of the first optical center of the first optical system 31 after bending can be calculated on the basis of the bending amount and the 3-dimensional coordinates of the first optical center of the first optical system 31 before bending. The measurement point checking unit 453 calculates a virtual line (the virtual line L6 in FIG. 24 and the virtual line L8 in FIG. 25) that passes through the estimated 3-dimensional coordinates of the measurement point and the 3-dimensional coordinates of the first optical center of the first optical system 31 after bending. The measurement point checking unit 453 determines whether or not the virtual line intersects the light receiving surface 24. The position of the light receiving surface 24 after bending can be calculated on the basis of the bending amount and the position of the light receiving surface 24 before bending.

When the virtual line intersects the light receiving surface 24, the point on the subject at the estimated 3-dimensional coordinates of the measurement point is included in the field of view of the first optical system 31. When the virtual line does not intersect the light receiving surface 24, the point on the subject at the estimated 3-dimensional coordinates of the measurement point is not included in the field of view of the first optical system 31.

The measurement point checking unit 453 may determine whether or not the point on the subject at the estimated 3-dimensional coordinates of the measurement point is included in the field of view of the first optical system 31 by the following process. The measurement point checking unit 453 calculates a first virtual line that passes through the estimated 3-dimensional coordinates of the measurement point and the 3-dimensional coordinates of the first optical center of the first optical system 31 after bending by the above-described process. Furthermore, the measurement point checking unit 453 calculates a second virtual line that passes through the 3-dimensional coordinates of one point at the left end of the light receiving surface 24 and the 3-dimensional coordinates of the first optical center of the first optical system 31 after bending. The measurement point checking unit 453 checks a geometric relation between the first virtual projection line obtained by projecting the first virtual line onto the xz-plane and the second virtual projection line obtained by projecting the second virtual line onto the xz-plane.

When the first virtual projection line in the region on the light receiving surface 24 side with respect to the first optical center of the first optical system 31 is on the right side of the second virtual projection line, the point on the subject at the estimated 3-dimensional coordinates of the measurement point is included in the field of view of the first optical system 31. When the first virtual projection line in the region on the light receiving surface 24 side with respect to the first optical center is on the left side of the second virtual projection line, the point on the subject at the estimated 3-dimensional coordinates of the measurement point is not included in the field of view of the first optical system 31.

When it is determined in step S165 that the point on the subject at the estimated 3-dimensional coordinates of the measurement point is included in the field of view of the first optical system 31, the bending control unit 452 controls the bending unit 22 so that the distal end 20 of the endoscope insertion unit 2 is moved toward the first optical system 31 in the parallax direction by the bending amount calculated in step S160. In this way, the bending unit 22 moves the distal end 20 of the endoscope insertion unit 2 toward the first optical system 31 in the parallax direction (step S170). As a result, occlusion at the position of the measurement point designated by the user is avoided. After step S170 is performed, the process of step S100 is performed.

When it is determined in step S165 that the point on the subject at the estimated 3-dimensional coordinates of the measurement point is not included in the field of view of the first optical system 31, the notification control unit 451 outputs measurement information 104 including a warning. In this way, the notification control unit 451 notifies the user of a warning. The signal conversion unit 38 generates the display video signal 103 by combining the measurement information 104 with the output video signal 101. The display unit 6 displays an image including a warning on the basis of the display video signal 103 (step S175). The warning includes a message that prompts the user to perform an operation of moving the distal end 20 of the endoscope insertion unit 2 away from the subject. After step S175 is performed, the process of step S100 is performed.

Figure 26:
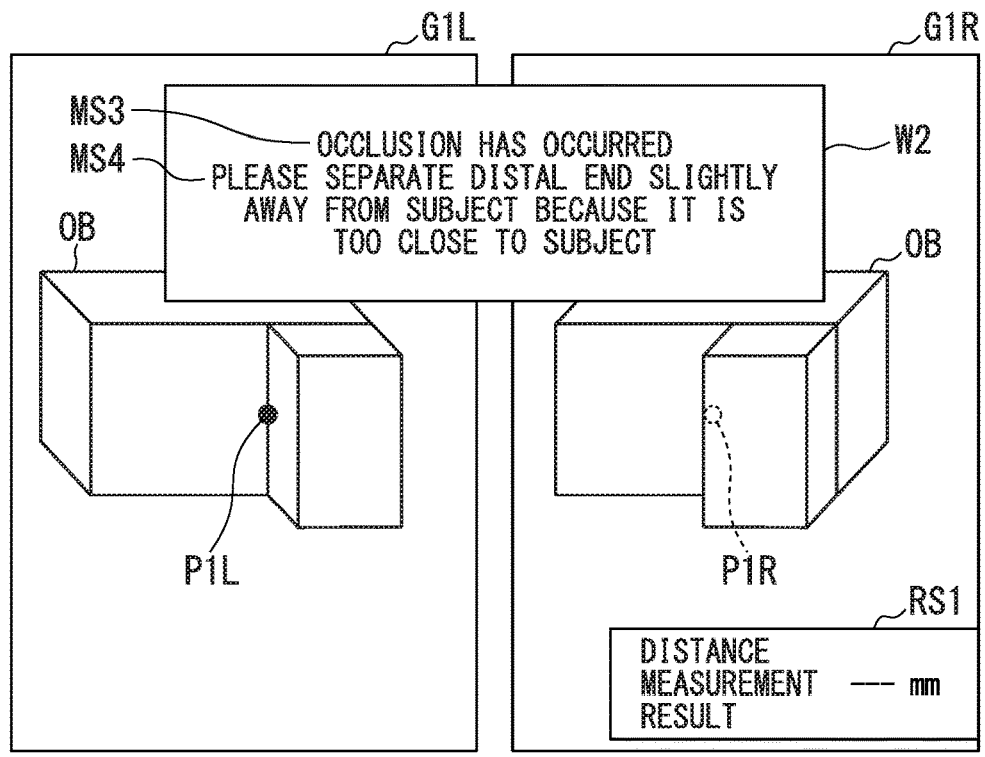
FIG. 26 is a reference diagram showing an image displayed by a display unit of the measurement endoscope apparatus according to the second embodiment of the present invention.

FIG. 26 shows an example of an image displayed by the display unit 6 in step S175. The difference between FIGS. 8 and 26 will be described. The display unit 6 displays a message window W2. The message window W2 includes a message MS3 indicating the occurrence of occlusion and a message MS4 for prompting the user to perform an operation of moving the distal end 20 of the endoscope insertion unit 2 away from the subject. Since the messages MS3 and MS4 are displayed, the user can understand that the distal end 20 of the endoscope insertion unit 2 should be bent moved away from the subject in order to avoid the occlusion. The user can move the distal end 20 of the endoscope insertion unit 2 away from the subject by operating the operating unit 5 according to the displayed message. Aspects other than the above-described aspect of the image shown in FIG. 26 are the same as those of the image shown in FIG. 8.

Aspects other than the above-described aspect of the process shown in FIG. 20 are the same as those of the process shown in FIG. 7.

The measurement endoscope apparatus 1a may have a mechanism for moving the distal end 20 of the endoscope insertion unit 2 back and forth in the axial direction. In this case, when it is determined in step S165 that the point on the subject at the estimated 3-dimensional coordinates of the measurement point is not included in the field of view of the first optical system 31, the measurement endoscope apparatus 1a may automatically separate the distal end 20 of the endoscope insertion unit 2 from the subject.

In FIG. 20, steps S165 and S175 are not essential. For example, after the process of step S160 is performed, the process of step S170 may be performed without performing the process of step S165.

In FIG. 20, step S130 may be changed to step S130a in FIG. 11, and step S135 may be changed to step S135a in FIG. 11. Alternatively, in FIG. 20, step S130 may be changed to steps S130b, S130c, and S130d in FIG. 14, and step S135 may be changed to step S135b in FIG. 14.

According to the second embodiment, the measurement endoscope apparatus 1a includes the endoscope insertion unit 2, the first optical system 31 (a first imaging optical system), the second optical system 32 (a second imaging optical system), the imaging element 21, the measurement processing unit 43, the bending unit 22, the reliability determination unit 44, and the bending control unit 452. The measurement endoscope apparatus 1a includes the notification control unit 451 and the measurement point checking unit 453 in addition to these components. In the second embodiment, the notification control unit 451 and the measurement point checking unit 453 are not essential.

In the second embodiment, the bending control unit 452 controls the bending unit 22 so that the distal end 20 of the endoscope insertion unit 2 is moved toward the first optical system 31 in the parallax direction when the reliability determination unit 44 determines that the reliability is low. In this way, it is possible to suppress a decrease in measurement accuracy due to the occurrence of occlusion.

When it is expected that the point on the subject at the estimated 3-dimensional coordinates of the measurement point is not included in the field of view of the first optical system 31 due to automatic bending of the endoscope insertion unit 2, the notification control unit 451 sends a notification to prompt the user to perform an operation of moving the distal end 20 of the endoscope insertion unit 2 away from the subject. In this way, it is possible to maintain an appropriate distance between the subject and the distal end 20 of the endoscope insertion unit 2.

Third Embodiment

Figure 27:
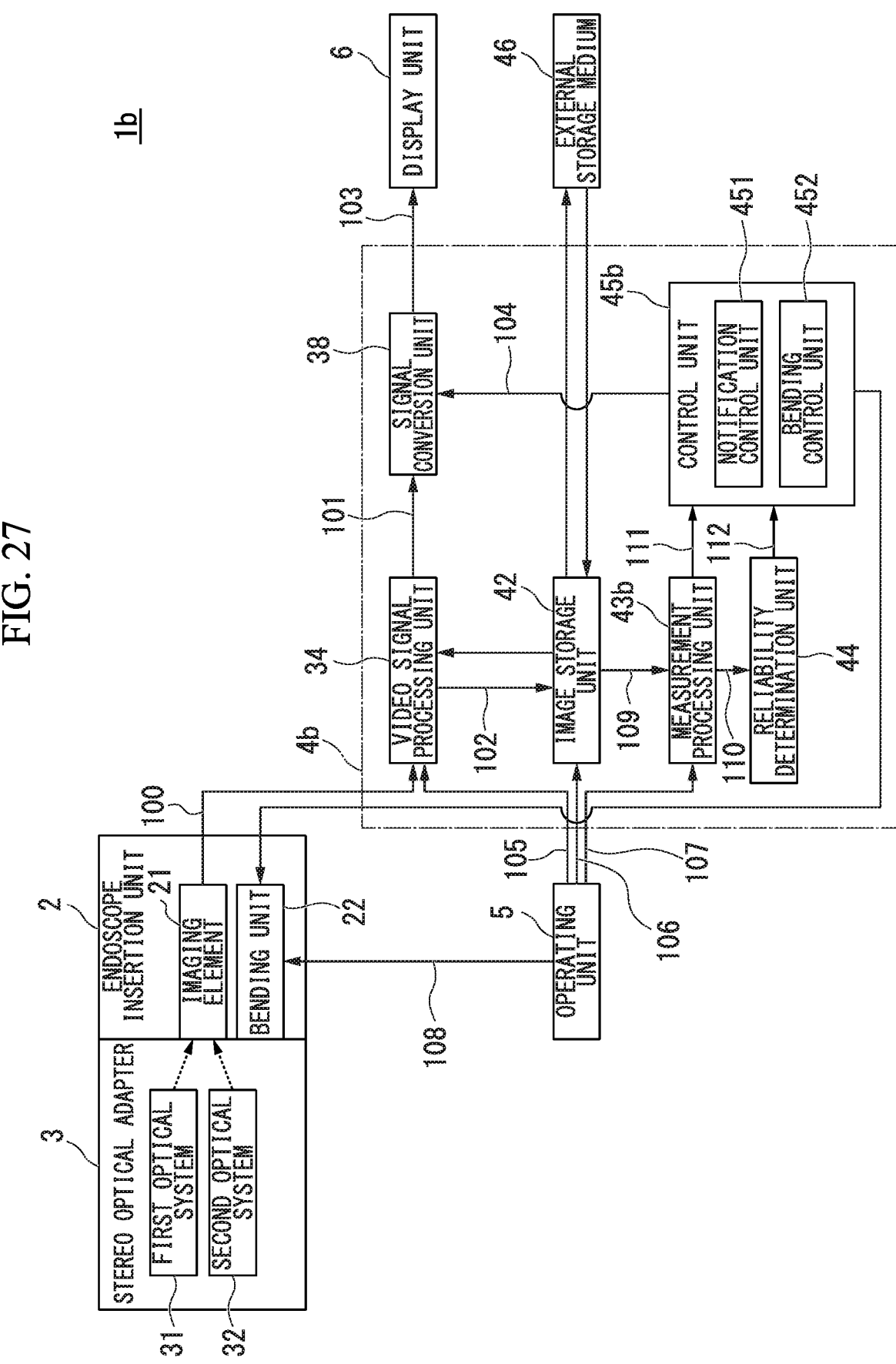
FIG. 27 is a block diagram showing a configuration of a measurement endoscope apparatus according to a third embodiment of the present invention.

In a third embodiment of the present invention, the measurement endoscope apparatus 1 of the first embodiment is changed to a measurement endoscope apparatus 1b shown in FIG. 27. An external view of the measurement endoscope apparatus 1b is similar to the external view of the measurement endoscope apparatus 1 shown in FIG. 1. The distal end 20 of the endoscope insertion unit 2 and the stereo optical adapter 3 have the same configuration as that shown in FIGS. 2 and 3.

FIG. 27 shows a configuration of the measurement endoscope apparatus 1b of the third embodiment. The difference between FIGS. 18 and 27 will be described.

The controller 4a shown in FIG. 18 is changed to a controller 4b. In the controller 4b, the measurement processing unit 43 in FIG. 18 is changed to a measurement processing unit 43b. Moreover, in the controller 4b, the control unit 45a in FIG. 18 is changed to a control unit 45b. The control unit 45b includes a notification control unit 451 and a bending control unit 452. The bending control unit 452 controls the bending unit 22 so that the distal end 20 of the endoscope insertion unit 2 is bent by a predetermined bending amount. The reliability determination unit 44 determines the reliability before and after control of the bending unit 22 based on the predetermined bending amount is performed.

Aspects other than the above-described aspect of the configuration shown in FIG. 27 are the same as those of the configuration shown in FIG. 18.

Figure 28:
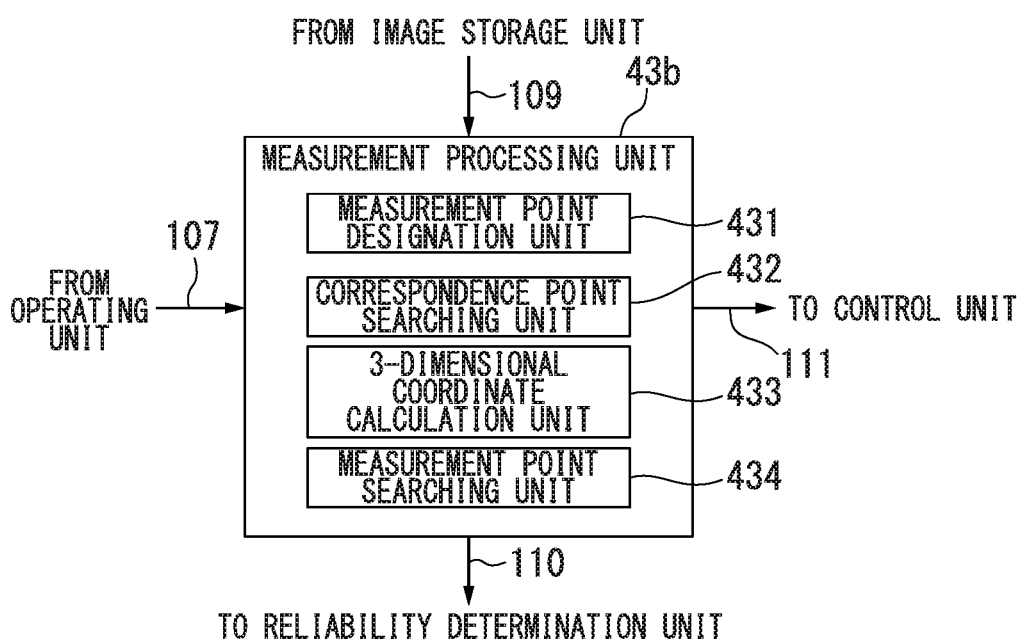
FIG. 28 is a block diagram showing a configuration of a measurement processing unit of the measurement endoscope apparatus according to the third embodiment of the present invention.

FIG. 28 shows a configuration of the measurement processing unit 43b. As shown in FIG. 28, the measurement processing unit 43b includes a measurement point designation unit 431, a correspondence point searching unit 432, a 3-dimensional coordinate calculation unit 433, and a measurement point searching unit 434. The difference between FIGS. 5 and 28 will be described.

The measurement point searching unit 434 processes at least a video signal (the image data 109) corresponding to the first image after control of the bending unit 22 based on the predetermined bending amount is performed. In this way, the measurement point searching unit 434 searches for the same position as the position of the measurement point designated before the control of the bending unit 22 based on the predetermined bending amount is performed. Furthermore, the measurement point searching unit 434 sets the measurement point to the position searched for.

In the second embodiment, the bending amount necessary for avoiding occlusion is calculated, and control of bending the distal end 20 of the endoscope insertion unit 2 by the bending amount is performed. However, in a soft endoscope, since the rigidity of the endoscope insertion unit 2 changes with time, it may be difficult to control a desired bending amount. In a soft endoscope, since a bending amount for the same driving amount is different depending on a bending state of the endoscope insertion unit 2 when bending starts, it may be difficult to control a desired bending amount. In the third embodiment, a process of bending the distal end 20 of the endoscope insertion unit 2 by a very small amount and a process of determining whether or not occlusion has occurred are performed repeatedly by taking the difficulties into consideration. In this way, it is possible to avoid occlusion.

When the measurement point is set by the measurement point searching unit 434, the correspondence point searching unit 432 searches for a correspondence point of the second image corresponding to the measurement point. The reliability determination unit 44 determines the reliability again on the basis of the correspondence point corresponding to the measurement point searched for by the measurement point searching unit 434.

Aspects other than the above-described aspect of the configuration shown in FIG. 28 are the same as those of the configuration shown in FIG. 5.

Figure 29:
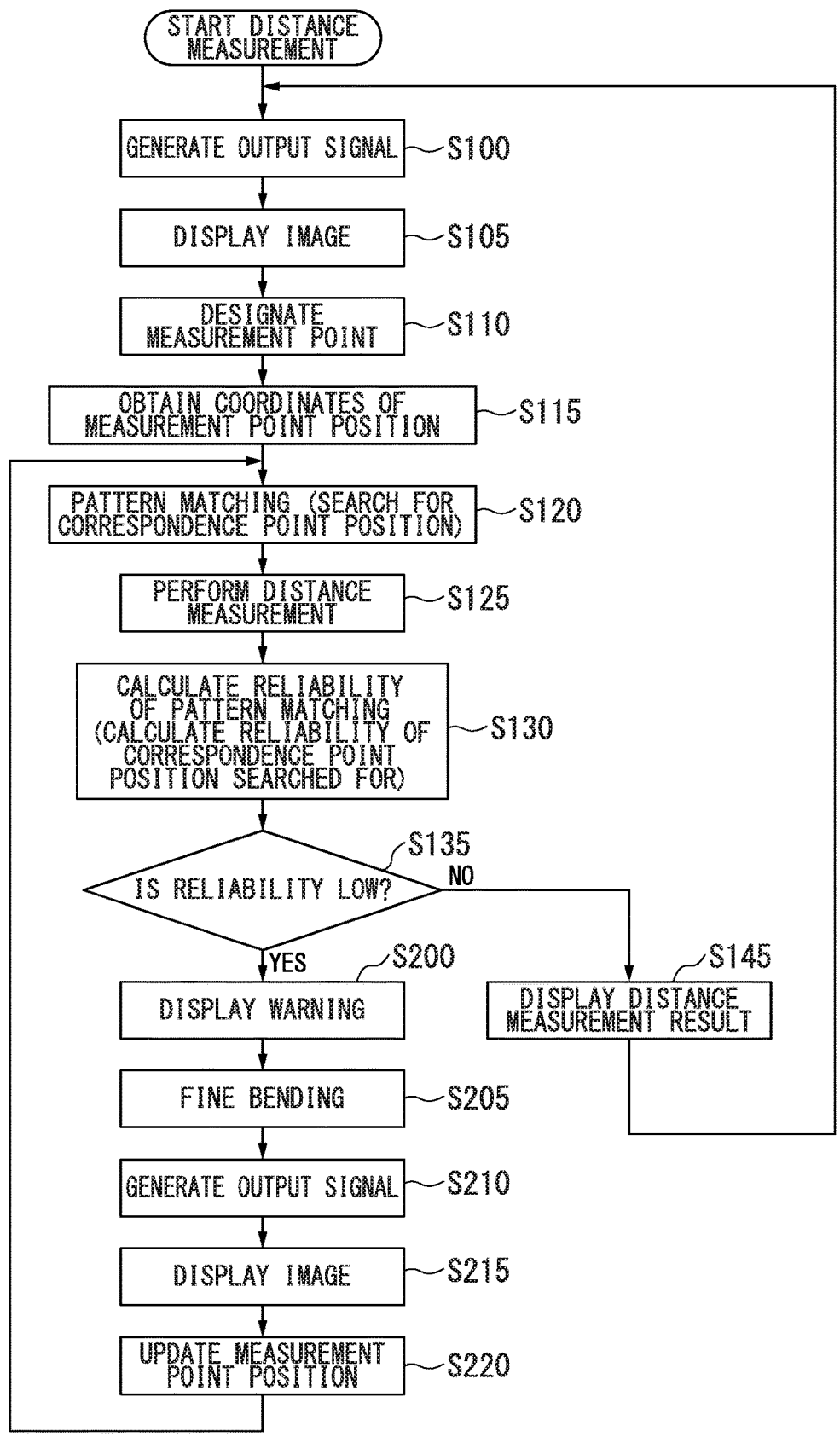
FIG. 29 is a flowchart showing the procedure of an operation of the measurement endoscope apparatus according to the third embodiment of the present invention.

FIG. 29 shows the procedure of an operation of the measurement endoscope apparatus 1b during distance measurement. The difference between FIGS. 7 and 29 will be described.

When it is determined in step S135 that the reliability is low, the notification control unit 451 outputs the measurement information 104 including a warning. In this way, the notification control unit 451 notifies the user of a warning. The signal conversion unit 38 generates the display video signal 103 by combining the measurement information 104 with the output video signal 101. The display unit 6 displays an image including a warning on the basis of the display video signal 103 (step S200). The warning includes a message that notifies the user of the fact that the distal end 20 of the endoscope insertion unit 2 is automatically bent.

Figure 30:
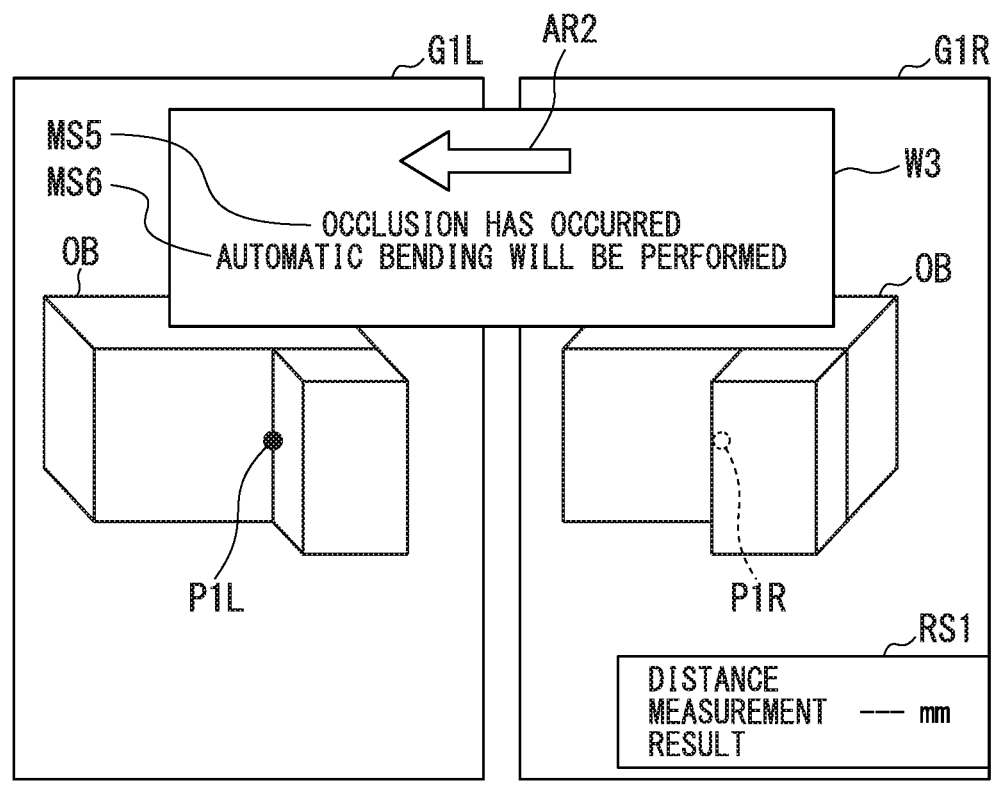
FIG. 30 is a reference diagram showing an image displayed by a display unit of the measurement endoscope apparatus according to the third embodiment of the present invention.

FIG. 30 shows an example of an image displayed by the display unit 6 in step S200. The difference between FIGS. 8 and 30 will be described. The display unit 6 displays a message window W3. The message window W3 includes a message MS5 indicating the occurrence of occlusion and a message MS6 indicating that the distal end 20 of the endoscope insertion unit 2 is automatically bent. Moreover, the message window W3 includes an arrow AR2 indicating the direction of automatic bending. The arrow AR2 indicates a leftward direction. The direction indicated by the arrow AR2 is the direction from the second optical system 32 toward the first optical system 31. Since the message MS6 and the arrow AR2 are displayed, the user can understand that the distal end 20 of the endoscope insertion unit 2 will be bent toward the left side automatically in order to avoid the occlusion. Aspects other than the above-described aspect of the image shown in FIG. 30 are the same as those of the image shown in FIG. 8.

After step S200 is performed, the bending control unit 452 controls the bending unit 22 so that the distal end 20 of the endoscope insertion unit 2 is moved toward the first optical system 31 in the parallax direction by a predetermined bending amount. In this way, the bending unit 22 moves the distal end 20 of the endoscope insertion unit 2 toward the first optical system 31 in the parallax direction (step S205). The predetermined bending amount may be a very small bending amount. For example, the predetermined bending amount is smaller than the distance between the first optical center of the first optical system 31 and the second optical center of the second optical system 32.

After step S205 is performed, the video signal processing unit 34 generates the output video signal 101 and the output video signal 102 from the imaging signal 100. The signal conversion unit 38 outputs the display video signal 103 based on the output video signal 101 to the display unit 6 (step S210). The imaging signal 100 used in step S210 is a signal that is newly output after the imaging signal 100 used in step S100 is output.

After step S210 is performed, the display unit 6 displays an image on the basis of the display video signal 103 (step S215). The image displayed in step S215 is similar to the image shown in FIG. 8. The image displayed in step S215 may include the message window W3 shown in FIG. 30.

After step S215 is performed, the measurement processing unit 43b detects a position, which is identical to the position of the measurement point in the first image in a previous frame, in the first image in the subsequent frame by processing two frames of image data 109. In this way, the measurement processing unit 43b searches for the same position as the position of the measurement point designated before the control of the bending unit 22 based on the predetermined bending amount is performed. That is, the measurement processing unit 43b searches for the position of the measurement point. Furthermore, the measurement processing unit 43b updates the measurement point by setting the measurement point to the position searched for (step S220). The measurement processing unit 43b corrects the position of an alignment mark so that the alignment mark is displayed at the position of the updated measurement point.

After step S220 is performed, the process of step S120 is performed. That is, the correspondence point searching unit 432 searches for the correspondence point of the second image corresponding to the updated measurement point. After the process of step S120 is performed, the processes of steps S125 and S130 are performed.

Furthermore, the determination process of step S135 is performed. In step S135, the reliability determination unit 44 determines the reliability on the basis of the correspondence point corresponding to the measurement point searched for by the measurement point searching unit 434.

Aspects other than the above-described aspect of the process shown in FIG. 29 are the same as those of the process shown in FIG. 7.

In FIG. 29, step S200 is not essential. For example, when it is determined in step S135 that the reliability is low, the process of step S205 may be performed without performing the process of step S200.

In FIG. 29, step S130 may be changed to step S130a in FIG. 11 and step S135 may be changed to step S135a in FIG. 11. Alternatively, in FIG. 29, step S130 may be changed to steps S130b, S130c, and S130d in FIG. 14 and step S135 may be changed to step S135b in FIG. 14.

According to the third embodiment, the measurement endoscope apparatus 1b includes the endoscope insertion unit 2, the first optical system 31 (a first imaging optical system), the second optical system 32 (a second imaging optical system), the imaging element 21, the measurement processing unit 43b, the bending unit 22, the reliability determination unit 44, and the bending control unit 452. The measurement endoscope apparatus 1b has the notification control unit 451 in addition to these components. In the third embodiment, the notification control unit 451 is not essential.

In the third embodiment, the bending control unit 452 controls the bending unit 22 so that the distal end 20 of the endoscope insertion unit 2 is moved toward the first optical system 31 in the parallax direction when the reliability determination unit 44 determines that the reliability is low. In this way, it is possible to suppress a decrease in measurement accuracy due to the occurrence of occlusion.

In the third embodiment, a process of bending the distal end 20 of the endoscope insertion unit 2 by a very small amount and a process of determining whether or not occlusion has occurred are performed repeatedly. Due to this, even when it is difficult to control a desired bending amount according to the state of the endoscope insertion unit 2, it is possible to avoid occlusion at the position of the measurement point designated by the user.

Modifications of First to Third Embodiments

Modifications of the first to third embodiments will be described. When the stereo optical adapter 3 shown in FIG. 3 is used, the first and second optical images are formed simultaneously on the light receiving surface 24 by the first and second optical systems 31 and 32. Due to this, the imaging element 21 generates the imaging signal 100 on the basis of the first and second optical images. However, a stereo optical adapter by which an optical path can be switched and the first and second optical images are alternately formed on the light receiving surface 24 may be used.

Figure 31:
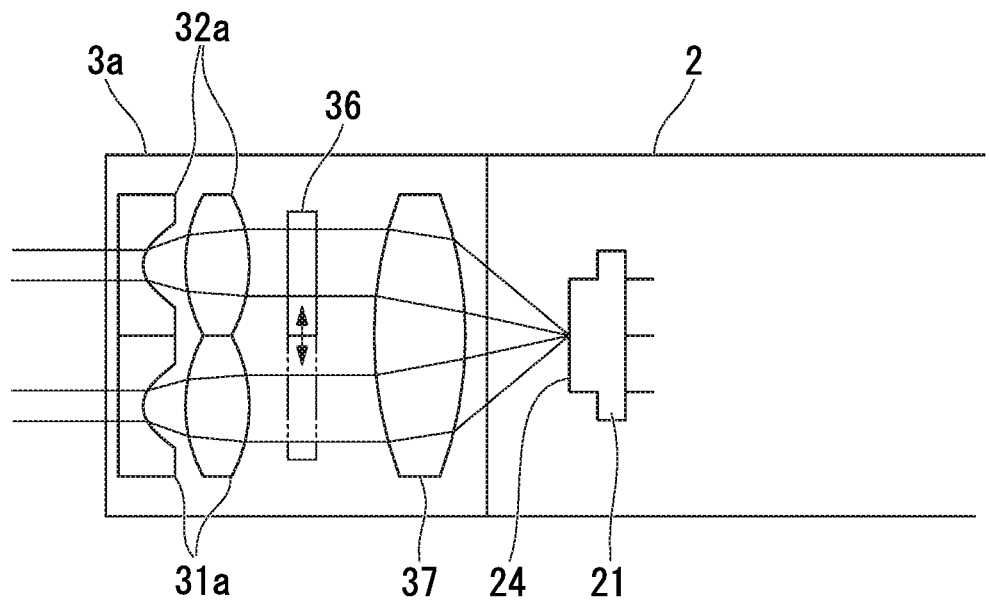
FIG. 31 is a block diagram showing a configuration of a stereo optical adapter of a measurement endoscope apparatus according to a modification of the first to third embodiments of the present invention.

FIG. 31 shows a configuration of a stereo optical adapter 3a capable of switching an optical path. The imaging element 21 is disposed in the distal end 20 of the endoscope insertion unit 2. The stereo optical adapter 3a is attached to the distal end 20 of the endoscope insertion unit 2. The stereo optical adapter 3a includes a first optical system 31a, a second optical system 32a, a mechanical shutter 36, and a lens 37.

The first optical system 31a is disposed in a first optical path. The second optical system 32a is disposed in a second optical path. The mechanical shutter 36 can move in an arrangement direction of the first and second optical systems 31a and 32a. The mechanical shutter 36 is disposed on one of the first and second optical paths. For example, when the mechanical shutter 36 is disposed in the second optical path, light having passed through the second optical system 32a is blocked by the mechanical shutter 36. Due to this, light having passed through the first optical system 31a and the lens 37 only is incident on the light receiving surface 24 of the imaging element 21. Moreover, when the mechanical shutter 36 is disposed on the first optical path, light having passed through the first optical system 31a is blocked by the mechanical shutter 36. Due to this, light having passed through the second optical system 32a and the lens 37 only is incident on the light receiving surface 24 of the imaging element 21.

When the mechanical shutter 36 is disposed on the second optical path, the first optical image is formed on the light receiving surface 24 of the imaging element 21 by the light having passed through the first optical system 31a and the lens 37. The imaging element 21 generates the imaging signal 100 based on the first optical image. When the mechanical shutter 36 is disposed on the first optical path, the second optical image is formed on the light receiving surface 24 of the imaging element 21 by the light having passed through the second optical system 32a and the lens 37. The imaging element 21 generates the imaging signal 100 based on the second optical image.

Fourth Embodiment

In the first to third embodiments of the present invention, the stereo optical adapter 3 and the distal end 20 of the endoscope insertion unit 2 shown in FIG. 3 are used. In the first to third embodiments, the first and second optical images are formed simultaneously on the light receiving surface 24 by the first and second optical systems 31 and 32. The imaging element 21 generates the imaging signal 100 based on the first and second optical images. The measurement endoscope apparatuses 1, 1a, and 1b perform 3-dimensional measurement based on the optical images obtained via two imaging optical systems. The measurement method used in the first to third embodiments is called a passive stereo method. However, a measurement method called an active stereo method may be applied to a measurement endoscope apparatus. The fourth embodiment of the present invention relates to a measurement endoscope apparatus to which an active stereo method is applied. The measurement method used in the fourth embodiment is a phase shift method which is one of active stereo methods.

Figure 32:
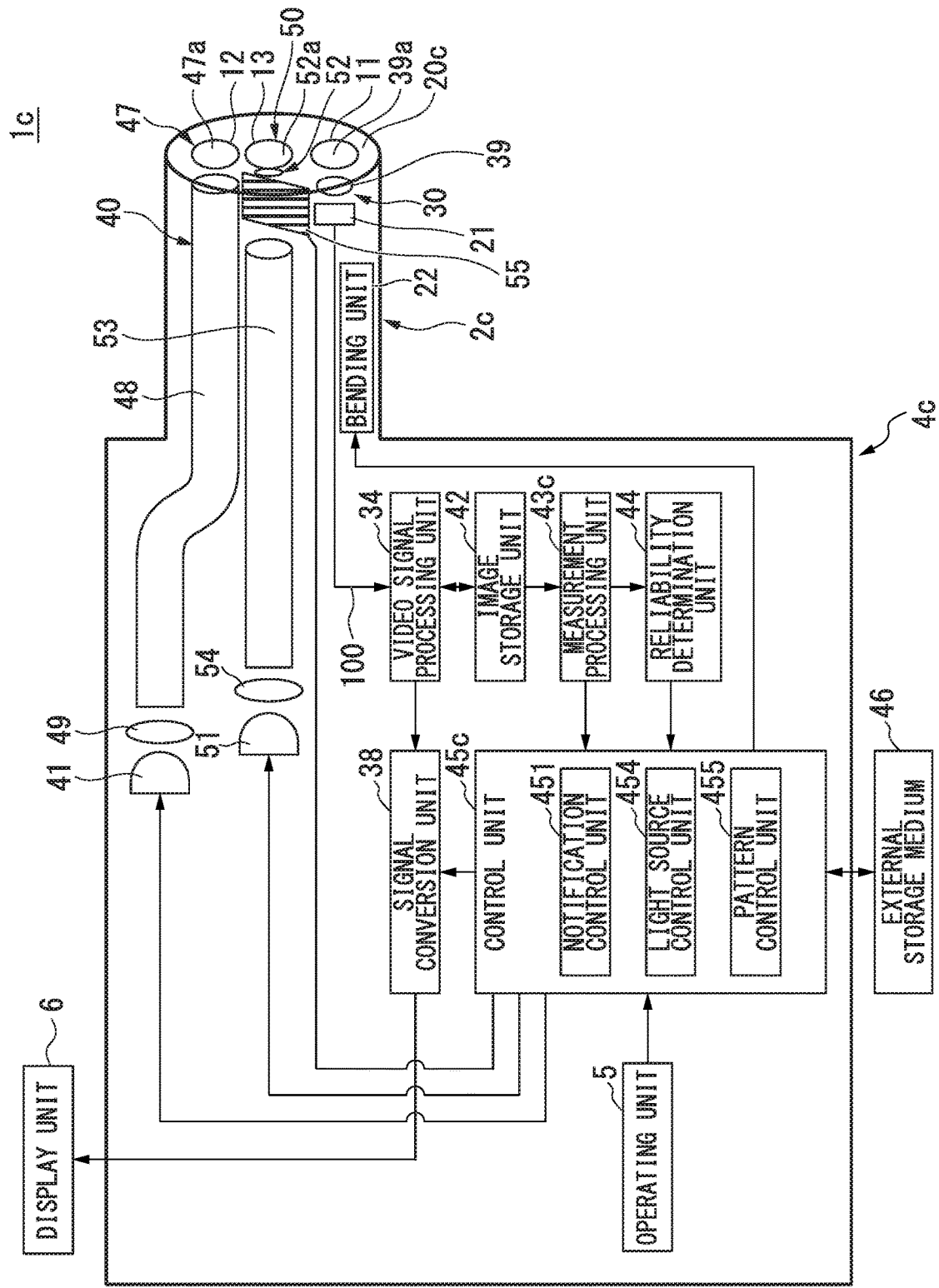
FIG. 32 is a block diagram showing a configuration of a measurement endoscope apparatus according to a fourth embodiment of the present invention.

In the fourth embodiment of the present invention, the measurement endoscope apparatus 1 of the first embodiment is changed to a measurement endoscope apparatus 1c shown in FIG. 32. FIG. 32 shows a configuration of the measurement endoscope apparatus 1c of the fourth embodiment. The difference between FIGS. 4 and 32 will be described.

The endoscope insertion unit 2 in FIG. 4 is changed to an endoscope insertion unit 2c and the controller 4 in FIG. 4 is changed to a controller 4c. In the controller 4c, the measurement processing unit 43 in FIG. 4 is changed to a measurement processing unit 43c and the control unit 45 in FIG. 4 is changed to a control unit 45c.

The endoscope insertion unit 2c includes an imaging unit 30, an illumination unit 40, a pattern projection unit 50, and a bending unit 22. The imaging unit 30 obtains the image of a subject. The illumination unit 40 illuminates an observation field of view on the front side of the endoscope insertion unit 2c. The pattern projection unit 50 projects a periodic pattern on the subject. The pattern projection unit 50 projects a stripe pattern on the subject as a periodic pattern. The stripe pattern has a spatially periodic brightness distribution.

Figure 33:
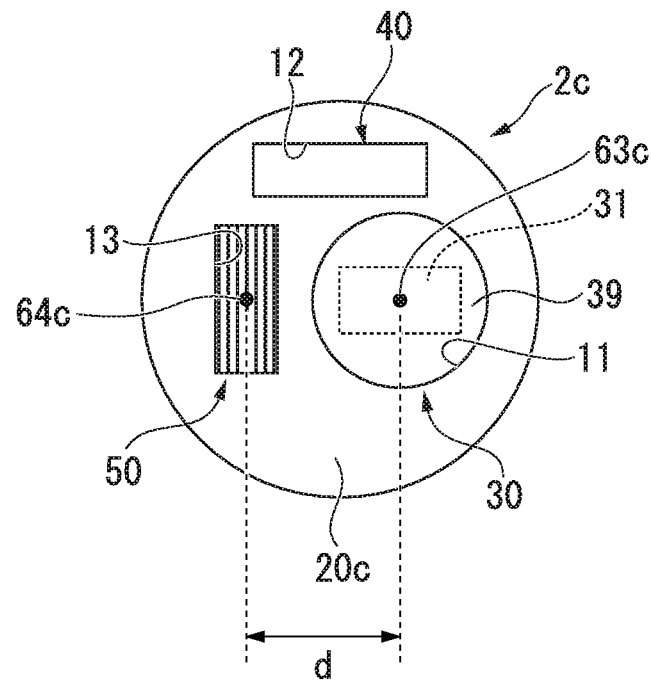
FIG. 33 is a front view of a distal end of an endoscope insertion unit of the measurement endoscope apparatus according to the fourth embodiment of the present invention.

FIG. 33 shows the front surface of a distal end 20c of the endoscope insertion unit 2c. As shown in FIG. 33, an opening 11, an illumination window 12, and a projection window 13 are formed in the distal end 20c of the endoscope insertion unit 2c. The opening 11 allows external light to enter the imaging optical system 39 of the imaging unit 30. The illumination window 12 radiates illumination light from the illumination unit 40 on the front side of the endoscope insertion unit 2c. The projection window 13 radiates the stripe pattern from the pattern projection unit 50 on the front side of the endoscope insertion unit 2c.

The imaging unit 30 has an imaging element 21 and an imaging optical system 39. The imaging element 21 is disposed in the distal end 20c of the endoscope insertion unit 2c. The imaging optical system 39 is disposed on the front side of the imaging element 21 at the distal end 20c of the endoscope insertion unit 2c. The imaging optical system 39 is disposed in the opening 11 of the endoscope insertion unit 2c. The imaging optical system 39 includes an objective lens. In the distal end 20c of the endoscope insertion unit 2c, the imaging optical system 39 is disposed at a position different from the position where the projection optical system 52 is disposed. The imaging optical system 39 allows reflection light within an observation field of view to enter the imaging element 21 and forms an optical image of the subject. The imaging optical system 39 has a light-transmitting cover member 39a that seals the opening 11.

The illumination unit 40 includes a first light source 41, an illumination optical system 47, a first fiber bundle 48, and a first incidence optical system 49. The first light source 41 is a light source that generates white light. The first light source 41 is disposed inside the controller 4c. The light generated by the first light source 41 is used as illumination light for illuminating the subject. The first fiber bundle 48 guides light generated by the first light source 41 to the illumination optical system 47. The first incidence optical system 49 is disposed between the first light source 41 and the first fiber bundle 48. The first incidence optical system 49 allows the light generated by the first light source 41 to enter the first fiber bundle 48.

The illumination optical system 47 is disposed in the distal end 20c of the endoscope insertion unit 2c. The illumination optical system 47 has a light-transmitting cover member 47a and a lens group that is not shown. The cover member 47a is disposed in the illumination window 12 of the endoscope insertion unit 2c. The illumination optical system 47 illuminates an observation field of view by allowing the light generated by the first light source 41 to be emitted from the illumination window 12. The first light source 41 may be disposed in the distal end 20c of the endoscope insertion unit 2c. In this case, the first fiber bundle 48 and the first incidence optical system 49 are not necessary.

The pattern projection unit 50 includes a second light source 51, a projection optical system 52, a second fiber bundle 53, a second incidence optical system 54, and a pattern generation unit 55. The second light source 51 is a light source that generates light different from the light generated by the first light source 41. The second light source 51 is disposed inside the controller 4c. The light generated by the second light source 51 is used as projection light for projecting a stripe pattern. The second fiber bundle 53 guides the light generated by the second light source 51 to the projection optical system 52. The second incidence optical system 54 is disposed between the second light source 51 and the second fiber bundle 53. The second incidence optical system 54 allows the light generated by the second light source 51 to enter the second fiber bundle 53. The pattern generation unit 55 is disposed on an optical path of the light emitted from the second light source 51. The pattern generation unit 55 generates a periodic pattern.

The projection optical system 52 is disposed in the distal end 20c of the endoscope insertion unit 2c. The projection optical system 52 includes a projection lens. The projection optical system 52 has a light-transmitting cover member 52a provided in the projection window 13 of the endoscope insertion unit 2c. As shown in FIG. 33, when the front surface of the distal end 20c of the endoscope insertion unit 2c is seen, the center of the projection window 13 is identical to the second optical center 64c of the projection optical system 52, and the center of the opening 11 is identical to the first optical center 63c of the imaging optical system 39. When the front surface of the distal end 20c of the endoscope insertion unit 2c is seen, the center of the projection window 13 is separated from the center of the opening 11 by a distance d. That is, the position where the projection optical system 52 is disposed is different from the position where the imaging optical system 39 is disposed. The second light source 51 may be disposed in the distal end 20c of the endoscope insertion unit 2c. In this case, the second fiber bundle 53 and the second incidence optical system 54 are not necessary.

Figure 34:
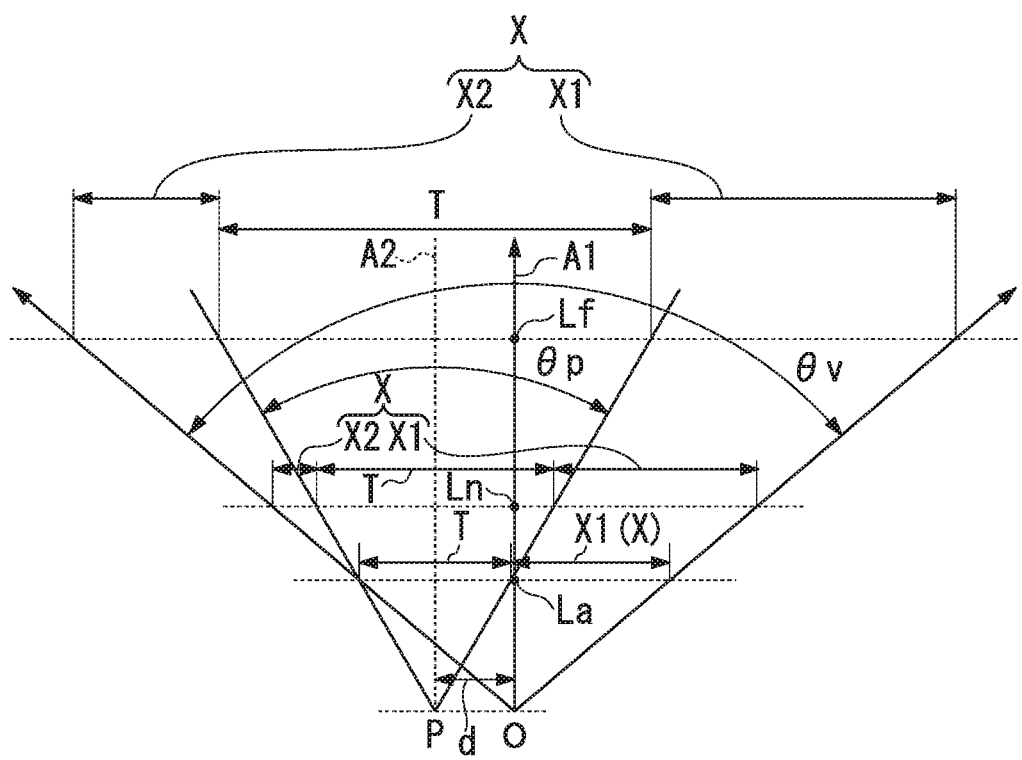
FIG. 34 is a schematic diagram showing the relation between an angle of view of an imaging optical system and a projection angle of a projection optical system of the measurement endoscope apparatus according to the fourth embodiment of the present invention.

FIG. 34 shows the relation between the angle of view of the imaging optical system 39 and the projection angle of the projection optical system 52. In FIG. 34, the position O of the imaging optical system 39 and the position P of the projection optical system 52 are shown. The position O is the position of a first optical center 63c of the imaging optical system 39. The position P is the position of a second optical center 64c of the projection optical system 52. The angle of view θv of the imaging optical system 39 spreads at an equal angle around a center line A1 extending in the optical axis direction of the imaging optical system 39. Moreover, the projection angle θp of the projection optical system 52 spreads at an equal angle around a center line A2 parallel to the center line A1. When the depth on a near point side of the imaging optical system 39 is Ln and the depth on a far point side is Lf, the shortest object distance La at which all projected stripes fall within the field of view satisfies a condition of Ln≥La. When an in-focus state is created (that is, the object distance is within the depth between Ln and Lf), the stripe pattern is positioned in the angle of view of the imaging optical system 39. Moreover, the distance d between the position O of the imaging optical system 39 and the position P of the projection optical system 52 is set to be smaller than the depth La which is the smallest value of a measurable object distance. Due to this, the distance d is sufficiently smaller than the object distance Ln. Therefore, the position of the stripe appearing in an image does not change greatly as long as the imaging unit 30 is in an in-focus state.

The pattern generation unit 55 is disposed in the distal end 20c of the endoscope insertion unit 2c. The pattern generation unit 55 is an element that forms a stripe pattern. For example, the pattern generation unit 55 is a slit plate having a plurality of slits. The pattern generation unit 55 may be a transparent plate which is formed of glass, a resin, or the like and on which a stripe pattern is drawn. The pattern generation unit 55 may be a liquid crystal shutter module capable of switching between a light-transmitting state and a non-light-transmitting state in respective liquid crystal elements. The pattern generation unit 55 may be a micro electro mechanical systems (MEMS) mirror module having a fine reflection mirror.

Figure 35:
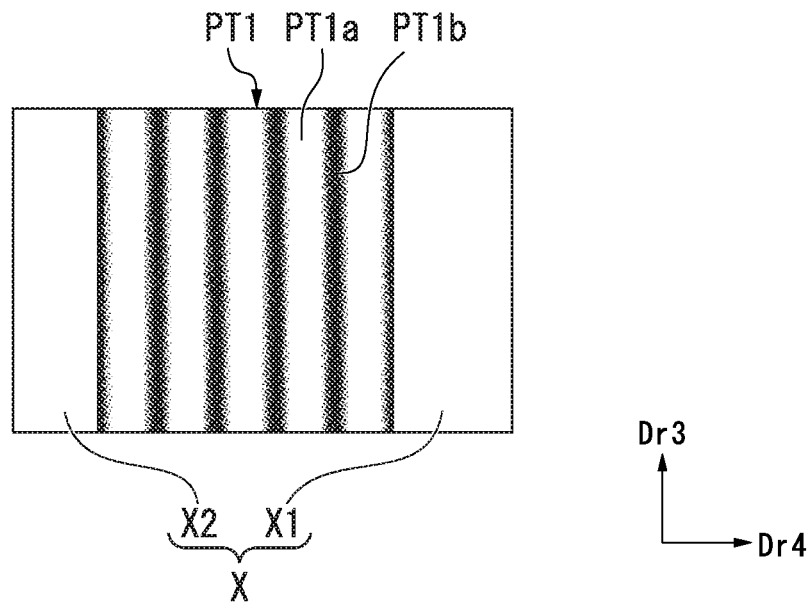
FIG. 35 is a reference diagram showing a stripe pattern projected on a subject according to the fourth embodiment of the present invention.

FIG. 35 shows a stripe pattern PT1 projected by the projection optical system 52. The stripe pattern PT1 includes a bright first portion PT1a and a dark second portion PT1b. The first and second portions PT1a and PT1b are long and narrow in a first direction Dr3 and are alternately arranged in a second direction Dr4 vertical to the first direction Dr3. That is, the stripe pattern PT1 is a pattern in which bright and dark patterns are periodically arranged in the second direction Dr4. Furthermore, the light intensity of the stripe pattern PT1 changes in a sinusoidal form in the second direction Dr4. The second direction Dr4 is a pattern arrangement direction. When the stripe pattern is projected on a plane that directly faces the distal end 20c of the endoscope insertion unit 2c, the stripe pattern PT1 shown in FIG. 34 appears on the plane.

The angle of view θv of the imaging optical system 39 and the projection angle θp of the projection optical system 52 satisfy the relation shown in FIG. 34. When the stripe pattern PT1 is projected on a subject, a region X on which the stripe pattern is not projected is formed at both ends in the second direction Dr4 in which the stripes of the stripe pattern are arranged within the imaging field of view of the imaging unit 30. The region X includes a right-side region X1 and a left-side region X2.

The pattern generation unit 55 sequentially generates a plurality of periodic patterns having different spatial phases according to the control of the pattern control unit 455 of the control unit 45c. The phase of the stripe pattern PT1 shown in FIG. 35 is the position of the first and second portions PT1a and PT1b in the second direction Dr4. The projection optical system 52 sequentially projects a plurality of periodic patterns having different spatial phases on the subject. For example, the projection optical system 52 projects at least three periodic patterns having different spatial phases on the subject. The imaging optical system 39 sequentially forms a plurality of optical images of the subject on which the plurality of patterns are projected. The imaging element 21 sequentially generates a plurality of imaging signals 100 based on the plurality of optical images formed sequentially on the light receiving surface 24 via the imaging optical system 39. That is, the imaging element 21 generates a plurality of images corresponding to a plurality of optical images obtained via the imaging optical system 39.

The measurement processing unit 43c sets a measurement point in at least one of the plurality of images generated by the imaging element 21 and calculates the 3-dimensional coordinates of the measurement point by a phase shift method using the plurality of images. The measurement processing unit 43c performs a measurement process by the principle of triangulation on the basis of the images generated by the imaging element 21 and the camera parameters of a first position and a second position different from the first position. The first position is the position of the first optical center 63c of the imaging optical system 39. The second position is the position of the second optical center 64c of the projection optical system 52. Moreover, the camera parameters may include a position parameter of the first position and a position parameter of the second position or may include a distance parameter of the distance between the first and second positions.

The control unit 45c includes a notification control unit 451, a light source control unit 454, and a pattern control unit 455. The light source control unit 454 controls the turning on/off of the first and second light sources 41 and 51.

The pattern control unit 455 shifts the spatial phase of the pattern generated by the pattern generation unit 55. For example, when the pattern generation unit 55 is configured as a slit plate or a plate on which a stripe pattern is drawn, the pattern control unit 455 shifts the spatial phase of the pattern by moving the pattern generation unit 55 in the pattern arrangement direction. When the pattern generation unit 55 is configured as a liquid crystal shutter module or a MEMS mirror module, the pattern control unit 455 shifts the spatial phase of the pattern by controlling the state of a liquid crystal element or a reflection mirror. When the pattern control unit 455 shifts the spatial phase of the pattern, the stripe pattern PT1 shown in FIG. 34 moves in the second direction Dr4 or the opposite direction. The notification control unit 451 sends a notification to prompt the user to perform a bending operation of bending the distal end 20c of the endoscope insertion unit 2c so that the distal end 20c of the endoscope insertion unit 2c is moved in a direction from the projection optical system 52 toward the imaging optical system 39 when the reliability determination unit 44 determines that the reliability is low. In other words, the notification control unit 451 sends a notification to prompt the user to perform an operation of moving the distal end 20c of the endoscope insertion unit 2c in a direction from the projection optical system 52 toward the imaging optical system 39 when the reliability determination unit 44 determines that the reliability is low. In other words, the notification control unit 451 sends a notification to prompt the user to perform an operation of moving the distal end 20c of the endoscope insertion unit 2c in a direction from the position (the second position) of the second optical center 64c of the projection optical system 52 toward the position (the first position) of the first optical center 63c of the imaging optical system 39 when the reliability determination unit 44 determines that the reliability is low.

Figure 36:
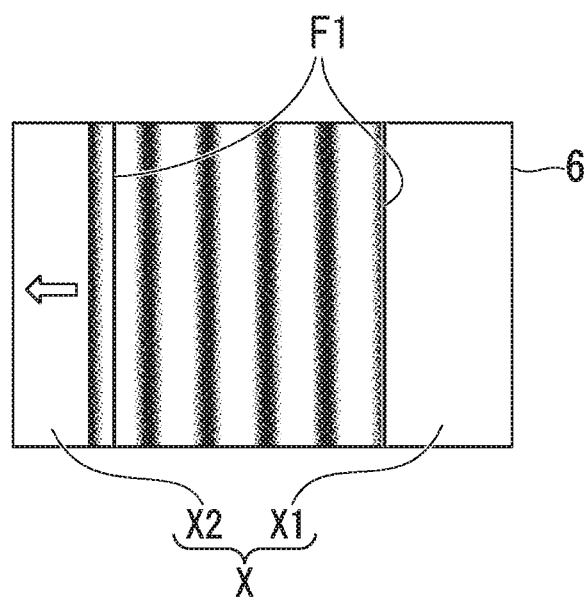
FIG. 36 is a reference diagram showing an image displayed by a display unit of the measurement endoscope apparatus according to the fourth embodiment of the present invention.
Figure 37:
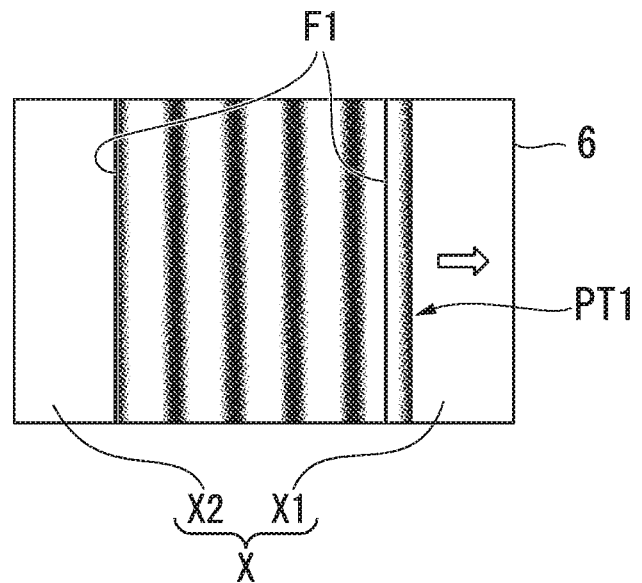
FIG. 37 is a reference diagram showing an image displayed by the display unit according to the measurement endoscope apparatus according to the fourth embodiment of the present invention.

FIGS. 36 and 37 show an image displayed on the display unit 6. The control unit 45c generates an image of a frame F1 indicating a scheduled position at which the stripe pattern PT1 is projected on the subject. A region of the image surrounded by the frame F1 is a target region T (FIG. 34) of 3-dimensional measurement. The position of the frame F1 is set so as to surround at least a portion of the region in which the stripe pattern PT1 is displayed even when the stripe pattern PT1 is moved in a horizontal direction to the maximum extent. In this way, at least a portion of the stripe pattern PT1 is positioned inside the frame F1 regardless of the actual position of the stripe pattern PT1 in the image displayed on the display unit 6. The display unit 6 displays the image of the subject and the frame F1 on a display screen.

The measurement processing unit 43c and the control unit 45c are configured as one or a plurality of processors. The measurement processing unit 43c and the control unit 45c may be configured as an ASIC or an FPGA.

Aspects other than the above-described aspect of the configuration shown in FIG. 32 are the same as those of the configuration shown in FIG. 4.

The operation of the measurement endoscope apparatus 1c will be described. The mode of the measurement endoscope apparatus 1c includes an observation mode and a measurement mode. The observation mode is a mode for observing a desired portion of a subject. The measurement mode is a mode for measuring a three-dimensional shape of a subject. A user can switch between the observation mode and the measurement mode as necessary by operating the operating unit 5.

When an instruction to set the mode to the measurement mode is input by the user, a control signal for displaying the image of the frame F1 on the display unit 6 is output from the control unit 45c to the video signal processing unit 34. In this way, the image of the frame F1 is displayed on the display unit 6. In this state, the stripe pattern PT1 is not yet projected. In this state, the user can observe the subject illuminated by the illumination light. The user adjusts the position and the like of the endoscope insertion unit 2c so that a desired portion of the subject of which the 3-dimensional shape is to be measured falls within the frame F1 displayed on the display unit 6. The user starts measurement of the 3-dimensional shape by operating the operating unit 5 in a state in which the measurement target portion is positioned in the frame F1.

When measurement of the 3-dimensional shape starts, at least one image is obtained by the imaging element 21 in a state in which illumination light from the illumination unit 40 is emitted. Subsequently, generation of illumination light by the first light source 41 of the illumination unit 40 is stopped by the light source control unit 454 and generation of projection light by the second light source 51 of the pattern projection unit 50 is started by the light source control unit 454. The projection light generated by the second light source 51 passes through the pattern generation unit 55 and the projection optical system 52. The stripe pattern is projected on a subject by the projection optical system 52.

The imaging element 21 generates an image of the subject in a state in which the stripe pattern is projected on the subject. The image of the subject on which the stripe pattern is projected is processed by the video signal processing unit 34 and is stored in the image storage unit 42. The pattern control unit 455 sequentially changes the phase of the stripe pattern projected on the subject. In this way, the pattern generation unit 55 sequentially generates a plurality of stripe patterns having different spatial phases, and the projection optical system 52 sequentially projects the plurality of stripe patterns on the subject. The imaging unit 30 generates a plurality of images by sequentially imaging the plurality of stripe patterns. The measurement processing unit 43c calculates the phase of the stripe pattern appearing in the plurality of images generated by the imaging unit 30 by a temporal phase shift method and performs measurement of the 3-dimensional shape of the subject.

In the fourth embodiment, the plurality of images include the region X on which the stripe pattern is not projected. Due to this, the measurement processing unit 43c can correlate a stripe appearing in an image and the stripe of the stripe pattern projected on the subject relatively easily on the basis of the boundary between the region X and a region on which the stripe pattern is projected. In this way, the measurement processing unit 43c can calculate the 3-dimensional coordinates on an actual space from the calculated phase. The measurement processing unit 43c can calculate the 3-dimensional shape of the subject by generating a distribution of 3-dimensional coordinates. When the measurement result is displayed on the display unit 6, the user can understand the 3-dimensional shape of the subject in the frame F1.

Figure 38:
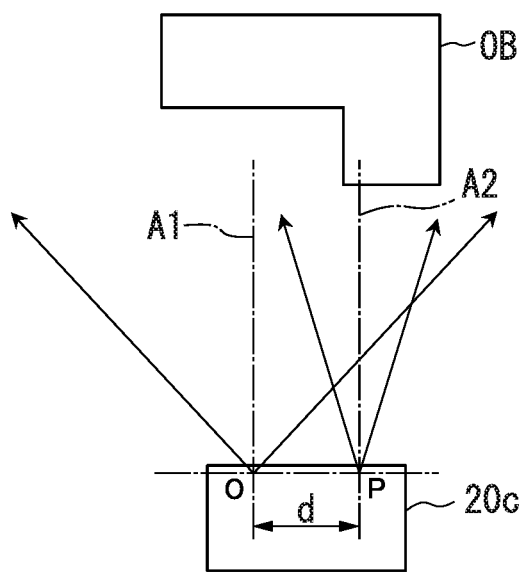
FIG. 38 is a reference diagram showing the positions of a subject and the distal end of the endoscope insertion unit of the measurement endoscope apparatus according to the fourth embodiment of the present invention.

FIG. 38 schematically shows the positions of the subject OB and the distal end 20c of the endoscope insertion unit 2c. FIG. 38 shows a state in which the subject OB and the distal end 20c of the endoscope insertion unit 2c are projected on the xz-plane shown in FIG. 6. A point on the space in FIG. 38 is shown as a point projected on the xz-plane. In the measurement endoscope apparatus 1c, the position O of the first optical center 63c of the imaging optical system 39 and the position P of the second optical center 64c of the projection optical system 52 are separated by the distance d. Due to this, the subject OB seen at the position O is different from that seen at the position P.

Figure 39:
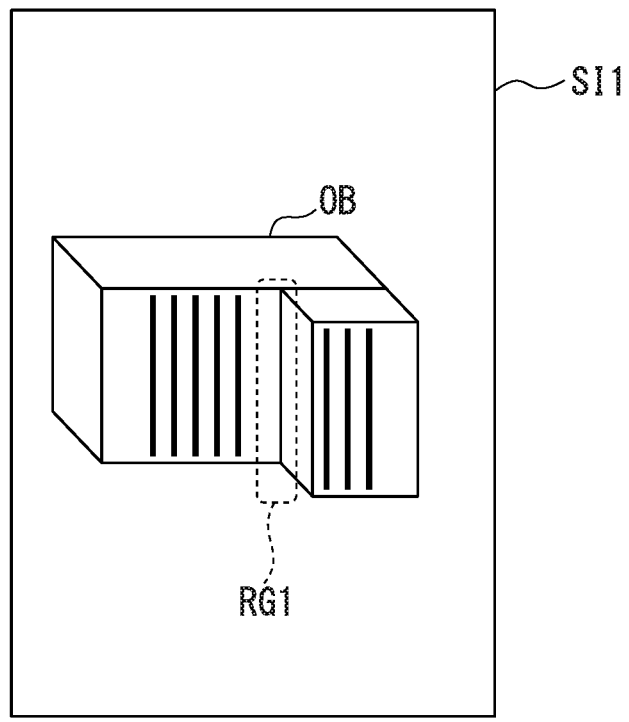
FIG. 39 is a reference diagram showing a subject image seen from an optical center of an imaging optical system of the measurement endoscope apparatus according to the fourth embodiment of the present invention.
Figure 40:
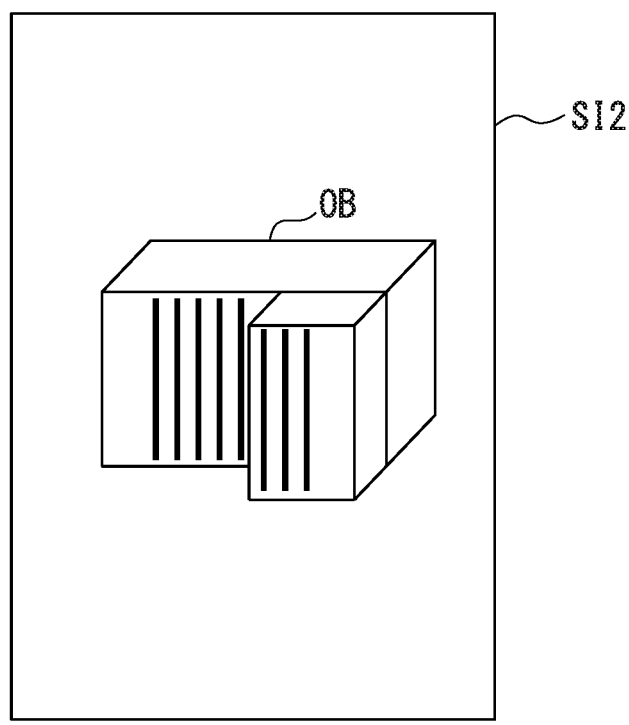
FIG. 40 is a reference diagram showing a subject image seen from the optical center of the projection optical system of the measurement endoscope apparatus according to the fourth embodiment of the present invention.

FIG. 39 shows a subject image SI1 seen from the first optical center 63c (the position O) of the imaging optical system 39 when the stripe pattern is projected on the subject OB. FIG. 40 shows a subject image SI2 seen from the second optical center 64c (the position P) of the projection optical system 52 when the stripe pattern is projected on the subject OB. As shown in FIG. 39, a region RG1 on which the stripe pattern is not projected is formed on the surface of the subject OB that is visible in the subject image SI1. This is a state in which occlusion occurs in the fourth embodiment. The moving direction of the distal end 20c of the endoscope insertion unit 2c for avoiding occlusion is the direction from the projection optical system 52 toward the imaging optical system 39. The moving direction of the distal end 20c of the endoscope insertion unit 2c may not be perfectly identical to this direction. The moving direction of the distal end 20c of the endoscope insertion unit 2c has only to be a direction in which the projection optical system 52 approaches the position of the imaging optical system 39 before the distal end 20c of the endoscope insertion unit 2c is moved.

Figure 41:
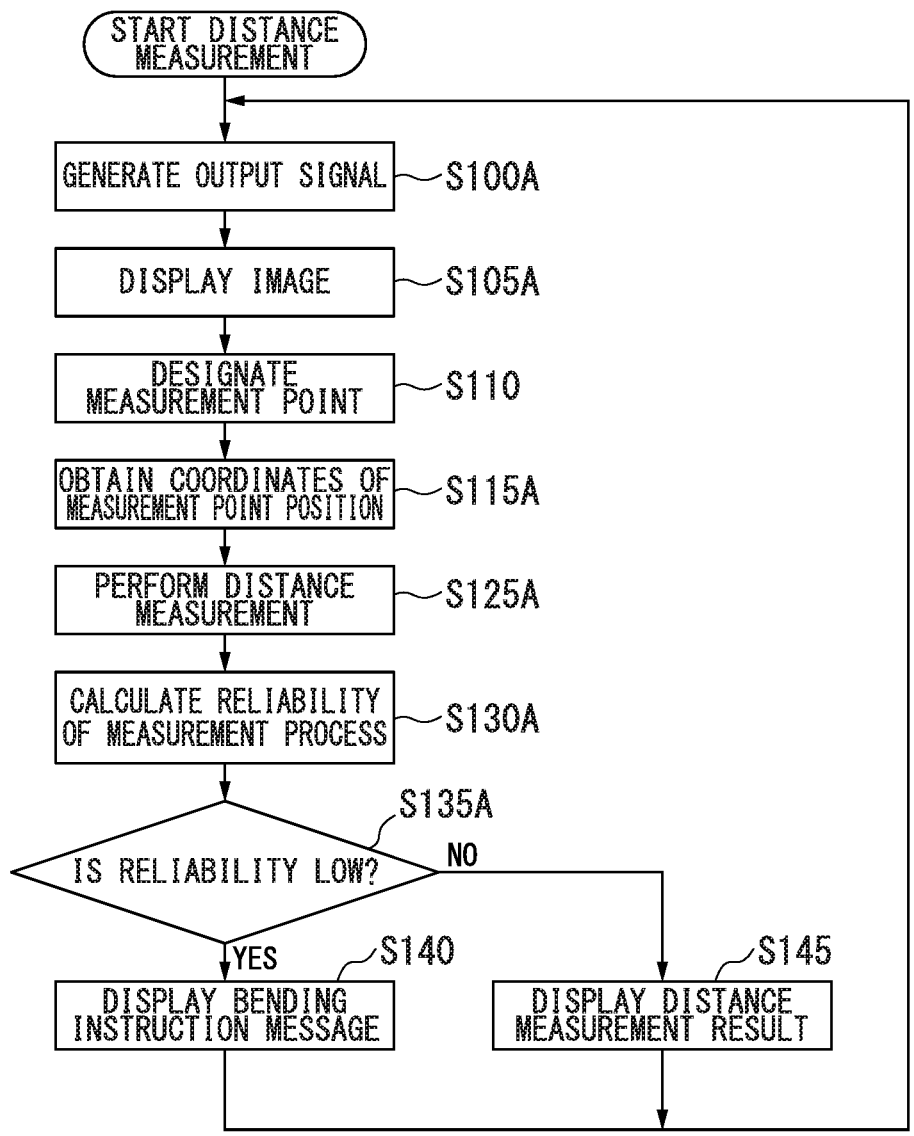
FIG. 41 is a flowchart showing the procedure of an operation of the measurement endoscope apparatus according to the fourth embodiment of the present invention.

FIG. 41 shows the procedure of an operation of the measurement endoscope apparatus 1c during distance measurement. The difference between FIGS. 7 and 41 will be described.

After distance measurement starts, the imaging element 21 generates an image in a state in which the illumination light from the first light source 41 is radiated on the subject by the illumination optical system 47. In this case, the stripe pattern is not projected on the subject. Furthermore, the imaging element 21 generates a plurality of images (pattern images) in a state in which the stripe pattern generated by the pattern generation unit 55 is projected on the subject by the projection optical system 52 (step S100A). Step S100A corresponds to step S100 in FIG. 7.

After step S100A is performed, the display unit 6 displays an image when the illumination light was radiated on the subject (step S105A). Step S105A corresponds to step S105 in FIG. 7.

After step S110 is performed, the measurement processing unit 43c sets a measurement point to at least one of the plurality of pattern images on the basis of the measurement point designated to the image when the illumination light was radiated on the subject. That is, the measurement processing unit 43c obtains the 2-dimensional coordinates of the position of the measurement point (step S115A). For example, in step S115A, the measurement point is set to one of the plurality of pattern images. In pattern images other than one pattern image to which the measurement point is set, points of the same coordinates as the coordinates of the measurement point are set. The points set to the pattern images other than one pattern image to which the measurement point is set may be regarded as the measurement point. That is, the measurement point may be set to a plurality of pattern images. The measurement processing unit 43c may set the measurement point to at least one of three pattern images. Step S115A corresponds to step S115 in FIG. 7.

After step S115A is performed, the measurement processing unit 43c performs a distance measurement process (step S125A). In step S125A, the 3-dimensional coordinates of the measurement point is calculated by the phase shift method using a plurality of images including the image to which the measurement point is set. For example, the measurement processing unit 43c calculates a phase on the basis of the pixel values at the coordinates of the measurement points of the plurality of pattern images and the same points as the measurement points. The measurement processing unit 43c calculates the 3-dimensional coordinates of the measurement point by the principle of triangulation on the basis of the calculated phase. In this way, the measurement processing unit 43c calculates an object distance. The 3-dimensional coordinate calculation unit 433 outputs measurement result information 111 including the calculated object distance to the control unit 45. Step S125A corresponds to step S125 in FIG. 7.

After step S125A is performed, the reliability determination unit 44 calculates the reliability of the measurement process (step S130A). For example, in step S130A, the reliability determination unit 44 calculates the reliability by calculating the difference between the maximum value and the minimum value of the pixel values at the coordinates of the measurement points of the plurality of pattern images and the same points as the measurement points. Step S130A corresponds to step S130 in FIG. 7.

After step S130A is performed, the reliability determination unit 44 determines whether or not the reliability calculated in step S130A is low (step S135A). For example, in step S135A, the reliability determination unit 44 determines whether or not the difference between the maximum and minimum values of the pixel values calculated in step S130A is smaller than a threshold. When the difference between the maximum and minimum values of the pixel values calculated in step S130A is smaller than the threshold, it is determined that the pattern is not projected on the position of the measurement point. Due to this, the reliability determination unit 44 determines that the reliability is low. In this case, the process of step S140 is performed. When the difference between the maximum and minimum values of the pixel values calculated in step S130A is larger than the threshold, the process of step S145 is performed. Step S135A corresponds to step S135 in FIG. 7.

Aspects other than the above-described aspect of the process shown in FIG. 41 are the same as those of the process shown in FIG. 7.

In step S105A, the display unit 6 displays an image when illumination light was radiated on the subject. When the user designates the measurement point to an image obtained when the illumination light was radiated on the subject, the user can designate the measurement point on an image in which the subject is highly visible. In step S105A, the display unit 6 may display the pattern image obtained when the stripe pattern was projected on the subject.

According to the fourth embodiment, the measurement endoscope apparatus 1c includes the endoscope insertion unit 2c, the projection optical system 52, the pattern control unit 455, the imaging optical system 39, the imaging element 21, the measurement processing unit 43c, the reliability determination unit 44, and the notification control unit 451.

The endoscope apparatus of the respective aspects of the present invention may not include a component corresponding to the illumination unit 40.

In the fourth embodiment, the notification control unit 451 sends a notification to prompt the user to perform a bending operation of bending the distal end 20c of the endoscope insertion unit 2c so that the distal end 20c of the endoscope insertion unit 2c is moved in a direction from the projection optical system 52 toward the imaging optical system 39 when the reliability determination unit 44 determines that the reliability is low. In this way, it is possible to suppress a decrease in measurement accuracy due to the occurrence of occlusion.

The measurement endoscope apparatus 1c may perform control similar to the control performed by the measurement endoscope apparatus 1a of the second embodiment. That is, when occlusion occurs, the measurement endoscope apparatus 1c may automatically bend the distal end 20c of the endoscope insertion unit 2c in a direction in which the occlusion is avoided. In this case, the control unit 45c has the bending control unit 452 shown in FIGS. 18 and 19. The bending control unit 452 controls the bending unit 22 so that the distal end 20c of the endoscope insertion unit 2c is moved in a direction from the projection optical system 52 toward the imaging optical system 39 when the reliability determination unit 44 determines that the reliability is low. In other words, the bending control unit 452 controls the bending unit 22 so that the distal end 20c of the endoscope insertion unit 2c is moved in a direction from the position (the second position) of the second optical center 64c of the projection optical system 52 toward the position (the first position) of the first optical center 63c of the imaging optical system 39 when the reliability determination unit 44 determines that the reliability is low.

The measurement endoscope apparatus 1c may perform control similar to the control performed by the measurement endoscope apparatus 1b of the third embodiment. That is, a process of bending the distal end 20c of the endoscope insertion unit 2c by a very small amount and a process of determining whether or not occlusion has occurred are performed repeatedly. In this case, the bending control unit 452 controls the bending unit 22 so that the distal end 20c of the endoscope insertion unit 2c is bent by a predetermined bending amount. The reliability determination unit 44 determines the reliability before and after the control of the bending unit 22 based on the predetermined bending amount is performed.

Fifth Embodiment

A fifth embodiment of the present invention relates to a measurement endoscope apparatus to which an active stereo method is applied. The measurement method of the fifth embodiment is one of active stereo methods and is a method of projecting a random pattern on a subject.

Figure 42:
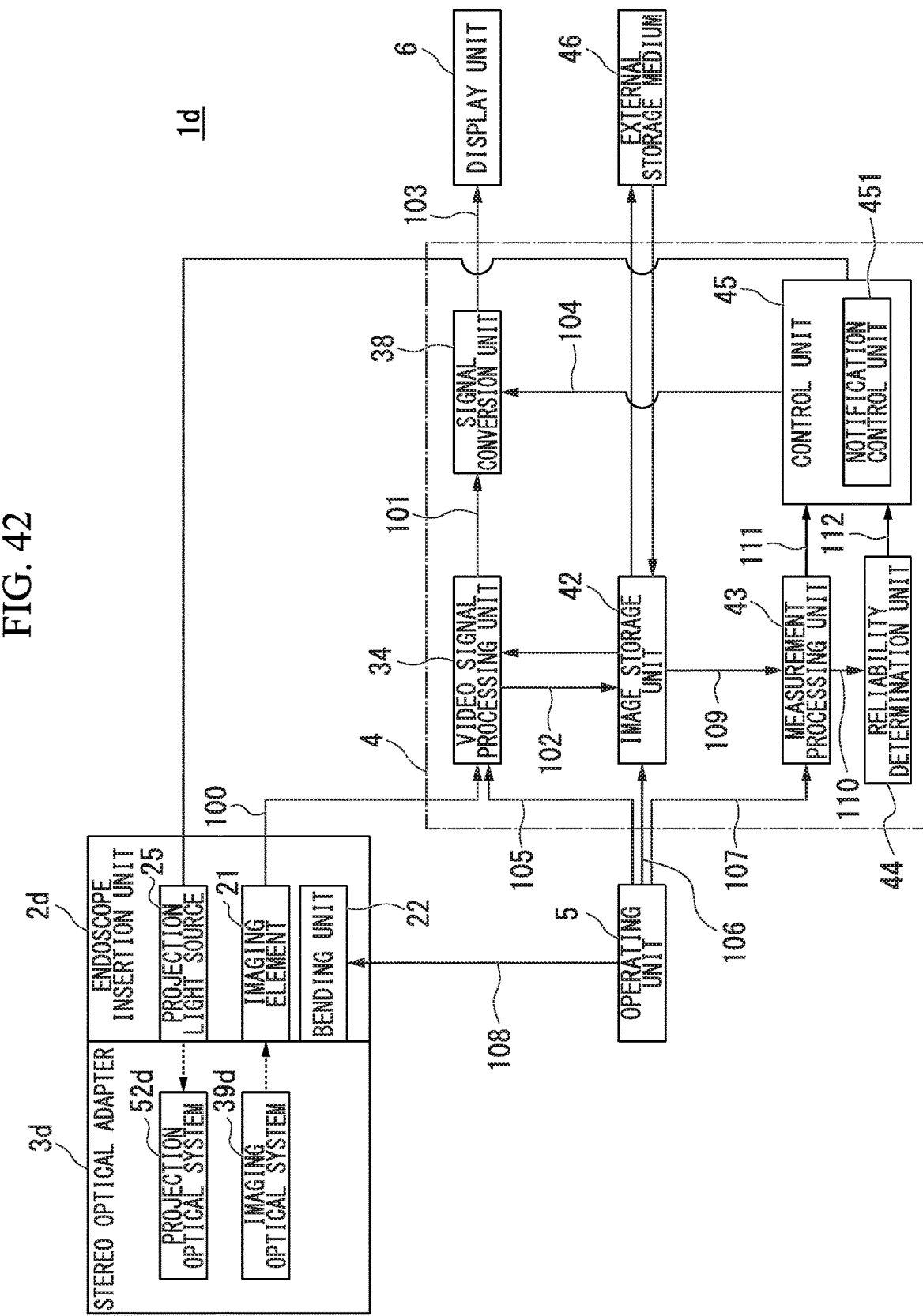
FIG. 42 is a block diagram showing a configuration of a measurement endoscope apparatus according to a fifth embodiment of the present invention.

In the fifth embodiment, the measurement endoscope apparatus 1 of the first embodiment is changed to a measurement endoscope apparatus 1d shown in FIG. 42. An external view of the measurement endoscope apparatus 1d is the same as an external view of the measurement endoscope apparatus 1 shown in FIG. 1.

FIG. 42 shows a configuration of the measurement endoscope apparatus 1d of the fifth embodiment. The difference between FIGS. 4 and 42 will be described.

The endoscope insertion unit 2 in FIG. 4 is changed to an endoscope insertion unit 2d and the stereo optical adapter 3 in FIG. 4 is changed to a stereo optical adapter 3d. The endoscope insertion unit 2d includes an imaging element 21, a bending unit 22, and a projection light source 25. The stereo optical adapter 3d includes an imaging optical system 39d and a projection optical system 52d. In the configuration shown in FIG. 42, the stereo optical adapter 3d is disposed near the distal end 20d (FIG. 43) of the endoscope insertion unit 2d. The imaging optical system 39d and the projection optical system 52d that constitute the stereo optical adapter 3d may be disposed inside the distal end 20d of the endoscope insertion unit 2d.

The projection light source 25 is disposed in the distal end 20d of the endoscope insertion unit 2d. For example, the projection light source 25 is a semiconductor laser. The projection light source 25 generates laser light. The projection light source 25 may be disposed in the controller 4 and the laser light generated by the projection light source 25 may be guided to the distal end 20d of the endoscope insertion unit 2d by an optical fiber.

The projection optical system 52d is disposed at the distal end 20d of the endoscope insertion unit 2d. The projection optical system 52d projects a random pattern on the subject. At the distal end 20d of the endoscope insertion unit 2d, the imaging optical system 39d is disposed at a position different from the position where the projection optical system 52d is disposed. The imaging optical system 39d images an optical image of the subject on which the random pattern is projected. The imaging element 21 generates an imaging signal 100 based on the optical image formed on the light receiving surface 24 via the imaging optical system 39d. That is, the imaging element 21 generates a first image corresponding to the optical image obtained via the imaging optical system 39d.

Aspects other than the above-described aspect of the process shown in FIG. 42 are the same as those of the process shown in FIG. 4.

Figure 43:
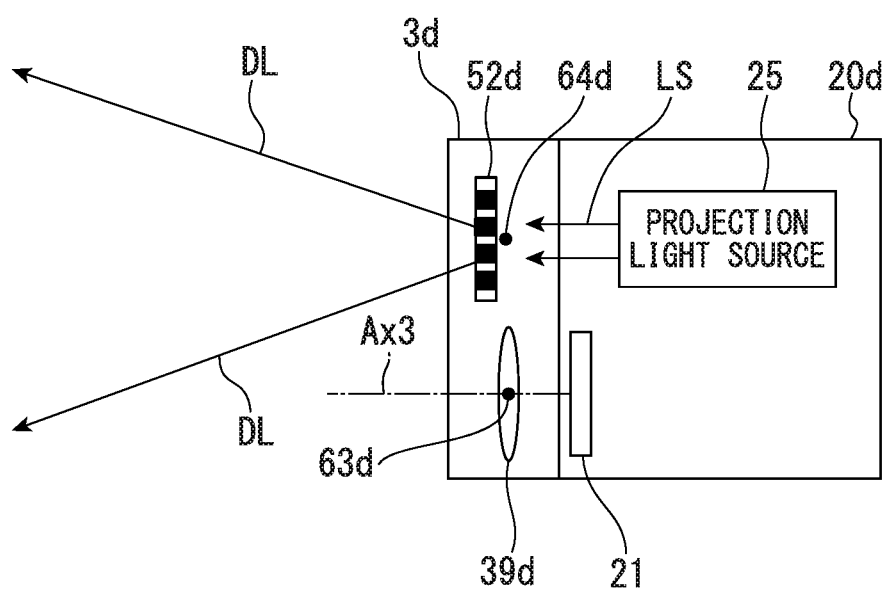
FIG. 43 is a block diagram showing a configuration of a stereo optical adapter and a distal end of an endoscope insertion unit of the measurement endoscope apparatus according to the fifth embodiment of the present invention.

FIG. 43 shows the configuration of the stereo optical adapter 3d and the distal end 20d of the endoscope insertion unit 2d. The laser light LS output from the projection light source 25 enters the projection optical system 52d. For example, the projection optical system 52d is a diffractive optical element (DOE). When the laser light enters the DOE, a random pattern is generated. The random pattern has a brightness distribution which is spatially random. The output intensity of the projection light source 25 is controlled by the control unit 45. The center 64d of the projection optical system 52d is a point at which main fluxes DL of diffracted light converge. The diffracted light output from the projection optical system 52d forms a random pattern. The projection optical system 52d generates a random pattern and projects the random pattern on the subject. The random pattern may be generated by a liquid crystal shutter module or a MEMS mirror module. The projection optical system 52d may include a projection lens.

The imaging optical system 39d includes an objective lens. The position of the optical center 63d of the imaging optical system 39d is different from the position of the center 64d of the projection optical system 52d. At least in a direction vertical to the optical axis AX3 of the imaging optical system 39d, the position of the optical center 63d of the imaging optical system 39d is different from the position of the center 64d of the projection optical system 52d.

As shown in FIG. 5, the measurement processing unit 43 includes a measurement point designation unit 431 (a measurement point setting unit), a correspondence point searching unit 432, and a 3-dimensional coordinate calculation unit 433. The measurement point designation unit 431 sets a measurement point in a first image corresponding to an optical image obtained via the imaging optical system 39d when the random pattern is projected on the subject. A second image is an image of the projected random pattern and is stored in advance in the image storage unit 42. The correspondence point searching unit 432 searches for a correspondence point of the second image corresponding to the measurement point by processing a video signal corresponding to the first image and a video signal corresponding to the second image of the random pattern. That is, the correspondence point searching unit 432 searches the second image of the random pattern for a correspondence point corresponding to the measurement point set by the measurement point designation unit 431. The 3-dimensional coordinate calculation unit 433 calculates the 3-dimensional coordinates of the measurement point by the principle of triangulation using the measurement point and the correspondence point searched for by the correspondence point searching unit 432. As disclosed in Japanese Patent No. 5001286, 3-dimensional measurement can be performed on the basis of the position of a local pattern in an image of the subject on which a random pattern is projected.

With the above-described configuration, the measurement processing unit 43 performs a measurement process by the principle of triangulation on the basis of the image generated by the imaging element 21 and the camera parameters of a first position and a second position different from the first position. The first position is the position of the optical center 63*d* of the imaging optical system 39*d*. The second position is the position of the center 64*d* of the projection optical system 52*d*. Moreover, the camera parameters may include a position parameter of the first position and a position parameter of the second position or may include a distance parameter of the distance between the first and second positions.

The reliability determination unit 44 determines the reliability of the correspondence point (that is, the reliability of the measurement process). The notification control unit 451 sends a notification to prompt the user to perform a bending operation of bending the distal end 20*d* of the endoscope insertion unit 2*d* so that the distal end 20*d* of the endoscope insertion unit 2*d* is moved in a direction from the projection optical system 52*d* toward the imaging optical system 39*d* when the reliability determination unit 44 determines that the reliability is low. In other words, the notification control unit 451 sends a notification to prompt the user to perform an operation of moving the distal end 20*d* of the endoscope insertion unit 2*d* in a direction from the projection optical system 52*d* toward the imaging optical system 39*d* when the reliability determination unit 44 determines that the reliability is low. In other words, the notification control unit 451 sends a notification to prompt the user to perform an operation of moving the distal end 20*d* of the endoscope insertion unit 2*d* in a direction from the position (the second position) of the center 64*d* of the projection optical system 52*d* toward the position (the first position) of the optical center 63*d* of the imaging optical system 39*d* when the reliability determination unit 44 determines that the reliability is low.

For example, the second image is an image of a random pattern imaged when the random pattern is projected on a plane having a single color. For example, the second image is obtained by the imaging element 21 before or after a product is shipped and the second image is stored in the image storage unit 42. The second image may be stored in advance in the external storage medium 46 and the second image may be read from the external storage medium 46 to the image storage unit 42 during measurement.

The position (the first position) of the optical center 63*d* of the imaging optical system 39*d* is different from the position (the second position) of the center 64*d* of the projection optical system 52*d*. Due to this, a region on which the random pattern is not projected may be formed on the surface of the subject that is visible in the first image corresponding to the optical image obtained via the imaging optical system 39*d*. This is a state in which occlusion occurs in the fifth embodiment. The moving direction of the distal end 20*d* of the endoscope insertion unit 2*d* for avoiding occlusion is the direction from the projection optical system 52*d* toward the imaging optical system 39*d*. The moving direction of the distal end 20*d* of the endoscope insertion unit 2*d* may not be perfectly identical to this direction. The moving direction of the distal end 20*d* of the endoscope insertion unit 2*d* has only to be a direction in which the projection optical system 52*d* approaches the position of the imaging optical system 39*d* before the distal end 20*d* of the endoscope insertion unit 2*d* is moved.

Figure 44:
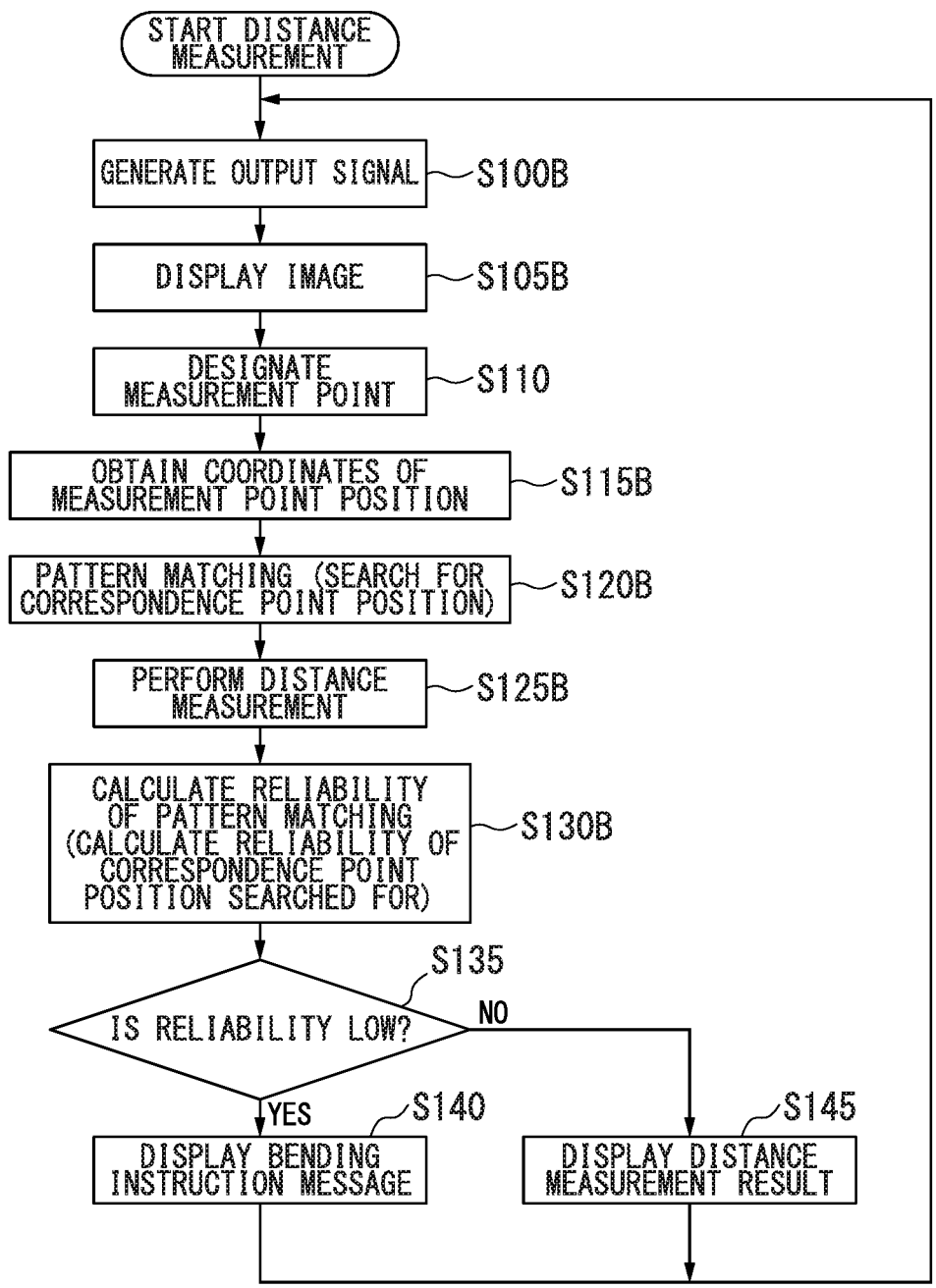
FIG. 44 is a flowchart showing the procedure of an operation of the measurement endoscope apparatus according to the fifth embodiment of the present invention.

FIG. 44 shows the procedure of an operation of the measurement endoscope apparatus 1*d* during distance measurement. The difference between FIGS. 7 and 44 will be described.

After distance measurement starts, the imaging element 21 generates an image in a state in which a random pattern is not projected on the subject. Furthermore, the imaging element 21 generates a first image in a state in which a random pattern is generated by the projection optical system 52*d* and the random pattern is projected on the subject (step S100B). Step S100B corresponds to step S100 in FIG. 7.

After step S100B is performed, the display unit 6 displays an image when illumination light was radiated on the subject (step S105B). Step S105B corresponds to step S105 in FIG. 7.

After step S110 is performed, the measurement point designation unit 431 sets a measurement point to the first image of the subject on which the random pattern is projected on the basis of the measurement point designated to an image when the random pattern was not projected on the subject. That is, the measurement point designation unit 431 obtains a 2-dimensional coordinates of the position of the measurement point (step S115B). Step S115B corresponds to step S115 in FIG. 7.

After step S115B is performed, the correspondence point searching unit 432 performs pattern matching between template image data and the image data 109 corresponding to the second image and searches for a correspondence point of the second image corresponding to the measurement point (step S120B). The template image data is a predetermined size of data including the position of the measurement point in the image data 109 corresponding to the first image of the subject on which the random pattern is projected. The second image is the image of the random pattern. Step S120B corresponds to step S120 in FIG. 7.

After step S120B is performed, the 3-dimensional coordinate calculation unit 433 performs a distance measurement process (step S125B). In step S125B, the 3-dimensional coordinate calculation unit 433 calculates the 3-dimensional coordinates of the measurement point by the principle of triangulation using the measurement point and the correspondence point searched for by the correspondence point searching unit 432. Step S125B corresponds to step S125 in FIG. 7.

After step S125B is performed, the reliability determination unit 44 calculates the reliability of the pattern matching (step S130B). In step S130B, the first image of the subject on which the random pattern is projected and the second image of the random pattern are used. Step S130B corresponds to step S130 in FIG. 7.

Aspects other than the above-described aspect of the process shown in FIG. 44 are the same as those of the process shown in FIG. 7.

In step S105B, the display unit 6 displays an image when the random pattern was not projected on the subject. When the user designates the measurement point to an image obtained when the random pattern was not projected on the subject, the user can designate the measurement point on an image in which the subject is highly visible. In step S105B, the display unit 6 may display the first image obtained when the random pattern was projected on the subject.

According to the fifth embodiment, the measurement endoscope apparatus 1d includes the endoscope insertion unit 2d, the projection optical system 52d, the imaging optical system 39d, the imaging element 21, the measurement processing unit 43, the reliability determination unit 44, and the notification control unit 451.

In the fifth embodiment, the notification control unit 451 sends a notification to prompt the user to perform a bending operation of bending the distal end 20d of the endoscope insertion unit 2d so that the distal end 20d of the endoscope insertion unit 2d is moved in a direction from the projection optical system 52d toward the imaging optical system 2d when the reliability determination unit 44 determines that the reliability is low. In this way, it is possible to suppress a decrease in measurement accuracy due to the occurrence of occlusion.

The measurement endoscope apparatus 1d may perform control similar to the control performed by the measurement endoscope apparatus 1a of the second embodiment. That is, when occlusion occurs, the measurement endoscope apparatus 1d may automatically bend the distal end 20d of the endoscope insertion unit 2d in a direction in which the occlusion is avoided. In this case, the control unit 45c has the bending control unit 452 shown in FIGS. 18 and 19. The bending control unit 452 controls the bending unit 22 so that the distal end 20d of the endoscope insertion unit 2d is moved in a direction from the projection optical system 52d toward the imaging optical system 39d when the reliability determination unit 44 determines that the reliability is low. In other words, the bending control unit 452 controls the bending unit 22 so that the distal end 20d of the endoscope insertion unit 2d is moved in a direction from the position (the second position) of the center 64d of the projection optical system 52d toward the position (the first position) of the optical center 63d of the imaging optical system 39d when the reliability determination unit 44 determines that the reliability is low.

The measurement endoscope apparatus 1d may perform control similar to the control performed by the measurement endoscope apparatus 1b of the third embodiment. That is, a process of bending the distal end 20d of the endoscope insertion unit 2d by a very small amount and a process of determining whether or not occlusion has occurred are performed repeatedly. In this case, the bending control unit 452 controls the bending unit 22 so that the distal end 20d of the endoscope insertion unit 2d is bent by a predetermined bending amount. The reliability determination unit 44 determines the reliability before and after the control of the bending unit 22 according to the predetermined bending amount is performed.

Sixth Embodiment

In the first to third embodiments of the present invention, the stereo optical adapter 3 and the distal end 20 of the endoscope insertion unit 2 shown in FIG. 3 are used. In the first to third embodiments, the first and second optical images are formed simultaneously on the light receiving surface 24 by the first and second optical systems 31 and 32. The imaging element 21 generates the imaging signal 100 based on the first and second optical images. The method for manufacturing the measurement endoscope apparatus 1, 1a, and 1b perform 3-dimensional measurement based on the optical images obtained via two imaging optical systems.

However, a 3-dimensional shape estimation method called a Structure from Motion (SfM) may be applied to a measurement endoscope apparatus. In SfM, the relative position and attitude between a subject and a camera and the 3-dimensional shape of the subject are estimated simultaneously using a plurality of images imaged at different viewpoints. The sixth embodiment of the present invention relates to a measurement endoscope apparatus to which SfM is applied.

Figure 45:
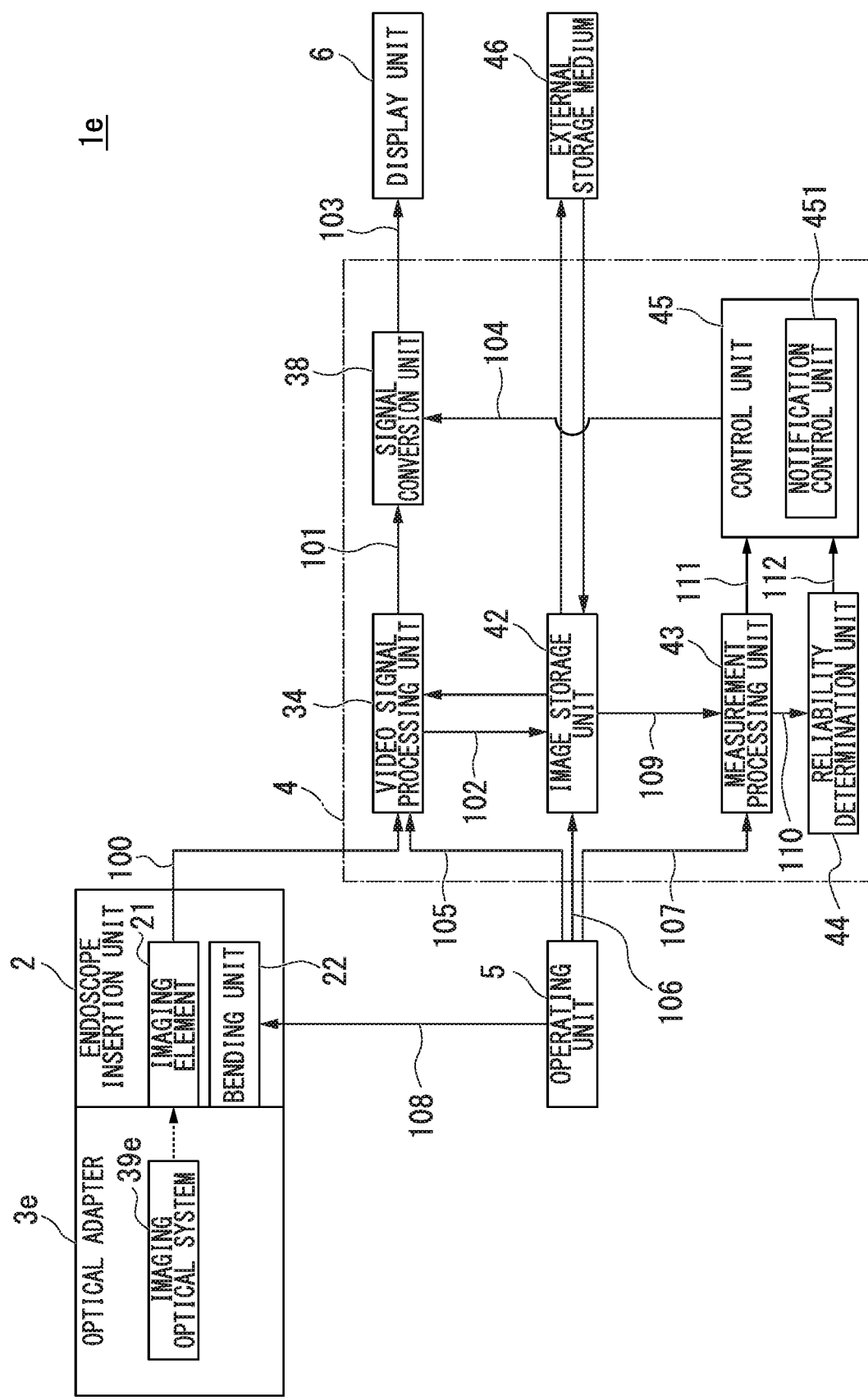
FIG. 45 is a block diagram showing a configuration of a measurement endoscope apparatus according to a sixth embodiment of the present invention.

In the sixth embodiment of the present invention, the measurement endoscope apparatus 1 of the first embodiment is changed to a measurement endoscope apparatus 1e shown in FIG. 45. An external view of the measurement endoscope apparatus 1e is the same as an external view of the measurement endoscope apparatus 1 shown in FIG. 1.

FIG. 45 shows a configuration of the measurement endoscope apparatus 1e of the sixth embodiment. The difference between FIGS. 4 and 45 will be described.

The stereo optical adapter 3 in FIG. 4 is changed to an optical adapter 3e. The optical adapter 3e has an imaging optical system 39e. In the configuration shown in FIG. 45, the optical adapter 3e is disposed near the distal end 20 (FIG. 46) of the endoscope insertion unit 2. The imaging optical system 39e that constitutes the optical adapter 3e may be disposed inside the distal end 20 of the endoscope insertion unit 2.

The imaging optical system 39e is disposed at the distal end 20 of the endoscope insertion unit 2. The imaging optical system 39e images an optical image of the subject at a first position and a second position different from the first position. The imaging element 21 generates an imaging signal 100 based on a first optical image formed on the light receiving surface 24 via the imaging optical system 39e at the first position. Moreover, the imaging element 21 generates an imaging signal 100 based on a second optical image formed on the light receiving surface 24 via the imaging optical system 39e at the second position. That is, the imaging element 21 generates the first image corresponding to the first optical image obtained via the imaging optical system 39e at the first position and the second image corresponding to the second optical image obtained via the imaging optical system 39e at the second position.

Aspects other than the above-described aspect of the configuration shown in FIG. 45 are the same as those of the configuration shown in FIG. 4.

Figure 46:
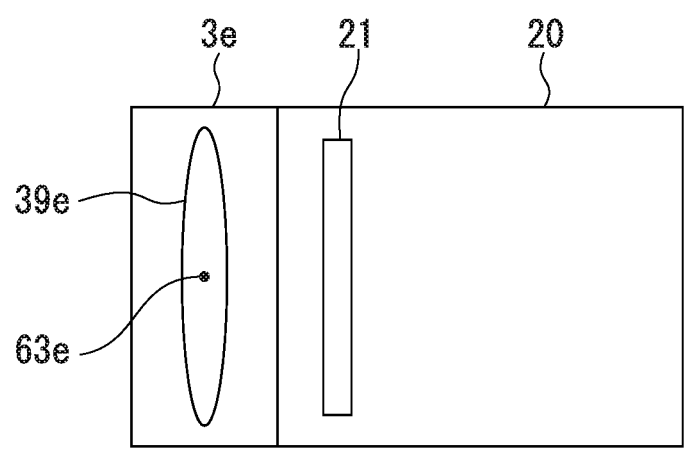
FIG. 46 is a block diagram showing a configuration of an optical adapter and a distal end of an endoscope insertion unit of the measurement endoscope apparatus according to the sixth embodiment of the present invention.

FIG. 46 shows a configuration of the optical adapter 3e and the distal end 20 of the endoscope insertion unit 2. The imaging optical system 39e includes an objective lens. The first image is generated when the position of the optical center 63e of the imaging optical system 39e is at the first position, and the second image is generated when the position of the optical center 63e of the imaging optical system 39e is at the second position.

As shown in FIG. 5, the measurement processing unit 43 includes the measurement point designation unit 431 (a measurement point setting unit), the correspondence point searching unit 432, and the 3-dimensional coordinate calculation unit 433. The measurement point designation unit 431 sets a measurement point to the first image corresponding to the first optical image obtained via the imaging optical system 39e at the first position. The correspondence point searching unit 432 searches for a correspondence point of the second image corresponding to the measurement point by processing a video signal corresponding to the first image and a video signal corresponding to the second image. That is, the correspondence point searching unit 432 searches the second image for a correspondence point corresponding to the measurement point set by the measurement point designation unit 431. The second image corresponds to the second optical image obtained via the imaging optical system 39e at the second position. The third 3-dimensional coordinate calculation unit 433 calculates the 3-dimensional coordinates of the measurement point by the principle of triangulation using the measurement point and the correspondence point searched for by the correspondence point searching unit 432.

With the above-described configuration, the measurement processing unit 43 performs a measurement process by the principle of triangulation on the basis of the image generated by the imaging element 21 and the camera parameters of the first position and the second position different from the first position. The first and second positions are different positions of the distal end 20 (the imaging optical system 39e) of the endoscope insertion unit 2. On the other hand, the measurement processing unit 43 calculates the relative position and attitude between the subject and the camera and the 3-dimensional shape of the subject according to SfM. Here, the estimated position of the camera is the position of the optical center 63e and the estimated attitude of the camera is a direction of the optical axis. The estimated position and attitude of the camera are a portion of the camera parameters. That is, in the sixth embodiment, the camera parameters include a camera position parameter of the first position, a camera attitude parameter of the first position, a camera position parameter of the second position, and a camera attitude parameter of the second position. The measurement processing unit 43 can calculate a 3-dimensional shape but cannot calculate actual 3-dimensional dimensions (scales).

The reliability determination unit 44 determines the reliability of the correspondence point (that is, the reliability of the measurement process). The notification control unit 451 sends a notification to prompt the user to perform a bending operation of bending the distal end 20 of the endoscope insertion unit 2 so that the distal end 20 of the endoscope insertion unit 2 is moved in a direction from the second position toward the first position when the reliability determination unit 44 determines that the reliability is low. In other words, the notification control unit 451 sends a notification to prompt the user to perform an operation of moving the distal end 20 of the endoscope insertion unit 2 in a direction from the second position toward the first position when the reliability determination unit 44 determines that the reliability is low.

The position (the first position) of the optical center 63e of the imaging optical system 39e when the first image is generated is different from the position (the second position) of the optical center 63e of the imaging optical system 39e when the second image is generated. Due to this, a region which is visible in the first image but is not visible in the second image may be generated. This is a state in which occlusion occurs in the sixth embodiment. The moving direction of the distal end 20 of the endoscope insertion unit 2 for avoiding occlusion is the direction from the second position toward the first position. The moving direction of the distal end 20 of the endoscope insertion unit 2 may not be perfectly identical to this direction. The moving direction of the distal end 20 of the endoscope insertion unit 2 has only to be a direction in which the imaging optical system 39e approaches the first position.

After the distal end 20 of the endoscope insertion unit 2 is moved, the position of the optical center 63e of the imaging optical system 39e is a third position different from the first and second positions. The imaging optical system 39e images an optical image of the subject at the third position. The imaging element 21 generates a third image corresponding to a third optical image obtained via the imaging optical system 39e at the third position. The measurement processing unit 43 performs a measurement process using the first and third images.

The order in which the first and second images are generated is arbitrary. For example, the first image at the first position is generated, and then, the second image at the second position is generated. Alternatively, the second image at the second position is generated, and then, the first image at the first position is generated. In any case, the measurement point is set to the first image.

Figure 47:
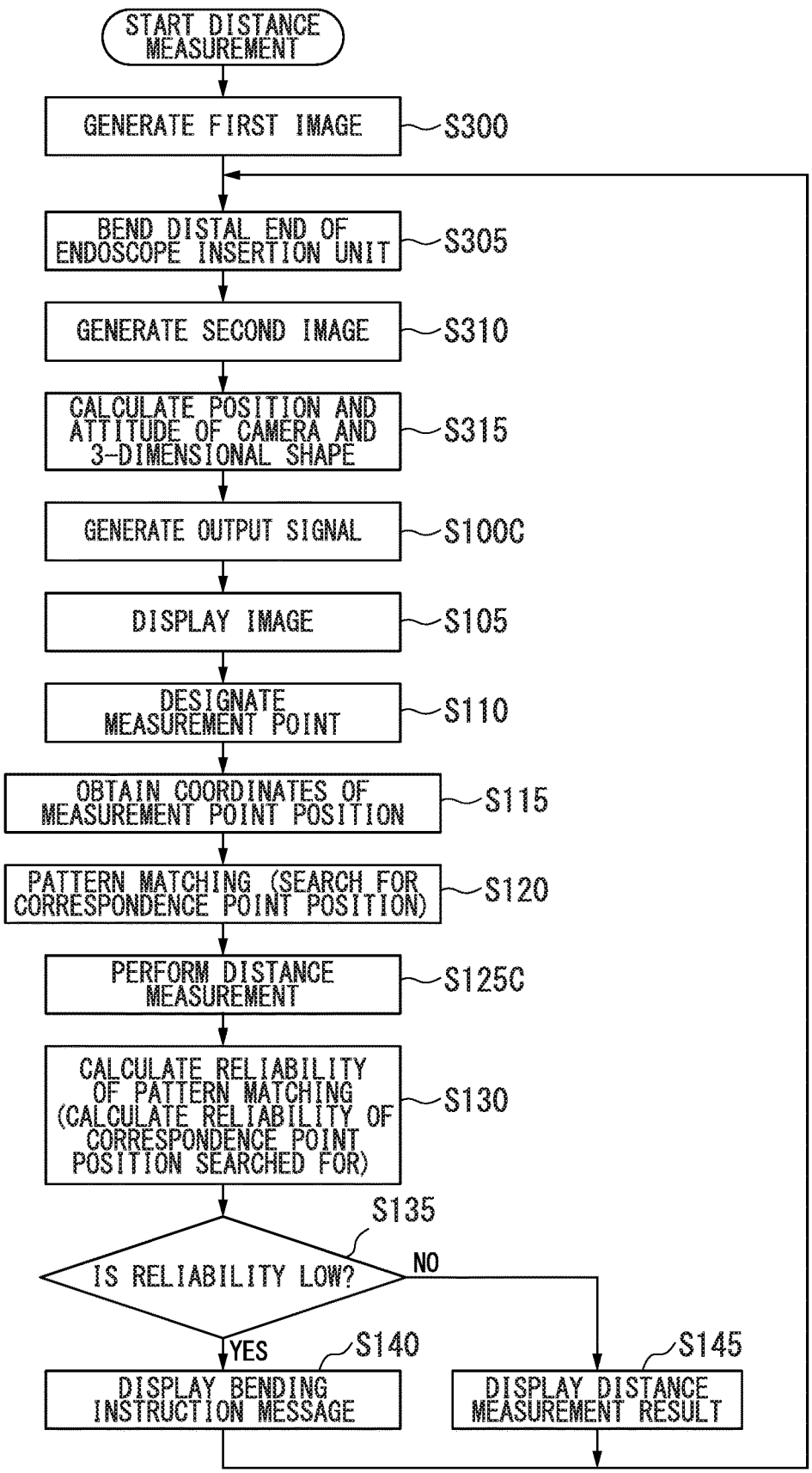
FIG. 47 is a flowchart showing the procedure of an operation of the measurement endoscope apparatus according to the sixth embodiment of the present invention.

FIG. 47 shows the procedure of an operation of the measurement endoscope apparatus 1e during distance measurement. The difference between FIGS. 7 and 47 will be described.

After distance measurement starts, the imaging optical system 39e images an optical image of the subject in a state in which the position of the optical center 63e of the imaging optical system 39e is at the first position. The imaging element 21 generates an imaging signal 100 based on the first optical image formed on the light receiving surface 24 via the imaging optical system 39e. That is, the imaging element 21 generates the first image corresponding to the first optical image obtained via the imaging optical system 39e. The video signal processing unit 34 generates an output video signal 102 from the imaging signal 100 (step S300).

After step S300 is performed, the user bends the distal end 20 of the endoscope insertion unit 2 by operating the operating unit 2 (step S305). In step S305, the control unit 45 controls the bending unit 22 on the basis of the user's operation on the operating unit 5. The bending unit 22 bends the distal end 20 of the endoscope insertion unit 2. In step S305, the control unit 45 may control the bending unit 22 so that the distal end 20 of the endoscope insertion unit 2 is bent by a predetermined amount. When the distal end 20 of the endoscope insertion unit 2 is bent, the position of the optical center 63e of the imaging optical system 39e moves from the first position to the second position.

After step S305 is performed, the imaging optical system 39e images the optical image of the subject in a state in which the position of the optical center 63e of the imaging optical system 39e is at the second position. The imaging element 21 generates the imaging signal 100 based on the second optical image formed on the light receiving surface 24 via the imaging optical system 39e. That is, the imaging element 21 generates the second image corresponding to the second optical image obtained via the imaging optical system 39e. The video signal processing unit 34 generates an output video signal 102 from the imaging signal 100 (step S310).

After step S310 is performed, the measurement processing unit 43 calculates the relative position and attitude between the subject and the camera and the 3-dimensional shape of the subject (step S315). In step S315, the 3-dimensional coordinates of a feature point in a virtual space is calculated as the 3-dimensional shape of the subject.

After step S315 is performed, the output video signal 102 corresponding to the first image is read from the image storage unit 42. The video signal processing unit 34 outputs the output video signal 102 read from the image storage unit 42 to the signal conversion unit 38 as the output video signal 101. The signal conversion unit 38 outputs the display video signal 103 based on the output video signal 101 to the display unit 6 (step S100C). Step S100C corresponds to step S100 in FIG. 7.

After step S120 is performed, the 3-dimensional coordinate calculation unit 433 performs a distance measurement process (step S125C). In step S125C, the 3-dimensional coordinate calculation unit 433 calculates the 3-dimensional coordinates of the measurement point by the principle of triangulation using the measurement point and the correspondence point searched for by the correspondence point searching unit 432. In this case, the 3-dimensional coordinate calculation unit 433 uses the information on the relative position and attitude between the subject and the camera calculated in step S315. That is, the parameter D corresponding to the distance between the first and second positions is calculated from the relative position and attitude between the subject and the camera calculated in step S315. The 3-dimensional coordinates calculated in step S125C are the coordinates in a virtual space. The 3-dimensional coordinate calculation unit 433 calculates the object distance in a virtual space by calculating the 3-dimensional coordinates of the measurement point. The 3-dimensional coordinate calculation unit 433 outputs the measurement result information 111 including the calculated object distance to the control unit 45. Step S125C corresponds to step S125 in FIG. 7.

In step S120, pattern matching between the template image data corresponding to the first image generated in step S300 and the image data 109 corresponding to the second image generated in step S310 is performed. After step S140 or S145 is performed, the process of step S305 is performed. In the second execution of step S310, a new second image (the third image) is generated.

Aspects other than the above-described aspect of the process shown in FIG. 47 are the same as those of the process shown in FIG. 7.

In the sixth embodiment, three or more images may be used. A process (a bundle adjustment) of adjusting all of data of the relative position and attitude between the subject and the camera and the 3-dimensional shape of the subject may be performed.

According to the sixth embodiment, the measurement endoscope apparatus 1e includes the endoscope insertion unit 2, the imaging optical system 39e, the imaging element 21, the measurement processing unit 43, the reliability determination unit 44, and the notification control unit 451.

In the sixth embodiment, the notification control unit 451 sends a notification to prompt the user to perform a bending operation of bending the distal end 20 of the endoscope insertion unit 2 so that the distal end 20 of the endoscope insertion unit 2 is moved in a direction from the second position toward the first position when the reliability determination unit 44 determines that the reliability is low. In this way, it is possible to suppress a decrease in measurement accuracy due to the occurrence of occlusion.

The measurement endoscope apparatus 1e may perform control similar to the control performed by the measurement endoscope apparatus 1a of the second embodiment. That is, when occlusion occurs, the measurement endoscope apparatus 1e may automatically bend the distal end 20 of the endoscope insertion unit 2 in a direction in which the occlusion is avoided. In this case, the control unit 45 has the bending control unit 452 shown in FIGS. 18 and 19. The bending control unit 452 controls the bending unit 22 so that the distal end 20 of the endoscope insertion unit 2 is moved in a direction from the second position toward the first position when the reliability determination unit 44 determines that the reliability is low.

The measurement endoscope apparatus 1e may perform control similar to the control performed by the measurement endoscope apparatus 1b of the third embodiment. That is, a process of bending the distal end 20 of the endoscope insertion unit 2 by a very small amount and a process of determining whether or not occlusion has occurred are performed repeatedly. In this case, the bending control unit 452 controls the bending unit 22 so that the distal end 20 of the endoscope insertion unit 2 is bent by a predetermined bending amount. The reliability determination unit 44 determines the reliability before and after the control of the bending unit 22 based on the predetermined bending amount is performed.

Seventh Embodiment

A seventh embodiment of the present invention relates to a measurement endoscope apparatus to which SfM is applied.

Figure 48:
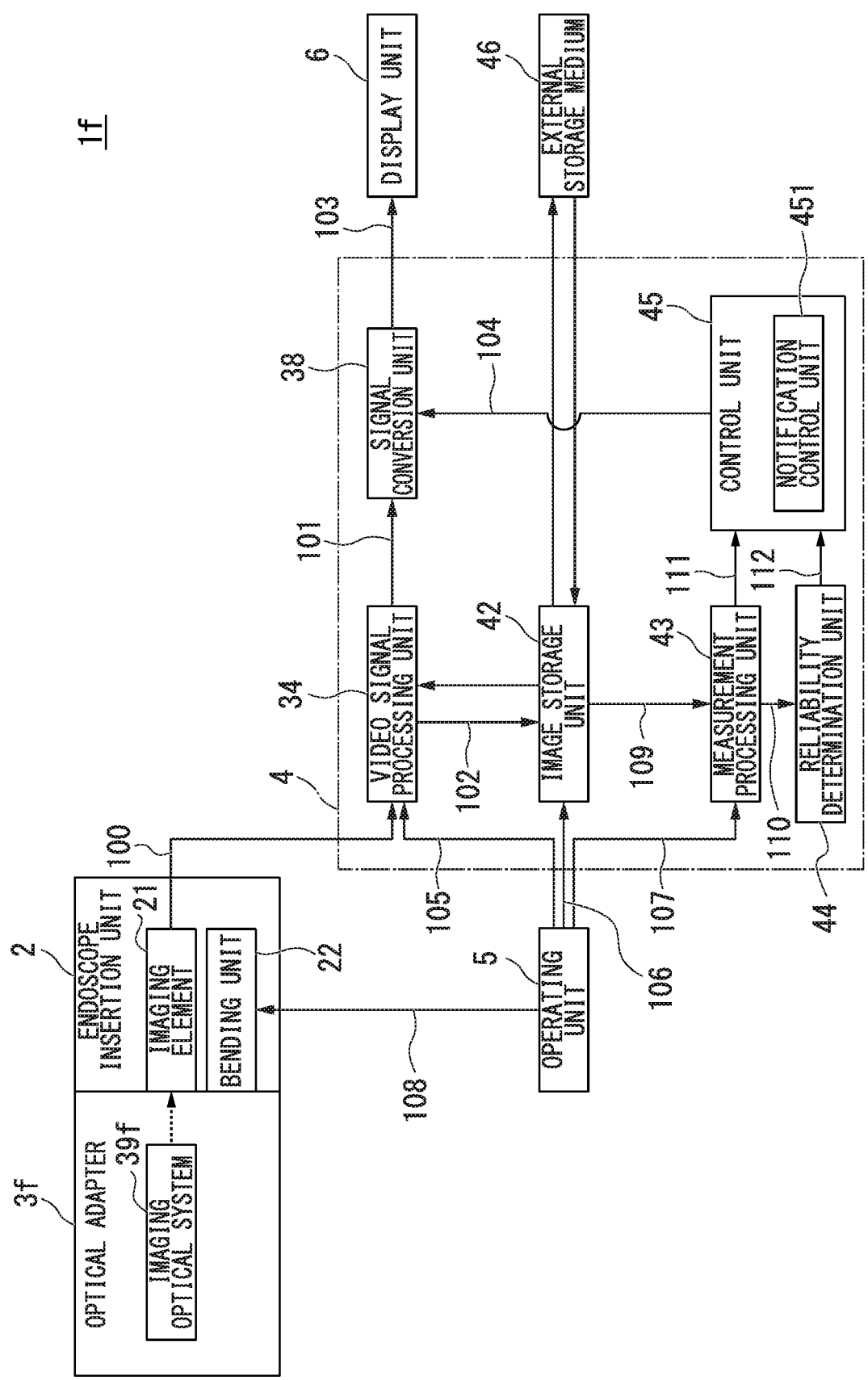
FIG. 48 is a block diagram showing a configuration of a measurement endoscope apparatus according to a seventh embodiment of the present invention.

In the seventh embodiment of the present invention, the measurement endoscope apparatus 1e of the sixth embodiment is changed to a measurement endoscope apparatus 1f shown in FIG. 48. An external view of the measurement endoscope apparatus 1f is the same as an external view of the measurement endoscope apparatus 1 shown in FIG. 1.

FIG. 48 shows a configuration of the measurement endoscope apparatus 1f of the seventh embodiment. The difference between FIGS. 45 and 48 will be described.

The optical adapter 3e in FIG. 45 is changed to an optical adapter 3f. The optical adapter 3f includes an imaging optical system 39f. In the configuration shown in FIG. 48, the optical adapter 3f is disposed near the distal end 20 (FIG. 49) of the endoscope insertion unit 2. The imaging optical system 39f that constitutes the optical adapter 3f may be disposed inside the distal end 20 of the endoscope insertion unit 2.

The imaging optical system 39f is disposed at the distal end 20 of the endoscope insertion unit 2. The imaging optical system 39f images an optical image of the subject at a first position and a second position different from the first position. The imaging element 21 generates an imaging signal 100 based on a first optical image formed on the light receiving surface 24 via the imaging optical system 39f at the first position. Moreover, the imaging element 21 generates an imaging signal 100 based on a second optical image formed on the light receiving surface 24 via the imaging optical system 39f at the second position. That is, the imaging element 21 generates the first image corresponding to the first optical image obtained via the imaging optical system 39f at the first position and the second image corresponding to the second optical image obtained via the imaging optical system 39f at the second position.

Aspects other than the above-described aspect of the configuration shown in FIG. 48 are the same as those of the configuration shown in FIG. 45.

Figure 49:
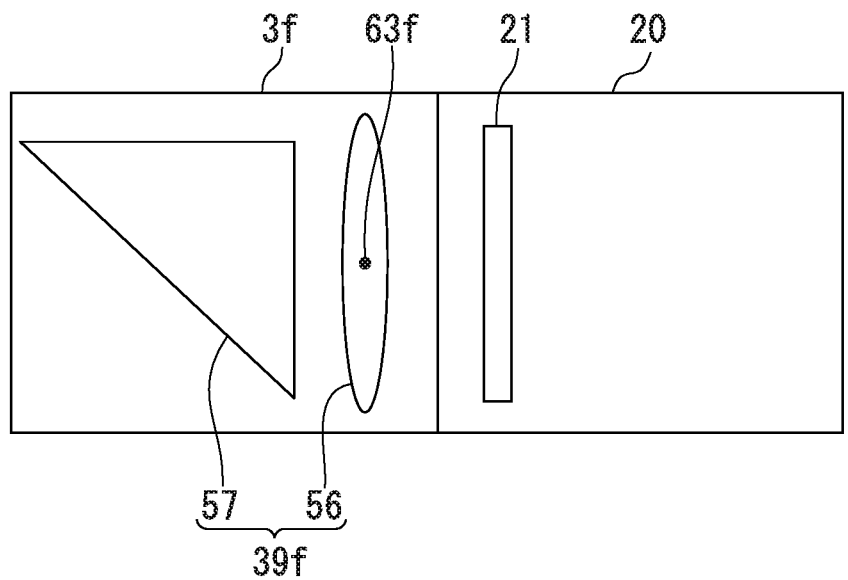
FIG. 49 is a block diagram showing a configuration of an optical adapter and a distal end of an endoscope insertion unit of the measurement endoscope apparatus according to the seventh embodiment of the present invention.

FIG. 49 shows a configuration of the optical adapter 3f and the distal end 20 of the endoscope insertion unit 2. The imaging optical system 39f includes a lens 56 and a prism 57. The lens 56 is disposed on the front side of the imaging element 21 and the prism 57 is disposed on the front side of the lens 56. A window not shown is provided in a side surface of the optical adapter 3f and the prism 57 is disposed in the window. The prism 57 allows light incident on the side surface of the optical adapter 3f to enter the lens 56. The lens 56 allows light guided by the prism 57 to enter the imaging element 21 and forms the optical image of the subject. The optical adapter 3f is a lateral-view optical adapter for observing a direction perpendicular to the insertion direction of the endoscope insertion unit 2. The first image is generated when the position of the optical center 63f of the lens 56 is at the first position, and the second image is generated when the position of the optical center 63f of the lens 56 is at the second position.

With the above-described configuration, the measurement processing unit 43 performs a measurement process by the principle of triangulation on the basis of an image generated by the imaging element 21 and the camera parameters of the first position and the second position different from the first position. The first and second positions are different positions of the distal end 20 (the imaging optical system 39f) of the endoscope insertion unit 2. The measurement processing unit 43 calculates the relative position and attitude between the subject and the camera and the 3-dimensional shape of the subject. Here, the estimated position of the camera is the position of the optical center 63f and the estimated attitude of the camera is a direction of the optical axis. The estimated position and attitude of the camera are a portion of the camera parameters. That is, in the seventh embodiment, the camera parameters include a camera position parameter of the first position, a camera attitude parameter of the first position, a camera position parameter of the second position, and a camera attitude parameter of the second position. The measurement processing unit 43 can calculate a 3-dimensional shape but cannot calculate actual 3-dimensional dimensions (scales).

The reliability determination unit 44 determines the reliability of the correspondence point (that is, the reliability of the measurement process). The notification control unit 451 sends a notification to prompt the user to perform a bending operation of bending the distal end 20 of the endoscope insertion unit 2 so that the distal end 20 of the endoscope insertion unit 2 is moved in a direction from the second position toward the first position when the reliability determination unit 44 determines that the reliability is low. In other words, the notification control unit 451 sends a notification to prompt the user to perform an operation of moving the distal end 20 of the endoscope insertion unit 2 in a direction from the second position toward the first position when the reliability determination unit 44 determines that the reliability is low.

Figure 50:
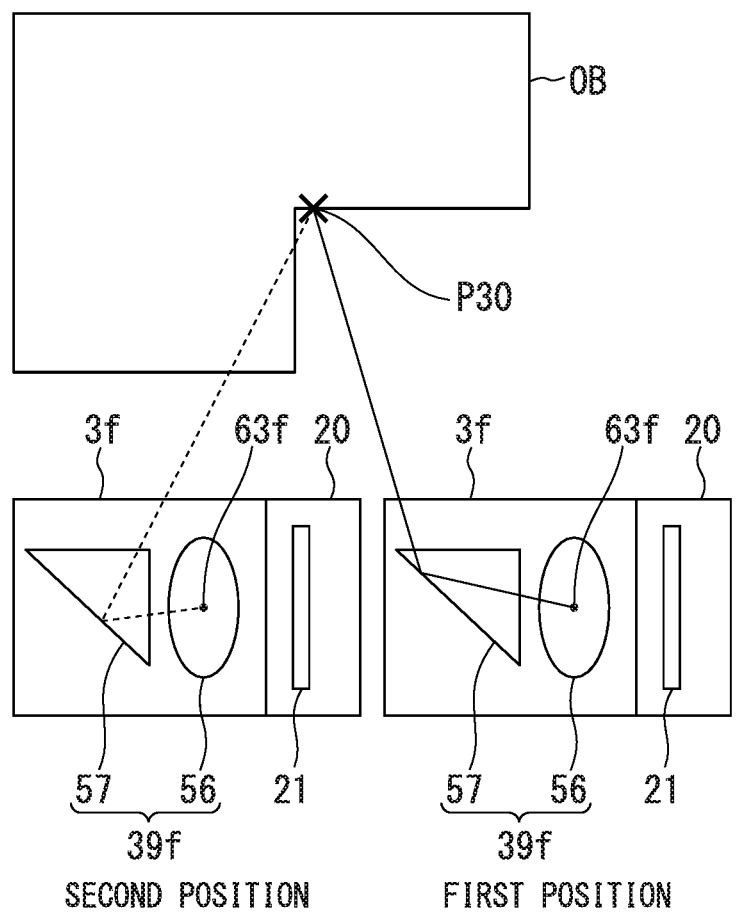
FIG. 50 is a reference diagram showing the positions of a subject and the distal end of the endoscope insertion unit of the measurement endoscope apparatus according to the seventh embodiment of the present invention.

FIG. 50 schematically shows the positions of the subject OB and the distal end 20 of the endoscope insertion unit 2. FIG. 50 shows a state in which the subject OB and the distal end 20 of the endoscope insertion unit 2 are projected on the xz-plane shown in FIG. 6. A point on the space in FIG. 50 is shown as a point projected on the xz-plane. The position (the first position) of the optical center 63f of the lens 56 when the first image is generated is different from the position (the second position) of the optical center 63f of the lens 56 when the second image is generated. For example, the first and second positions are different positions in the insertion direction of the endoscope insertion unit 2. When the position of the optical center 63f of the lens 56 is at the first position, light from a point P30 on the subject OB enters the prism 57 without being blocked by the subject OB. When the position of the optical center 63f of the lens 56 is at the second position, light from the point P30 on the subject OB is blocked by the subject OB. Due to this, light from the point P30 does not enter the prism 57.

Figure 51:
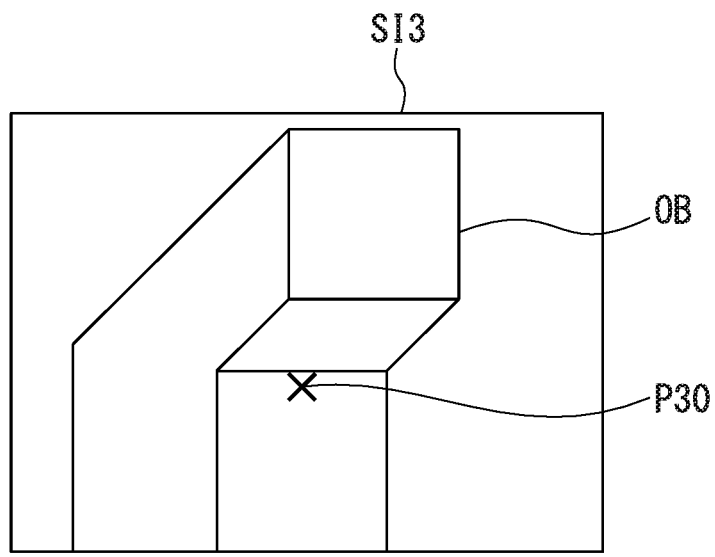
FIG. 51 is a reference diagram showing a subject image seen from an optical center of a lens of the measurement endoscope apparatus according to the seventh embodiment of the present invention.
Figure 52:
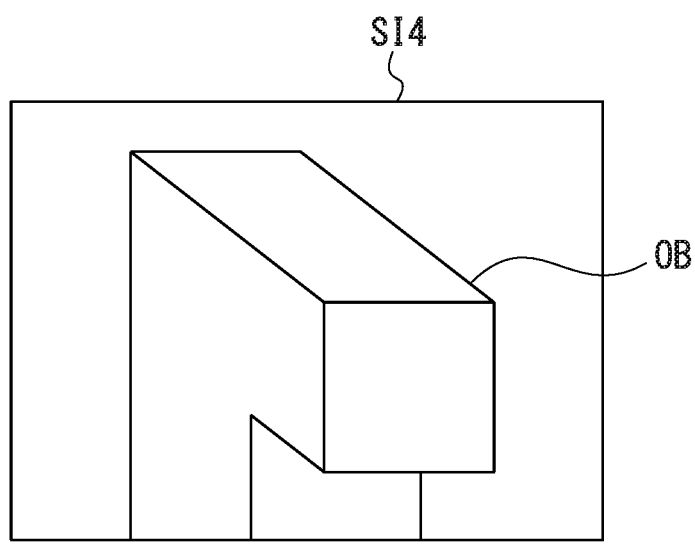
FIG. 52 is a reference diagram showing a subject image seen from the optical center of the lens of the measurement endoscope apparatus according to the seventh embodiment of the present invention.

FIG. 51 shows a subject image SI3 seen from the optical center 63f of the lens 56 when the position of the imaging optical system 39f (that is, the position of the optical center 63f of the lens 56) is at the first position. FIG. 52 shows a subject image SI4 seen from the optical center 63f of the lens 56 when the position of the imaging optical system 39f (that is, the position of the optical center 63f of the lens 56) is at the second position. As shown in FIG. 51, the point P30 is visible in the subject image 813. As shown in FIG. 52, the point P30 is not visible in the subject image 814. This is a state in which occlusion occurs in the seventh embodiment. The moving direction of the distal end 20 of the endoscope insertion unit 2 for avoiding occlusion is the direction from the second position toward the first position. For example, the moving direction of the distal end 20 of the endoscope insertion unit 2 for avoiding the occlusion is the direction opposite to the insertion direction of the endoscope insertion unit 2. The moving direction of the distal end 20 of the endoscope insertion unit 2 may not be perfectly identical to this direction. The moving direction of the distal end 20 of the endoscope insertion unit 2 has only to be a direction in which the imaging optical system 39f approaches the first position.

After the distal end 20 of the endoscope insertion unit 2 is moved, the position of the optical center 63f of the imaging optical system 39f is a third position different from the first and second positions. The imaging optical system 39f images an optical image of the subject at the third position. The imaging element 21 generates a third image corresponding to a third optical image obtained via the imaging optical system 39f at the third position. The measurement processing unit 43 performs a measurement process using the first and third images.

The order in which the first and second images are generated is arbitrary. For example, the first image at the first position is generated, and then, the second image at the second position is generated. Alternatively, the second image at the second position is generated, and then, the first image at the first position is generated. In any case, the measurement point is set to the first image.

The procedure of an operation of the measurement endoscope apparatus if during distance measurement is similar to the procedure shown in FIG. 47. Due to this, the description of the procedure of the operation of the measurement endoscope apparatus if during distance measurement will be omitted.

Figure 53:
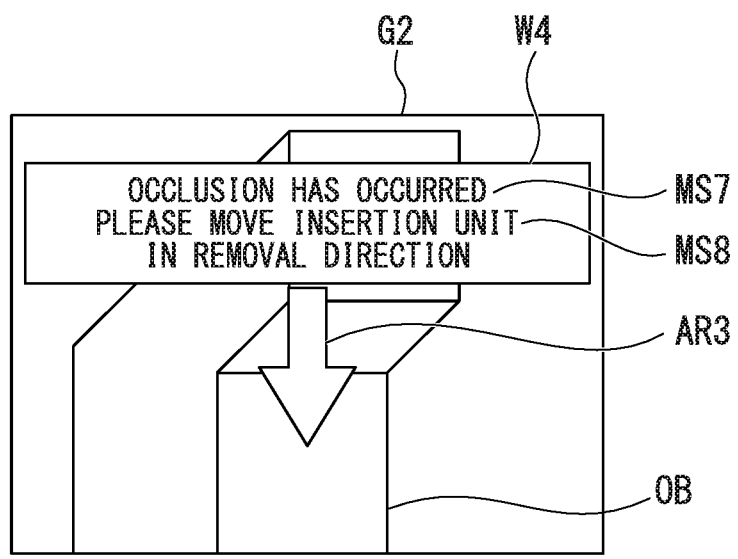
FIG. 53 is a reference diagram showing an image displayed by a display unit of the measurement endoscope apparatus according to the seventh embodiment of the present invention.

FIG. 53 shows an example of an image displayed by the display unit 6 in step S140. The display unit 6 displays an image G2. The image G2 is based on the first optical image formed via the imaging optical system 39f. The subject OB appears in the image G2. The display unit 6 displays a message window W4. The message window W4 includes a message MS7 indicating the occurrence of occlusion and a message MS8 for prompting the user to move the distal end 20 of the endoscope insertion unit 2. Moreover, the message window W4 includes an arrow AR3 indicating a moving direction. The arrow AR3 indicates a downward direction. The direction indicated by the arrow AR3 schematically shows the direction opposite to the insertion direction of the endoscope insertion unit 2. Since the message MS8 and the arrow AR3 are displayed, the user can understand that the endoscope insertion unit 2 should be pulled in the direction opposite to the insertion direction of the endoscope insertion unit 2 in order to avoid the occlusion. The user can move the endoscope insertion unit 2 by operating the operating unit 5 according to the displayed message. As a result, the user can designate the measurement point at a position where occlusion does not occur.

According to the seventh embodiment, the measurement endoscope apparatus if includes the endoscope insertion unit 2, the imaging optical system 39f, the imaging element 21, the measurement processing unit 43, the reliability determination unit 44, and the notification control unit 451.

In the seventh embodiment, the notification control unit 451 sends a notification to prompt the user to perform an operation of moving the distal end 20 of the endoscope insertion unit 2 so that the distal end 20 of the endoscope insertion unit 2 is moved in a direction from the second position toward the first position when the reliability determination unit 44 determines that the reliability is low. In this way, it is possible to suppress a decrease in measurement accuracy due to the occurrence of occlusion.

Additional Explanation of First to Seventh Embodiments

The measurement endoscope apparatus 1 of the first embodiment includes the endoscope insertion unit 2, at least one imaging optical system (the first optical system 31 and the second optical system 32), the imaging element 21, and the measurement processing unit 43. At least one imaging optical system is disposed at the distal end 20 of the endoscope insertion unit 2. The imaging element 21 generates an image corresponding to an optical image obtained via the imaging optical system. The measurement processing unit 43 performs a measurement process by the principle of triangulation on the basis of an image and the camera parameters of a first position and a second position different from the first position. The measurement endoscope apparatus 1 further includes the reliability determination unit 44 and the notification control unit 451. The reliability determination unit 44 determines the reliability of the measurement process. The measurement process is performed on the basis of the measurement point set to an image corresponding to the optical image obtained via the imaging optical system at the first position. The notification control unit 451 sends a notification to prompt the user to perform an operation of moving the distal end 20 of the endoscope insertion unit 2 in a direction from the second position toward the first position when the reliability determination unit 44 determines that the reliability is low.

The measurement endoscope apparatus 1a of the second embodiment or the measurement endoscope apparatus 1b of the third embodiment includes the endoscope insertion unit 2, at least one imaging optical system (the first optical system 31 and the second optical system 32), the imaging element 21, the measurement processing unit 43, and the reliability determination unit 44 similarly to the measurement endoscope apparatus 1 of the first embodiment. The measurement endoscope apparatus 1a or 1b further includes the bending control unit 452. The bending control unit 451 controls the bending unit 22 so that the distal end 20 of the endoscope insertion unit 2 is moved in a direction from the second position toward the first position when the reliability determination unit 44 determines that the reliability is low.

In the first to third embodiments, the imaging optical system includes a first imaging optical system (the first optical system 31) and a second imaging optical system (the second optical system 32). The first imaging optical system is disposed at the first position. The second imaging optical system is disposed at the second position and the second imaging optical system has parallax with respect to the first imaging optical system. The image includes a first image corresponding to the first optical image obtained via the first imaging optical system and a second image corresponding to the second optical image obtained via the second imaging optical system. The measurement processing unit 43 (the measurement processing unit 43b) performs a measurement process on the basis of the first and second images.

The measurement endoscope apparatus 1c of the fourth embodiment includes the endoscope insertion unit 2c, the imaging optical system 39, the imaging element 21, the measurement processing unit 43c, the reliability determination unit 44, and the notification control unit 451. The imaging optical system 39 is disposed at the first position. The measurement endoscope apparatus 1c further includes the projection optical system 52. The projection optical system 52 is disposed at the second position and projects a predetermined pattern on the subject.

The measurement endoscope apparatus 1d of the fifth embodiment includes the endoscope insertion unit 2d, the imaging optical system 39d, the imaging element 21, the measurement processing unit 43, the reliability determination unit 44, and the notification control unit 451. The imaging optical system 39d is disposed at the first position. The measurement endoscope apparatus 1d further includes the projection optical system 52d. The projection optical system 52d is disposed at the second position and projects a predetermined pattern on the subject.

The measurement endoscope apparatus 1e of the sixth embodiment includes the endoscope insertion unit 2, the imaging optical system 39e, the imaging element 21, the measurement processing unit 43, the reliability determination unit 44, and the notification control unit 451. The image includes a first image corresponding to a first optical image obtained via the imaging optical system 39e at the first position and a second image corresponding to a second optical image obtained via the imaging optical system 39e at the second position. The measurement processing unit 43 performs a measurement process on the basis of the first and second images.

The measurement endoscope apparatus if of the seventh embodiment includes the endoscope insertion unit 2, the imaging optical system 39f, the imaging element 21, the measurement processing unit 43, the reliability determination unit 44, and the notification control unit 451. The image includes a first image corresponding to a first optical image obtained via the imaging optical system 39f at the first position and a second image corresponding to a second optical image obtained via the imaging optical system 39f at the second position. The measurement processing unit 43 performs a measurement process on the basis of the first and second images.

While preferred embodiments of the invention have been described and shown above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. An endoscope apparatus, comprising:
   an endoscope insertion unit;
   a first imaging optical system and a second imaging optical system disposed at a distal end of the endoscope insertion unit so as to be separated from each other in a parallax direction;
   an image sensor configured to generate a first image corresponding to a first optical image obtained via the first imaging optical system and a second image corresponding to a second optical image obtained via the second imaging optical system; and a processor configured to:
  set a measurement point in the first image,
  search the second image for a correspondence point corresponding to the measurement point,
  calculate 3-dimensional coordinates of the measurement point by a principle of triangulation using the measurement point and the correspondence point,
  determine the reliability of a measurement process, the measurement process being performed on the basis of the measurement point, and
  send a notification to prompt a user to perform an operation of moving the distal end toward the first imaging optical system in the parallax direction when the processor determines that the reliability is low.

2. The endoscope apparatus according to claim 1, wherein the processor is configured to:
  calculate a correlation value or a degree of difference between a position of the measurement point in the first image and a position of the correspondence point in the second image, and
  compare the correlation value or the degree of difference with a first predetermined value and to determine the reliability on the basis of the comparison result.

3. The endoscope apparatus according to claim 1, wherein the processor is configured to:
  determine whether or not occlusion has occurred and
  determine that the reliability is low when the processor determines that occlusion has occurred.

4. The endoscope apparatus according to claim 3, wherein the processor is configured to:
  set a first auxiliary measurement point on an epipolar line on the left side of the measurement point in the first image and set a second auxiliary measurement point on the epipolar line on the right side of the measurement point in the first image,
  calculate a first object distance at the first auxiliary measurement point and a second object distance at the second auxiliary measurement point,
  calculate a difference between the first object distance and the second object distance, and
  compare the difference with a second predetermined value and to determine that occlusion has occurred when the difference is larger than the second predetermined value.

5. The endoscope apparatus according to claim 1, wherein the processor is configured to:
  calculate a correlation value or a degree of difference between a position of the measurement point in the first image and a position of the correspondence point in the second image,
  determine whether or not occlusion has occurred, and
  determine the reliability on the basis of a comparison result obtained by comparing the correlation value or the degree of difference with a first predetermined value and a determination result obtained by the processor.

6. An endoscope apparatus, comprising:
  an endoscope insertion unit;
  a first imaging optical system and a second imaging optical system disposed at a distal end of the endoscope insertion unit so as to be separated from each other in a parallax direction;
  an image sensor configured to generate a first image corresponding to a first optical image obtained via the first imaging optical system and a second image corresponding to a second optical image obtained via the second imaging optical system; and
  a processor configured to:
    set a measurement point in the first image,
    search the second image for a correspondence point corresponding to the measurement point,
    calculate 3-dimensional coordinates of the measurement point by a principle of triangulation using the measurement point and the correspondence point,
    determine the reliability of a measurement process, the measurement process being performed on the basis of the measurement point, and
    output a bending signal to move the distal end toward the first imaging optical system in the parallax direction when the processor determines that the reliability is low.

7. The endoscope apparatus according to claim 6, wherein the processor is configured to:
  calculate a correlation value or a degree of difference between a position of the measurement point in the first image and a position of the correspondence point in the second image, and
  compare the correlation value or the degree of difference with a first predetermined value and to determine the reliability on the basis of the comparison result.

8. The endoscope apparatus according to claim 6, wherein the processor is configured to:
  determine whether or not occlusion has occurred, and
  determine that the reliability is low when the processor determines that occlusion has occurred.

9. The endoscope apparatus according to claim 8, wherein the processor is configured to:
  set a first auxiliary measurement point on an epipolar line on the left side of the measurement point in the first image and set a second auxiliary measurement point on the epipolar line on the right side of the measurement point in the first image,
  calculate a first object distance at the first auxiliary measurement point and a second object distance at the second auxiliary measurement point,
  calculate a difference between the first object distance and the second object distance, and
  compare the difference with a second predetermined value and to determine that occlusion has occurred when the difference is larger than the second predetermined value.

10. The endoscope apparatus according to claim 6, wherein the processor is configured to:
  calculate a correlation value or a degree of difference between a position of the measurement point in the first image and a position of the correspondence point in the second image,
  determine whether or not occlusion has occurred, and
  determine the reliability on the basis of a comparison result obtained by comparing the correlation value or the degree of difference with a first predetermined value and a determination result obtained by the processor.

11. The endoscope apparatus according to claim 6, wherein the processor is configured to:
  estimate 3-dimensional coordinates of the measurement point by processing at least a video signal corresponding to the first image and a video signal corresponding to the second image,
  calculate a bending amount for causing a point on a subject to be included in a field of view of the second imaging optical system, the point on the subject being at estimated 3-dimensional coordinates of the measurement point, determine, before the processor outputs the bending signal based on the bending amount, whether or not the point on the subject would be included in a field of view of the first imaging optical system if the distal end were virtually bent by the bending amount, and send a notification to prompt a user to perform an operation of moving the distal end away from the subject when it is determined that the point on the subject would not be included in the field of view of the first imaging optical system if the distal end were virtually bent by the bending amount.

12. The endoscope apparatus according to claim 6, wherein the parallax direction is a direction from a first optical center of the first imaging optical system toward a second optical center of the second imaging optical system, and the processor is configured to:
estimate 3-dimensional coordinates of the measurement point by processing at least a video signal corresponding to the first image and a video signal corresponding to the second image,
detect an edge at which a change in image density of the first image is relatively large by processing at least the video signal corresponding to the first image, the edge being on the parallax direction side of the measurement point in the first image,
calculate 3-dimensional coordinates of an edge point at the edge by the principle of triangulation by processing at least the video signal corresponding to the first image and the video signal corresponding to the second image,
calculate a virtual line that passes through estimated 3-dimensional coordinates of the measurement point and 3-dimensional coordinates of the edge point, and
calculate a bending amount necessary for moving the second optical center to a position on the virtual line or a position on an opposite side of the virtual line in the parallax direction.

13. The endoscope apparatus according to claim 6, wherein the parallax direction is a direction from a first optical center of the first imaging optical system toward a second optical center of the second imaging optical system, the endoscope apparatus includes a light receiving surface disposed at the distal end and disposed at an image forming position of the first imaging optical system and the second imaging optical system, and the processor is configured to:
calculate a virtual line that passes through a position of a measurement point on the light receiving surface and the first optical center, and
calculate a bending amount necessary for moving the second optical center to a position on the virtual line or a position on an opposite side of the virtual line in the parallax direction.

14. The endoscope apparatus according to claim 6, wherein the processor outputs the bending signal so that the distal end is bent by a predetermined bending amount, and the processor is configured to:
process at least a video signal corresponding to the first image after output of the bending signal based on the predetermined bending amount is performed, thereby searching for the same position as the position of the measurement point designated before the output of the bending signal based on the predetermined bending amount is performed and setting the measurement point at the position searched for, and
determine the reliability again on the basis of the correspondence point corresponding to the measurement point.

15. An endoscope apparatus, comprising:
an endoscope insertion unit;
a projection optical system disposed at a distal end of the endoscope insertion unit and configured to sequentially project a plurality of periodic patterns having different spatial phases on a subject;
an imaging optical system disposed at a position at the distal end different from a position at which the projection optical system is disposed and configured to sequentially form a plurality of optical images of the subject on which the plurality of patterns are projected;
an image sensor configured to generate a plurality of images corresponding to the plurality of optical images obtained via the imaging optical system; and
a processor configured to:
shift the spatial phase of the pattern,
set a measurement point in at least one of the plurality of images and calculate 3-dimensional coordinates of the measurement point by a phase shift method using the plurality of images,
determine the reliability of a measurement process, the measurement process being performed on the basis of the measurement point, and
send a notification to prompt a user to perform an operation of moving the distal end in a direction from the projection optical system toward the imaging optical system when the processor determines that the reliability is low.

16. An endoscope apparatus, comprising:
an endoscope insertion unit;
a projection optical system disposed at a distal end of the endoscope insertion unit and configured to sequentially project a plurality of periodic patterns having different spatial phases on a subject;
an imaging optical system disposed at a position at the distal end different from a position at which the projection optical system is disposed and configured to sequentially form a plurality of optical images of the subject on which the plurality of patterns are projected;
an image sensor configured to generate a plurality of images corresponding to the plurality of optical images obtained via the imaging optical system;
a processor configured to:
shift the spatial phase of the pattern,
set a measurement point in at least one of the plurality of images and calculate 3-dimensional coordinates of the measurement point by a phase shift method using the plurality of images,
determine the reliability of a measurement process, the measurement process being performed on the basis of the measurement point, and
output a bending signal to move the distal end in a direction from the projection optical system toward the imaging optical system when the processor determines that the reliability is low.

17. An endoscope apparatus, comprising:
an endoscope insertion unit;
a projection optical system disposed at a distal end of the endoscope insertion unit and configured to project a random pattern on a subject;

an imaging optical system disposed at a position at the distal end different from a position at which the projection optical system is disposed and configured to form an optical image of the subject on which the random pattern is projected;

an image sensor configured to generate a first image corresponding to an optical image obtained via the imaging optical system; and processing unit, a processor configured to:
set a measurement point in the first image,
search a second image of the random pattern for a correspondence point corresponding to the measurement point,
calculate 3-dimensional coordinates of the measurement point by a principle of triangulation using the measurement point and the correspondence point,
determine the reliability of a measurement process, the measurement process being performed on the basis of the measurement point, and
send a notification to prompt a user to perform an operation of moving the distal end in a direction from the projection optical system toward the imaging optical system when the processor determines that the reliability is low.

18. An endoscope apparatus, comprising:
an endoscope insertion unit;
a projection optical system disposed at a distal end of the endoscope insertion unit and configured to project a random pattern on a subject;
an imaging optical system disposed at a position at the distal end different from a position at which the projection optical system is disposed and configured to form an optical image of the subject on which the random pattern is projected;
an image sensor configured to generate a first image corresponding to the optical image obtained via the imaging optical system;
a processor configured to:
set a measurement point in the first image,
search a second image of the random pattern for a correspondence point corresponding to the measurement point,
calculate 3-dimensional coordinates of the measurement point by a principle of triangulation using the measurement point and the correspondence point,
determine the reliability of a measurement process, the measurement process being performed on the basis of the measurement point, and
output a bending signal to move the distal end in a direction from the projection optical system toward the imaging optical system when the processor determines that the reliability is low.

19. An endoscope apparatus, comprising:
an endoscope insertion unit;
an imaging optical system disposed at a distal end of the endoscope insertion unit and configured to form an optical image of a subject at a first position and a second position different from the first position;
an image sensor configured to generate a first image corresponding to a first optical image obtained via the imaging optical system at the first position and a second image corresponding to a second optical image obtained via the imaging optical system at the second position; and a processor configured to:
set a measurement point in the first image,
search the second image for a correspondence point corresponding to the measurement point,
calculate 3-dimensional coordinates of the measurement point by a principle of triangulation using the measurement point and the correspondence point,
determine the reliability of a measurement process, the measurement process being performed on the basis of the measurement point, and
send a notification to prompt a user to perform an operation of moving the distal end in a direction from the second position toward the first position when the processor determines that the reliability is low.

20. An endoscope apparatus, comprising:
an endoscope insertion unit;
an imaging optical system disposed at a distal end of the endoscope insertion unit and configured to form an optical image of a subject at a first position and a second position different from the first position;
an image sensor configured to generate a first image corresponding to a first optical image obtained via the imaging optical system at the first position and a second image corresponding to a second optical image obtained via the imaging optical system at the second position;
a processor configured to:
set a measurement point in the first image,
search the second image for a correspondence point corresponding to the measurement point,
calculate 3-dimensional coordinates of the measurement point by a principle of triangulation using the measurement point and the correspondence point,
determine the reliability of a measurement process, the measurement process being performed on the basis of the measurement point, and
output a bending signal to move the distal end in a direction from the second position toward the first position when the processor determines that the reliability is low.

21. An endoscope apparatus, comprising:
an endoscope insertion unit;
at least one imaging optical system disposed at a distal end of the endoscope insertion unit;
an image sensor configured to generate an image corresponding to an optical image obtained via the imaging optical system; and
a processor configured to:
perform a measurement process by a principle of triangulation on the basis of the image and camera parameters of a first position and a second position different from the first position,
determine the reliability of the measurement process, the measurement process being performed on the basis of the measurement point set in the image corresponding to the optical image obtained via the imaging optical system at the first position, and
send a notification to prompt a user to perform an operation of moving the distal end in a direction from the second position toward the first position when the processor determines that the reliability is low.

22. The endoscope apparatus according to claim 21,
wherein the imaging optical system includes a first imaging optical system and a second imaging optical system,
the first imaging optical system is disposed at the first position, the second imaging optical system is disposed at the second position, the second imaging optical system having parallax with respect to the first imaging optical system, the image includes a first image corresponding to a first optical image obtained via the first imaging optical system and a second image corresponding to a second optical image obtained via the second imaging optical system, and the processor performs the measurement process on the basis of the first image and the second image.

23. The endoscope apparatus according to claim 21, wherein the imaging optical system is disposed at the first position, and the endoscope apparatus includes a projection optical system disposed at the second position and configured to project a predetermined pattern on a subject.

24. The endoscope apparatus according to claim 21, wherein the image includes a first image corresponding to a first optical image obtained via the imaging optical system at the first position and a second image corresponding to a second optical image obtained via the imaging optical system at the second position, and the processor performs the measurement process on the basis of the first image and the second image.

25. The endoscope apparatus according to claim 21, wherein the processor is configured to:

determine whether or not occlusion has occurred, and determine that the reliability is low when the processor determines that occlusion has occurred.

26. An endoscope apparatus, comprising:

an endoscope insertion unit;

at least one imaging optical system disposed at a distal end of the endoscope insertion unit;

an image sensor configured to generate an image corresponding to an optical image obtained via the imaging optical system; a processor configured to:

perform a measurement process by a principle of triangulation on the basis of the image and camera parameters of a first position and a second position different from the first position, determine the reliability of the measurement process, the measurement process being performed on the basis of the measurement point set in the image corresponding to the optical image obtained via the imaging optical system at the first position, and output a bending signal to move the distal end in a direction from the second position toward the first position when the processor determines that the reliability is low.

\* \* \* \* \*